(12) United States Patent
Mousa et al.

(10) Patent No.: US 9,198,887 B2
(45) Date of Patent: *Dec. 1, 2015

(54) THYROID HORMONE ANALOGS AND METHODS OF USE

(71) Applicants: Shaker A. Mousa, Wynantskill, NY (US); Faith B. Davis, West Sand Lake, NY (US); Paul J. Davis, West Sand Lake, NY (US)

(72) Inventors: Shaker A. Mousa, Wynantskill, NY (US); Faith B. Davis, West Sand Lake, NY (US); Paul J. Davis, West Sand Lake, NY (US)

(73) Assignee: NANOPHARMACEUTICALS LLC, Rensselaer, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/078,713

(22) Filed: Nov. 13, 2013

(65) Prior Publication Data

US 2014/0072635 A1  Mar. 13, 2014

Related U.S. Application Data

(60) Continuation-in-part of application No. 13/975,735, filed on Aug. 26, 2013, now abandoned, which is a continuation-in-part of application No. 12/626,068, filed on Nov. 25, 2009, now Pat. No. 8,518,451, which is a division of application No. 10/943,072, filed on Sep. 15, 2004, now Pat. No. 7,785,632.

(60) Provisional application No. 60/502,721, filed on Sep. 15, 2003.

(51) Int. Cl.
| | |
|---|---|
| *A61K 31/192* | (2006.01) |
| *A61K 45/06* | (2006.01) |
| *A61K 31/7068* | (2006.01) |
| *A61K 31/225* | (2006.01) |
| *A61K 31/337* | (2006.01) |
| *A61K 31/704* | (2006.01) |

(52) U.S. Cl.
CPC ............. *A61K 31/192* (2013.01); *A61K 31/225* (2013.01); *A61K 31/337* (2013.01); *A61K 31/704* (2013.01); *A61K 31/7068* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,625,214 | A | 12/1971 | Higuchi |
| 4,205,058 | A | 5/1980 | Wagner et al. |

(Continued)

FOREIGN PATENT DOCUMENTS

| | | |
|---|---|---|
| CA | 2673133 A1 | 11/2008 |
| CN | 1126589 | 7/1996 |

(Continued)

OTHER PUBLICATIONS

A.D.A.M. Medical Encyclopedia, www.ncbi.nlm.nih.gov/pubmedhealth/PMH0001308/, downloaded Jul. 12, 2012. 6 pages.

(Continued)

*Primary Examiner* — Ernst V Arnold
*Assistant Examiner* — Jianfeng Song
(74) *Attorney, Agent, or Firm* — Schmeiser, Olsen & Watts, LLP

(57) ABSTRACT

Disclosed are methods of treating subjects having conditions related to angiogenesis including administering an effective amount of a polymeric form of thyroid hormone, or an antagonist thereof, to promote or inhibit angiogenesis in the subject. Compositions of the polymeric forms of thyroid hormone, or thyroid hormone analogs, are also disclosed.

6 Claims, 44 Drawing Sheets

(56) References Cited

U.S. PATENT DOCUMENTS

| | | |
|---|---|---|
| 4,650,751 A | 3/1987 | Siegel et al. |
| 4,789,734 A | 12/1988 | Pierschbacher |
| 4,801,504 A | 1/1989 | Burdick et al. |
| 4,801,575 A | 1/1989 | Pardridge |
| 4,906,474 A | 3/1990 | Langer et al. |
| 4,925,673 A | 5/1990 | Steiner et al. |
| 4,968,590 A | 11/1990 | Kuberasampath et al. |
| 5,011,486 A | 4/1991 | Aebischer et al. |
| 5,091,513 A | 2/1992 | Huston et al. |
| 5,104,895 A | 4/1992 | Spinelli et al. |
| 5,158,978 A | 10/1992 | Rubin |
| 5,225,204 A | 7/1993 | Chen et al. |
| 5,231,000 A | 7/1993 | Majocha et al. |
| 5,304,121 A | 4/1994 | Sahatjian |
| 5,410,016 A | 4/1995 | Hubbell et al. |
| 5,438,126 A | 8/1995 | DeGroot et al. |
| 5,482,719 A | 1/1996 | Guillet et al. |
| 5,571,840 A | 11/1996 | Mayor et al. |
| 5,591,709 A | 1/1997 | Lindenbaum |
| 5,593,688 A | 1/1997 | Baldeschwieler |
| 5,648,506 A | 7/1997 | Desai et al. |
| 5,766,635 A | 6/1998 | Spenleuhauer et al. |
| 6,139,870 A | 10/2000 | Verrecchia |
| 6,316,412 B1 | 11/2001 | Ginsberg et al. |
| 6,414,037 B1 | 7/2002 | Pezzuto et al. |
| 6,482,406 B1 | 11/2002 | Stewart |
| 6,677,473 B1 | 1/2004 | Madison et al. |
| 6,740,680 B1 | 5/2004 | Danforth, Jr. et al. |
| 6,818,620 B2 | 11/2004 | Bhatnagar |
| 6,821,947 B2 | 11/2004 | Iozzo |
| 7,166,155 B2 | 1/2007 | Ishikawa |
| 7,638,558 B2 | 12/2009 | Breitenkamp et al. |
| 7,785,632 B2 | 8/2010 | Mousa et al. |
| 7,807,621 B2 | 10/2010 | Mazar et al. |
| 8,026,209 B2 | 9/2011 | Gaillard et al. |
| 8,071,134 B2 | 12/2011 | Mousa et al. |
| 8,242,171 B2 | 8/2012 | Sinclair et al. |
| 8,518,451 B2 | 8/2013 | Mousa et al. |
| 8,668,926 B1 | 3/2014 | Davis et al. |
| 8,802,240 B2 | 8/2014 | Davis et al. |
| 2001/0021763 A1 | 9/2001 | Harris |
| 2001/0046521 A1 | 11/2001 | Zasloff et al. |
| 2002/0049247 A1 | 4/2002 | Chen |
| 2002/0137676 A1 | 9/2002 | Hsiang et al. |
| 2002/0151594 A1 | 10/2002 | Morkin et al. |
| 2003/0027940 A1 | 2/2003 | Lang et al. |
| 2003/0138557 A1 | 7/2003 | Allison |
| 2003/0157098 A1 | 8/2003 | Laug |
| 2003/0162758 A1 | 8/2003 | Schwartz et al. |
| 2003/0165576 A1 | 9/2003 | Fujii et al. |
| 2004/0013728 A1 | 1/2004 | Oh et al. |
| 2004/0033259 A1 | 2/2004 | Hanshew, Jr. et al. |
| 2005/0124862 A1 | 6/2005 | Mousa et al. |
| 2005/0158376 A1 | 7/2005 | Sardi et al. |
| 2005/0171027 A1 | 8/2005 | Sinclair et al. |
| 2005/0222387 A1 | 10/2005 | Debatin et al. |
| 2005/0249721 A1 | 11/2005 | Houston et al. |
| 2005/0272817 A1 | 12/2005 | Heino |
| 2006/0166303 A1 | 7/2006 | Spanuth |
| 2006/0210539 A1 | 9/2006 | Zhang |
| 2007/0117841 A1 | 5/2007 | Ozes et al. |
| 2007/0190160 A1 | 8/2007 | Turos et al. |
| 2008/0124280 A1 | 5/2008 | Mousa et al. |
| 2008/0193377 A1 | 8/2008 | Line et al. |
| 2009/0022806 A1 | 1/2009 | Mousa et al. |
| 2009/0175862 A1 | 7/2009 | Silverio et al. |
| 2010/0112079 A1 | 5/2010 | Mousa et al. |
| 2010/0159021 A1 | 6/2010 | Davis et al. |
| 2010/0209382 A1 | 8/2010 | Alexander-Bridges et al. |
| 2010/0255108 A1 | 10/2010 | Lin et al. |
| 2011/0052715 A1 | 3/2011 | Davis et al. |
| 2011/0142941 A1 | 6/2011 | Davis et al. |
| 2012/0258069 A1 | 10/2012 | Alexander-Bridges et al. |
| 2012/0315320 A1 | 12/2012 | Davis et al. |
| 2014/0072646 A1 | 3/2014 | Mousa et al. |
| 2014/0199375 A1 | 7/2014 | Mousa et al. |

FOREIGN PATENT DOCUMENTS

| | | |
|---|---|---|
| WO | 9500135 | 1/1995 |
| WO | 9640048 | 12/1996 |
| WO | 9833942 | 8/1998 |
| WO | 9856771 | 12/1998 |
| WO | 9958119 A1 | 11/1999 |
| WO | 9962549 | 12/1999 |
| WO | 0064431 A1 | 11/2000 |
| WO | 0078815 A1 | 12/2000 |
| WO | 0113031 A2 | 2/2001 |
| WO | 0113936 A1 | 3/2001 |
| WO | 0176589 A1 | 10/2001 |
| WO | 0203914 A2 | 1/2002 |
| WO | 0249501 A2 | 6/2002 |
| WO | 02060389 A2 | 8/2002 |
| WO | 03075741 A2 | 9/2003 |
| WO | 2004013728 A2 | 2/2004 |
| WO | 2004069201 A2 | 8/2004 |
| WO | 2005027895 A2 | 3/2005 |
| WO | 2006003014 A2 | 1/2006 |
| WO | 2006031922 A2 | 3/2006 |
| WO | 2007035612 A2 | 3/2007 |
| WO | 2008051291 A2 | 5/2008 |
| WO | 2008140507 A2 | 11/2008 |
| WO | 2010120506 A2 | 10/2010 |
| WO | 2010148007 A2 | 12/2010 |

OTHER PUBLICATIONS

Abdollahi et al., "Inhibition of α☐β3 Integrin Survival Signaling Enhances Antiangiogenic and Antitumor Effects of Radiotherapy", Clin. Cancer Research., 11(17):6270-6279 (2005) 10 pages.

Albert et al., "Integrin α☐β3 Antagonist Cilengitide Enhances Efficacy of Radiotherapy in Endothelial Cell and Non-Small-Cell Lung Cancer Models", Int. J. Radiat. Oncol. Biol. Phys., 65(5):1536-1543 (2006) 8 pages.

Alexis et al., "Nonocclusive Common Carotid Artery Thrombosis in the Rat Results in Reversible Sensorimotor and Cognitive Behavorial Deficits", Stroke, 26:2338-2346 (1995) 16 pages.

Ali et al., "Angiogenesis as a potential biomarker in prostate cancer chemoprevention trials", Urology, 57(Suppl 4A):143-147 (2001) 5 pages.

Ali et al., "Apoptosis-Inducing effect of erlotinib is potentiated by 3,3'-diindolylmethane in vitro and in vivo using an orthotopic model of pancreatic cancer", Mol. Cancer Ther., 7(6):1708-1719(2008) 12 pages.

Ali et al., "High levels of oestrogen receptor-α in tumorigenesis: inhibition of cell growth and angiogenic factors", Cell Prolif., 34(4):223-231 (2001) 10 pages.

Allen, A.R., "Surgery of experimental lesion of spinal cord equivalent to crush injury of fracture dislocation of spinal column", J. Am. Med. Assoc., 57(11):878-880 (1911) 4 pages.

Almog et al., "Transcriptional Switch of Dormant Tumors to Fast-Growing Angiogenic Phenotype", Cancer Res., 69 (3):836-844 (2009).

Amirkhosravi et al., "Antimestatatic effect of tinzaparin, a low-molecular-weight heparin", J. Thromb. Haemost., 1:1972-1976 (2003) 5 pages.

Amirkhosravi et al., "Inhibition of tumor cell-induced platelet aggregation and lung metastasis by the oral Gpllb/IIIa antagonist XV454", J. Thrombosis and Haemostasis, 3:549-554 (2003) 6 pages.

Ando et al., "Induction by carbon-ion irradiation of the expression of vascular endothelial growth factor in lung carcinoma cells", Int. J. Radiat. Biol., 76(8):1121-1127 (2000) 7 pages.

Application No. PCT/US2004/030583, International Search Report and the Written Opinion of the International Searching Authority, or the Declaration dated Mar. 7, 2005. 11 pages.

Application No. PCT/US2005/032813, International Search Report dated Dec. 22, 2006. 6 pages.

(56) References Cited

OTHER PUBLICATIONS

Application No. PCT/US2007/009026, International Search Report dated Nov. 7, 2008. 5 pages.
Application No. PCT/US2009/069104, International Search Report dated Mar. 4, 2010 5 pages.
Application No. PCT/US2007/026167, International Search Report dated Oct. 30, 2008. 3 pages..
Application No. PCT/US2010/038700, International Search Report dated Mar. 21, 2011. 4 pages.
Application No. PCT/US2006/036243, International Search Report dated Jul. 30, 2007. 7 pages..
Application No. PCT/US2010/029371, International Search Report dated Aug. 24, 2010. 5 pages.
Audus et al., "Bovine Brain Microvessel Endothelial Cell Monolayers as a Model System for the Blood-Brain Barrier", in Biological Approaches to the Controlled Delivery of Drugs, Ann. N. Y. Acad. Sci., 507:9-18 (1987) 11 pages.
Avis, K.E., "Parenteral Preparations", in Remington's Pharmaceutical Sciences, 15th Ed., Chapter 84, pp. 1461-1487, Mack Publishing Co., Easton, Pennsylvania (1975) 29 pages.
Balestrazzi et al., "Leaf-associated bacteria from transgenic white poplar producing resveratrol-like compounds: isolation, molecular characterization, and evaluation of oxidative stress tolerance", Can. J. Microbiol., 55:829-840 (2009) 12 pages.
Balin-Gauthier et al., "In vivo and in vitro antitumor activity of oxaliplatin in combination with cetuximab in human colorectal tumor cell lines expressing different level of EGFR", Cancer Chemother. Pharmacol., 57:709-718 (2006) 8 pages.
Baur et al., "Resveratrol improves health and survival of mice on a high-calorie diet", Nature, 444:337-342 (2006) 6 pages.
Baur et al., "Therapeutic potential of resveratrol: the in vivo evidence", Nat. Rev. Drug Discov., 5:493-506 (2006) 14 pages.
Bederson et al., "Rat Middle Cerebral Artery Occlusion: Evaluation of the Model and Development of a Neurologic Examination", Stroke, 17(3):472-476 (1986) 6 pages.
Belenky et al., "NAD+ metabolism in health and disease", Trends Biochem. Sci., 32(1):12-19 (2007) 9 pages.
Benedetti et al., "Life Tables and Survivor Functions", in BMDP Statistical Software Manual, BMDP Statistical Software, Inc., vol. 2, p. 573 and 689-718 (1988) 33 pages.
Ben-Hur et al., "Thermally Enhanced Radioresponse of Cultured Chinese Hamster Cells: Inhibition of Repair of Sublethal Damage and Enhancement of Lethal Damage", Radiat Res., 58:38-51 (1974) 14 pages.
Bennett et al., "A peptide derived from α-fetoprotein prevents the growth of estrogen-dependent human breast cancers sensitive and resistant to tamoxifen", Proc. Natl, Acad. Sci. USA, 99(4):2211-2215 (2002) 5 pages.
Berger et al., "Modes of resistance to anti-angiogenic therapy", Nat. Rev. Cancer, 8(8):592-603 (2008) 23 pages.
Bergh et al., "Integrin $\alpha\Box\beta3$ contains a cell surface receptor site for thyroid hormone that is linked to activation of mitogen-activated protein kinase and induction of angiogenesis", Endocrinology, 146( &):2864-2871 (2005) 8 pages.
Bergstrom et al., "Iodine-123 labelled Z-(R,R)-IQNP: a potential radioligand for visualization of M1 and M2 muscarinic acetylcholine receptors in Alzheimer's disease", Eur. J. Nucl. Med., 26(11):1482-1485 (1999).
Bergstrom et al., "Reduction of fibrinogen absorption on PEG-coated polystyrene surfaces", J. Biomed. Mat. Res., 26:779-790 (1992) 12 pages.
Beum et al., "Binding of Rituximab, Trastuzumab, Cetuximab, or mAb T101 to Cancer Cells Promotes Trogocytosis Mediated by THP-1 Cells and Monocytes", J. Immunol., 181:8120-8132 (2008) 13 pages.
Bhat et al., "NCAM-180, the largest component of the neural cell adhesion molecule, is reduced in dysmyelinating quaking mutant mouse brain", Brain Res., 452:373-377 (1988) 5 pages.

Bilello et al., "Effect of 2', 3'-Didehydro-3'-Deoxythymidine in an in Vitro Hollow-Fiber Pharmacodynamic Model System Correlates with Results of Dose-Ranging Clinical Strudies", Antimicrob Agents Chemother., 38(6):1386-1391 (1994) 6 pages.
Blaszczyk-Thurin et al., "An Experimental Vaccine Expressing Wild-Type p53 induces Protective Immunity Against Glioblastoma Cells with High Levels of Endogenous p53", Scand. J. Immunol., 56:361-375 (2002) 15 pages.
Blight, A.R., "Macrophages and Inflammatory Damage in Spinal Cord Injury", J. Neurotrauma, 9(Suppl. 1):S83-S91 (1992) 10 pages.
Blood et al., "Tumor interactions with the vasculature: angiogenesis and tumor metastasis", Bioch. Biophys. Acta, 1032:89-118 (1990) 30 pages.
Bokemeyer et al., "Fluorouracil, Leucovorin, and Oxaliplatin With and Without Cetuximab in the First-Line Treatment of Metastatic Colorectal Cancer", J. Clin. Oncol., 27(5):663-671 (2009) 9 pages.
Bornebroek et al., "Potential for imaging cerebral amyloid deposits using 123I-labelled serum amyloid P component and SPET", Cucl. Med. Commun., 17:929-933 (1996) 6 pages.
Bozarth et al., "An improved method for the quantitation of cellular migration: Rose of $\alpha\Box\beta3$ integrin in endothelial and smooth muscle cell migration", Meth. Cell Sci., 19(3):179-187 (1997) 9 pages.
Brachmann et al., "The SIR2 gene family, conserved from bacteria to humans, functions in silencing, cell cycle progression, and chromosome stability", Genes Dev. 9:2888-2902 (1995) 15 pages.
Braughler et al., "Involvement of Lipid Peroxidation in CNS Injury", J. Neurotrauma, 9(Suppl. 1):S1-S7 (1992) 8 pages.
Breier et al., "The role of vascular endothelial growth factor in blood vessel formation", Trends in Cell Biol., 6:454_456 (1996) 3 pages.
Bridoux et al., "Semisynthesis and pharmacological activities of Tetrac analogs: Angiogenesis modulators", Bioorg. Med. Chem. Lett., 19:3259-3263 (2009) 5 pages.
Bridoux et al., "Semisynthesis and pharmacological activities of thyroxine analogs: Development of new angiogenesis modulators", Bioorg. Med. Chem. Lett, 20(11):3394-3398 (2010) 5 pages.
Brockhoff et al., "Differential impact of Cetuximab, Pertuzumab and Trastuzumab on BT474 and SK-BR-3 breast cancer proliferation", Cell Prolif., 40:488-507 (2007) 20 pages.
Brooks et al., "Antintegrin $\alpha\Box\beta3$ blocks human breast cancer growth and angiogenesis in human skin", J. Clin. Invest., 96(4):1815-1822 (1995) 8 pages.
Bulitta et al., "Development and Qualification of a Pharmacodynamic Model for the Pronounced Inoculum Effect of Ceftazidime against Pseudomonas aeruginosa", Antimicrob. Agents Chemother., 53(1):46-56 (2009) 11 pages.
Burgman et al., "Effect of Inhibitors of Poly(ADP-Ribose)Polymerase on the Radiation Resposne of HeLa S3 Cells", Radiat. Res., 119:380-386 (1989) 7 pages.
Carmeliet et al., "Molecular Basis of Angiogenesis Role of VEGF and VE-Cadherin", Ann. N. Y. Acad. Sci., 902:249-264 (2000) 16 pages.
Chanoine et al., "The role of transthyretin in the transport of thyroid hormone to cerebrospinal fluid and brain", Acta Medica Austriaca, 19(Suppl. 1):25-28 (19920) 5 pages.
Charness et al., "Ethanol Increases the Expression of Functional Delta-Opioid Receptors in Neurblastoma x Glioma NG108-15 Hybrid Cells", J. Biol. Chem., 261(7):3164-3169 (1986) 6 pages.
Charo et al., "The Vitronectin Receptor $\alpha\Box\beta3$ Binds Fibronectin and Acts in Concert with $\alpha5\beta1$ in Promoting Cellular Attachment and Spreading on Fibronectin", J. Cell Biol., 111(6 Pt. 1): 2795-2800 (1990) 6 pages.
Chase et al., "Principles of Radioisotope Methodology", 2nd Ed., Minneapolis, MN. Burgess Publ. Co., 1962, pp. 68, 87-90. 7 pages.
Chavakis et al., "Kinetics of integrin expression in the mouse model of proliferative retinopathy and success of secondary intervention with cyclic RGD peptides", Diabetologia, 45:262-267 (2002) 6 pages.
Cheng et al., "Molecular Aspects of Thyroid Hormone Actions", Endocri. Rev., 31(2): 139-170 (2010) 32 pages.
Cheresh et al., "Biosynthetic and Functional Properties of an Arg-Gly-Asp-directed Receptor Involved in Human Melanoma Cell

(56) References Cited

OTHER PUBLICATIONS

Attachment to Vitronectin, Fibrinogen and von Willibrand Factor", J. Biol. Chem., 262(36):17703-17711 (1987) 9 pages.
Cheresh, D.A., "Human endothelial cells synthesize and express an Arg-Gly-Asp-directed adhesion receptor involved in attachment to fibrinogen and von Willibrand factor", Proc. Natl. Acad. Sci. U.S.A., 84:6471-6475 (1987) 9 pages.
Chiaguri et al., "Anoikis: A necessary death program for anchorage-dependent cells", Biochem. Pharmacol., 76:1352-1364 (2008) 13 pages.
Chinese Office Action for Application No. 2004800331846 dated Mar. 5, 2010 7 pages.
Chinese Office Action for Application No. 2004800331846, mailed Nov. 30, 2007, cited CN 1126589, 6 pages.
Clifton et al., "Marked Protection by Moderate Hypothermia After Experimental Traumatic Brain Injury", J. Cereb. Blood Flow Matab., 11(1):114-121 (1991) 9 pages.
Cody et al., "Molecular modeling of the thyroid hormone interactions with α□ β3 integrin", Steriods, 72:165-170 (2007) 6 pages.
Cohen-Jonathan et al., "Radioresistance Induced by the High Molecular Forms of the Basic Fibroblast Growth Factor is associated with an increased G2 Delay and a Hyperphosphorylation of p34CDC2 in HeLa Cells", Cancer Res., 57:1364-1370 (1997) 7 pages.
Cohen-Jonathan et al., "α□ β3 integrin pathway controls glioma radioresistance through ILK", Proc. Amer. Assoc. Cancer Res., 47:5180 (2006) (Abstract Only) 2 pages.
Cox et al., "The repair of potentially lethal damage in X-irradiated cultures of normal and ataxia telangiectasia human fibroblasts", Int. J. Radiat. Biol., 39(4):357-365 (1981) 9 pages.
Cristofanilli et al., "Thyroid Hormone and Breast Carcinoma. Primary Hypothyroidism is Associated with a Reduced Incidence of Primary Breast Carcinoma", Cancer, 103(6):1122-1128 (2005) 7 pages.
D'Arezzo et al., "Rapid Nongenomic Effects of 3,5,3'-Triiodo-L Thyronine on the Intracellular pH of L-6 Myoblasts are Mediated by Intracellular Calcium Mobilzation and Kinase Pathways", Endocrinol., 145(12):5694-5703 (2004) 10 pages.
Database BIOSIS [Online], Accession No. PREV20040016159, Abstract, Mousa et al., "Discovery of pro-angiogenic effects of thyroid hormone and analogs", Blood, 102(11):77b-78b (2003) 1 page.
Davis et al., "Acting via a Cell Surface Receptor, Thyroid Hormone is a Growth Factor for Glioma cells," Cancer Res., 66(14):7270-7275 (2006) 6 pages.
Davis et al., "Cell-surface receptor for thyroid hormone and tumor cell proliferation", Expert Review in Endocrinology and Metabolism, 1(6):753-761 (2006) 10 pages.
Davis et al., "Mechanisms of nongenomic actions of thyroid hormone", Frontiers Neuroendocrinol., 29:211-218 (2008) 8 pages.
Davis et al., "Proangiogenic Action of Thyroid Hormone is Fibroblast Growth Factor-Dependent and is initiated at the Cell Surface." Cir. Res., 94(2004):1500-1506 7 pages.
Davis et al., "Promotion by thyroid hormone of cytoplasm-to-nucleus shutting of thyroid hormone receptors", Steroids, 73:1013-1017 (2008) 5 pages.
Davis et al., "Thyroxine Promotes Association of Mitogen-activated Protein Kinase and Nuclear Thyroid Hormone Receptor (TR) and Causes Serine Phosphorylation of TR", J. Biol. Chem., 275(48):38032-38039 (2000) 8 pages.
Davis et al., "Translational implications of nongenomic actions of thyroid hormone initiated at its integrin receptor", Am. J. Physiol. Endocrinol. Metab., 297:E1238-E1246 (2009) 9 pages.
De la Cruz et al., "Effect of Aspirin Plus Dipyridamole on the Retinal Vascular Pattern in Experimental Diabetes Mellitus", J. Pharmacol. Exp. Ther., 280(1):454-459 (1997) 6 pages.
Deardorff, D.L., "Isotonic Solutions", in Remington's Pharmaceutical Sciences, 15th Ed., Chapter 79, pp. 1405-1412, Mack Publishing Co., Easton (1975) 10 pages.
DeFesi et al., "3,5,3'-Triiodothyronine Effects on the Growth Rate and Cell Cycle of Cultured GC Cells", Endocrinol., 108(1):259-267(1981) 9 pages.
Demediuk et al., "Traumatic Spinal Cord Injury in Rats Causes Increases in Tissue Thromboxane But Not Peptidoleukotrienes", J. Neurosci. Res., 20:115-121 (1988) 7 pages.
DeRyck et al., "Neocortical localization of tactile/proprioceptive limb placing reactions in the rat", Brain Res., 573 (1):44-60 (1992) 18 pages.
Di Chiro et al., "Glucose utilization of cerebral gliomas measured by [18F] fluorodeoxyglucose and positron emission tomography", Neurology, 32(12):1323-1329 (1982) 8 pages.
Dietrich et al., "Post-traumatic brain hypothermia reduces histopathological damage following concussive brain injury in the rat", Acta Neuropathol., 87(3):250-258 (1994) 10 pages.
Ding et al., "Radioprotection of Hematopoietic Tissue by Fibroblast Growth Factors in Fractionated Radiation Experiments", Acta Onocol., 36(3):337-340 (1997) 4 pages.
Dixon et al., "A fluid percussion model of experimental brain injury in the rat", J. Neurosurg., 67(1):110-119 (1987) 11 pages.
Drusano et al., "Pharmacodynamics of Abacavir in an in Vitro Hollow-Fiber Model System", Antimicrob. Agents Chemother., 46(2):464-470 (2002) 7 pages.
Dupont et al., "Antiangiogenic and antimetastatic properties of Neovastat (941), an orally active extract derived from cartilage tissue", Clin. Experim. Metastasis, 19:145-153 (2002) 9 pages.
Edwards et al., "Trypsinized BHK21 cells aggregate in the presence of metabolic inhibitors and in the absence of divalent cations", J. Cell Sci., 19(3):653-667 (1975) 16 pages.
Elkind et al., "Radiation Response of Mammalian Cells Grown in Culture. 1. Repair of X-Ray Damage in Surviving Chinese Hamster Cells", Radiat. Res., 13:556-593 (1960) 38 pages.
Elvin et al., "Cell Adhesiveness and the Cell Cycle: Correlation in Synchronized Balb/c 3T3 Cells", Biol. Cell, 48:1-10 (1983) 10 pages.
Ely and Berne, "Protective Effects of Adenosine in Myocardial lschemia", Circulation, 85:893-904 (1992) 13 pages.
Ethier et al., "Adenosine stimulates proliferation of human endothelial cells in culture", Am. J. Physiol., 265:H131-H138 (1993) 8 pages.
Everts et al., "Uptake of 3,3',5.5'-Tetraiodothyroacetic Acid and 3,3',5'-Triiodothyronine in Cultured Rat Anterior Pituitary Cells and Their Effects on Thyrotropin Secretion", Endocrinol., 136(10):4454-4461 (1995) 8 pages.
Faden et al., "Endogenous Opioid Immunoreactivity in Rat Spinal Cord Following Traumatic Injury", Ann. Neurol., 17 (4):386-390 (1985) 5 pages.
Faden, A.I., "Experimental Neurobiology of Central Nervous System Trauma", Crit. Rev. Neurobiol., 7(3/4):175-186 (1993) 13 pages.
Feeney et al., "Amphetamine, Haloperidol, and Experience Interact to Affect Rate of Recovery After Motor Cortex Injury", Science, 217(4562):855-857 (1982) 4 pages.
Fei et al., "P53 and radiation responses", Oncogene, 22:5774-5783 (2003) 10 pages.
Felding-Habermann et al., "Integrin activation controls metastasis in human breast cancer", Proc. Natl. Acad. Sci. U.S.A., 98(4):1853-1858 (2001) 6 pages.
Feng et al., "Fibrin and Collagen Differentially Regulate Human Dermal Microfascular Endothelial Cell Integrins: Stablization of α□ β3 mRNA by Fibrin", J. Invest. Dermatol., 113(6):913-919 (1999) 7 pages.
Fife et al., "Effects of tetracyclines on angiogenesis in vitro", Cancer Letters, 153:75-78 (2000) 4 pages.
Folkman, J., "Angiogenesis in cancer, vascular, rheumatoid and other disease", Nat. Med., 1(1):27-31 (1995) 5 pages.
Freese et al., "Characterization and mechanism of glutamate neurotoxicity in primary striatal cultures", Brain Res., 521 (112):254-264 (1990) 12 pages.
Frye, R.A., "Characterization of Five Human cDNAs with Homonology to the Yeast SIR2. Gene: Sir2-like Proteins (Sirtuins) Metabolize NAD and May Have Protein ADP-Ribosyltransferase Activity", Biochem. Biophys. Res. Comm., 260:273-279 (1999) 7 pages.

(56) References Cited

OTHER PUBLICATIONS

Fujii et al., "Crystal Structure of Trimestatin, a Disintegrin Containing a Cell Adhesion Recognition Motif RGD", J. Mol. Biol., 332:1115-1122 (2003) 8 pages.
Gavrieli et al., "Identification of Programmed Cell Death in Situ via Specific Labeling of Nuclear DNA Fragmentation", J. Cell. Biol., 119(3):493-501 (1992) 9 pages.
GenBank Accession No. AF083106, Apr. 14, 2000 5 pages.
GenBank Accession No. AF083107, Mar. 21, 2001. 3 pages.
GenBank Accession No. NM_002210, Jun. 15, 2008 8 pages.
GenBank Accession No. NM_012238, Apr. 25, 2010. 8 pages.
GenBank Accession No. NM_030593, Mar. 14, 2010. 8 pages.
GenBank Accession No. NP_036370, Apr. 25, 2010. 6 pages.
GenBank Accession No. NP_501912, Nov. 13, 2008. 4 pages.
GenBank Accession No. P53685, Apr. 20, 2010. 8 pages.
Geng et al., "A Specific Antagonist of the p110σ Catalytic Component of Phosphatidylinositol 3'-Kinase, IC486068, Enchances Radiation-Induced Tumor Vascular Destruction", Cancer Res., 64:4893-4899 (2004) 7 pages.
Ginis et al., "Hypoxia affects tumor cell invasiveness in vitro: the role of hypoxia-activated ligand HAL 1/13 (Ku 86 autoantigen)", Cancer Lett., 154:163-174 (2000) 12 pages..
Gladson, C.L., "Expression of integrin α□ β3 in Small Blood Vessels of Giioblastoma Tumors", J. Neurpath. Exp. Neurol., 55(11):1143-1149(1996) 7 pages.
Glinskii et al., "Modification of survival pathway gene expression in human breast cancer cells by tetraiodothyroacetic acid (tetrac)", Cell Cycle, 8(21):3562-3570 (2009) 9 pages.
Glinsky et al., "Classification of Human Breast Cancer Using Gene Expression Profiling as a Component of the Survival Predictor Algorithm", Clin. Cancer Res., 10:2272-2283 (2004) 12 pages.
Glinsky et al., "Gene expression prfiling predicts clinical outcome of prostate cancer", J. Clin. Invest., 113(6):913-923 (2004) 11 pages.
Glinsky et al., "Microarray analysis identifies a death-from-cancer signature predicting therapy failure in patients with multiple types of cancer", J. Clin. Invest., 115(6):1503-1521 (2005) 19 pages.
Glinsky et al., "Microarray Analysis of Xenograft-Derived Cancer Cells Lines Representing Multiple Experimental Models of Human Prostate Cancer", Mol. Carcinog., 37:209-221 (2003) 13 pages.
Goldstein et al., "Influence of Lesion Size and Location on Amphetamine-Facilitated Recovery of Beam-Walking in Rats", Behay. Neurosci., 104(2):320-327 (1990) 9 pages.
Goldstein, A., "Estimating the Error Variance and the Confidence Interval for a Regression Line", in Biostatistics, The MacMillan Co., New York, pp. 139-146 (1964) 10 pages.
Goodman, M.M., "Automated Synthesis of Radiotracers for Pet Applications", in Clinical Positron Emission Tomography, Mosby Yearbook, K.F. Hubner et al., Chapter 14, pp. 110-122 (1992) 13 pages.
Grant, D.B., "Monitoring TSH concentrations during treatment for gongenital hypothyroidism", Arch. Disease Childhood, 66:669-670 (1991) 2 pages.
Gregoriadis, "Liposomes", in Drug Carriers in Biology and Medicine, Chapter 14, pp. 287-341, Academic Press (1979) 57 pages.
Guigon et al., "Regulation of β-Catenin by a Novel Nongenomic Action of Thyroid Hormone β Receptor", Mol. Cell. Biol., 28(14):4598-4608 (2008) 11 pages.
Hahn et al., "Plateau-phase cultures of mammalian cells: An in vitro model for human cancer", Curr. Top. Radiat. Res. Q., 8:39-83 (1972) 45 pages.
Halks-Miller et al., "CCR1 Immunoreactivity in Alzheimer's Disease Brains", Society for Neuroscience Meeting, Abstract #787.6 vol. 24 (1998) Abstract Only. 1 page.
Hansebout, R.R., "A Comprehensive Review of Methods of Improving Cord Recovery After Acute Spinla Cord Injury", in Early Management of Acute Spinal Cord Injusry, pp. 181-196 (1982) 16 pages.
Hashimoto et al., "Matrix Metalloproteinases Cleave Connective Tissue Growth Factor Reactivate Angiogenic Activity of Vascular Endothelial Growth Factor 165", J. Biol. Chem. 277(39):36288-36295 (2002) 8 pages.
Heller et al., "Inhibition of potentially lethal damage recovery by altered pH, glucose utilization and proliferation in plateau growth phase human glioma cells", Int. J. Radiat. Biol., 66(1):41-47 (1994) 7 pages.
Hercbergs et al., "GL261 brain tumor cells: responses to single or fractionated x-irradiation with the α□ β3 integrin tyroxine receptor antagonist tetrac (tetraiodothyroacetic acid)", 20th EORTC-NCI-AACT Symposium on Molecular Targets and Cancer Therapeutics, Geneva, Switzerland, Oct. 2008, 304 pages.
Hercbergs et al., "GL261 brain tumor cells: responses to signle or fractionated x-irradiation with the α□ β3 integrin tyroxine receptor antagonist tetrac (tetraiodothyroacetic acid)", Euro. J. Cancer, 6(12):172 (Abstract Only) 4 pages.
Hercbergs et al., "Propylthiouracil-induced Chemical Hypothyroidism with High-Dose Tamoxifen Prolongs Survival in Recurrent High Grade Ciioma: A Phase I/II Study", Anticancer Res., 23:617-626 (2003) 10 pages.
Hercbergs, A., "The Thyroid Gland as an Intrinsic Biologic Response-Modifier in Advanced Neoplasia—A Novel Paradigm", in vivo, 10:245-247 (1996) 3 pages.
Hercbergs, et al., "Radiosensitization of GL261 glioma cells by tetraiodothyroacetic acid (tetrac)", Cell Cycle, 8 (16):2586-2591 (2009) 6 pages.
Hermanson, "Modification with Synthetic Polymers", in Bioconjugate Tech., Ch. 15, Academic Press, San Diego, CA, pp. 617-618 (1996) 4 pages.
Hoff et al., "Medullary Thyroid Carcinoma", Hematol. Oncol. Cin. North Am., 21(3):475-488 (2007) 14 pages.
Horuk et al., "Expression of Chemokine Receptors by Subsets of Neurons in the Central Nervous System", J. Immunol., 158:2882-2890 (1997) 9 pages.
Hubner, K F., "University of Tennessee Biomedical Imaging Center and Transfer of Technology to the Clinical Floor", in Clinical Positron Emission Tomography, Mosby Yearbook, K.F. Hubner et al., Chapter 2, pp. 4-16(1992) 13 pages.
Hudlicka et al., "Factors involved in capillary growth in the heart", Mol. Cell. Biochem, 147:57-68 (1995) 12 pages.
Igarashi et al., "Techniques Supporting Angiogenesis Therapy 2: DDS Technique Supporting Regenerative Medicine." Inflamm. Immun. 10.6(2002):652-658 7 pages.
Illario et al., "Fibronectin-Induced Proliferation in Thyroid Cells is Mediated by α□ β3 Integrin through Ras/Raf-1/MEK/ERK and Calcium/CaMKII Signals", J. Clin. Endocrinol. Metab., 90(5):2865-2873 (2005) 9 pages.
Ingerman-Wojenski et al., "Evaluation of electrical aggregometry: comparison with optial aggregometry, secretion of ATP, and accumulation of radiolabeled platelets", J. Lab. Clin. Med., 101(1):44-52 (1983) 10 pages.
Iwata et al., "A new, convenient method for the preparation of 4-[18F]fluorobenzyl halides", Applied Radiation and Isotopes, 52(1):87-92 (2000) 7 pages.
Jain, K.K., "Strategies and technologies for drug delivery systems", TIPS, 19:155-157 (1998) 5 pages.
Janssen et al., "Pathogenesis of Spinal Cord Injury and Newer Treatments—A Review", Spine, 14(1):23-32 (1989) 11 pages.
Jeffrey et al., "The preparation and characterisation of poly(lactide-co-glycolide) microparticles. 1. Oil-in-water emulsion solvent evaporation", Int. J. Pharm., 77:169-175 (1991) 7 pages.
Jonker et al., "Cetuximab for the Treatment of Colorectal Cancer", N. Engl. J. Med., 357(20):2040-2048 (2007) 9 pages.
Jordan et al., "Thyroid Status is a Key Modulator of Tumor Oxygenation: Implication for Radiation Therapy", Radiat. Res., 168:428-432 (2007) 5 pages.
Kalofonos et al., "Monoclonal Antibodies in the Management of Solid Tumors", Curr. Top. Med. Chem., 6:1687-1705 (2006) 19 pages.
Kapiszewska et al., "The Effects of Reduced Temperature and/or Starvation Conditions on the Radiosensitivity and Repair of Potentially Lethal Damage and Sublethal Damage in L5178Y-R and L5178Y-S Cells", Radiat. Res., 113:458-472 (1988) 15 pages.
Kastan et al., "A Mammalian Cell Cycle Checkpoint Pathway Utlizing P53 and GADD45 is Defective in Ataxia-Telangiectasia", Cell. 71:587-597 (1992) 11 pages.

(56) References Cited

OTHER PUBLICATIONS

Kawasuji et al., Jap. Circ. J., 63(Suppl. 1):65 (1999) Japanese Abstract Only. 3 pages.

Kerr et al., "Novel Small Molecule αβ Integrin Antagonists: Comparative Anti-Cancer Efficacy with Known Angiogenesis Inhibitors", Anticancer Res., 19:959-968 (1999).

Kerr et al., "Small molecule a integrin antagonists: novel anticancer agents", Exp. Opin. Invest. Drugs, 9 (6):1271-1279 (2000) 9 pages.

Kim et al., "Regulation of Antiogenesis in Vivo, by Ligation of Integrin α5β1 with the Central Cell-Binding Domaing of Fibronectin", Am. J. Pathol., 156(4): 1345-1362 (2000) 18 pages.

Kim et al., "Soluble Flt-1 gene delivery using PEI-g-PEG-RGD conjugate for anti-angiogenesis", J. Control Release, 106:224-234 (2005) 11 pages.

Kimelberg, H.K., "Astrocytic Edema in CNS Trauma", J. Neurotrauma, 9(Suppl. 1):S71-S81 (1992) 12 pages.

Kitevska et al., "Caspase-2: controversial killer or checkpoint controller?", Apoptosis, 14:829-848(2009) 20 pages.

Kleczkowska et al., "Differntial poly(ADP-ribose) metabolism in repair-proficient and repair-deficient murine lymphoma cells", Mut. Res., 235:93-99 (1990) 7 pages.

Klunk et al., "Development of Small Molecule Probes for the Beta-Amyloid Protein of Alzheimer's Disease", Neurobiol. Aging, 15(6):691-698 (1994) 8 pages.

Kobayashi et al., "Drug Delivery Catheter." Surg. Front. 9.1(2002):55-57 3 pages.

Konno et al., "Antiogenetic therapy for carcinoma", Igaku No Ayumi, 194(10): 824-828 (2000) 5 pages.

Koutras et al., "Antiproliferative effect of exemestane in lung cancer cells", Mol. Cancer, 8(1):109 (2009) 12 pages.

Koyama et al., "Recent Status and Future Perspectives in Therapeutic Angiogenesis", Prog. Med., 22(12):3070-3076 (2002) (English Abstract) 7 pages.

Kramer et al., "Human Microvascular Endothelial Cells Use β1 and β3 Integrin Receptor Complexes to Attach to Laminin", J. Cell Biol., 111:1233-1343 (1990) 11 pages.

Kumar et al., "Enhancing Effect of Thyroxine on Tumor Growth and Metastases in Syngeneic Mouse Tumor Systems", Cancer Res., 39:3515-3518 (1979) 4 pages.

Kuroki et al., "Diabetic retinopathy—The mechanisms of the ocular neovascularization of the development of anti-angiogenic drugs-", Nippon Rinsho, 57(3):584-589 (1999) (English Abstract Only) 6 pages.

Kwok et al., "Differences in EGF rated radiosensitisation of human squamous carcinoma cells with high and low numbers of EGF receptors", Br. J. Cancer, 64:251-254 (1991) 4 pages.

Lameloise et al., "Differences between the effects of thyroxine and tetraiodothyroacetic acid on TSh suppression and cardiac hypertrophy", Eur. J. Endocrinol., 144:145-154 (2001) 10 pages.

Lawler et al., "Cell Attachment to Thombospondin: The Role of ARG-GLY-ASP, Calcium and Integrn Receptors", J. Cell Biol., 107(6 Pt. 1): 2351-2361 (1988) 11 pages.

Letterio et al., "Maternal Rescue of Transforming Growth Facotr-β1 Null Mice", Science, 264:1936-1938 (1994) 4 pages.

Li et al., "Requirement of hypoxia-inducible factor-1α down-regulation in mediating the antitumor activity of the anitgrowth factor receptor monoclonal antibody cetuximab", Mol. Cancer Ther., 7(5):1207-1217 (2008) 11 pages.

Lin et al., "Androgen-induced human breast cancer cell proliferation is mediated by discrete mechanisms in estrogen receptor-α-positive and -negative breast cancer cells", J. Steroid Biochem. Mol. Biol., 113:182-188 (2009) 7 pages.

Lin et al., "Identification of the Putative Map Kinase Docking Site in the Thyroid Hormone Receptor-β DNA-Binding Domain: Functional Consequences of Mutations at the Docking Site", Biochem., 42:7571-7579 (2003) 9 pages.

Lin et al., "Integrin αβ β3 contains a receptor site for resveratrol", FASEB J., 20(10): 1742-1744 (2006) 3 pages.

Lin et al., "L-Thyroxine vs. 3,5,3'-triiodo-L-thyronine and cell proliferation: activation of mitogen-activated protein kinase and phosphatidylinositol 3-kinase", Am. J. Physiol. Cell Physiol., 296:C980-C991 (2009) 12 pages.

Lin et al., "Resveratrol Causes COX-2- and p53-Dependent Apoptosis in Head and Neck Squamos Cell Cancer Cells", J. Cell Biochem., 104:2131-2142 (2008) 12 pages.

Lin et al., "Resveratrol Induced Serine Phosphorylation of p53 Causes Apoptosis in a Mutant p53 Prostate Cancer Cell Line", J. Urol., 168:748-755 (2002) 8 pages.

Lin et al., "Resveratrol is pro-apoptotic and thyroid hormone is anti-apoptotic in glioma cells: both actions are integrin and ERK mediated", Carcinogenesis, 29(1):62-69 (2008) 8 pages.

Lin et al., "The pro-apoptotic action of stilbene-induced COX-2 in cancer cells: Convergence with the anti-apoptotic effect of thyroid hormone", Cell Cycle, 8(12):1877-1882 (2009) 6 pages.

Lin et al., "Thyroid hormone is a MAPK-dependent growth factor for thyroid cancer cells and is anti-apoptotic", Steriods, 72:180-187 (2007) 8 pages.

Liu et al., "Calcineurin is a Common Target of Cyclophilin-Cyclosporin a and FKBP-FK506 Complexes", Cell, 66:807-815 (1991) 9 pages.

Lorger et al., "Activation of tumor cell integrin αβ β3 controls angiogenesis and metastatic growth in the brain", Proc. Natl. Acad. Sci. U.S.A., 106(26):10666-10671 (2009) 7 pages.

Louie et al., "Pharmacodynamics of Levofloxacin in a Murine Pneumonia Model of Pseudomonas aeruginosa Infection: Determination of Epithelial Lining Fluid Targets", Antimicrob Agents Chemother., 53(8):3325-3330 (2009) 6 pages.

Luidens et al., "Thyroid hormone and angiogenesis", Vascular Pharmacology, 52(3-4):142 (2010) 4 pages.

Lyons et al., "The Expression of an N-CAM Serum Fragment is Positively Correlated with Severity of Negative Featues in Type II Schizophrenia", Biol. Psychiatry, 23:769-775 (1988) 7 pages.

Ma, et al., "Use of Encapsulated Single Chain Antibodies for Induction of Anti-Idiotypic Humoral and Cellular Immune Responses", J. Pharm. Sci., 87(1375-1378 (1998) 4 pages.

Mahmood et al., "An N2S2 Teradentate Chelate for Solid-Phase Synthesis: Evaluation in Solution and Solid Phase and Characterization of Technetium-99 Complexes", Technetium, Rhenium and Other Metals in Chemistry and Nuclear Medicine, 5:71-76 (1999) 6 pages.

Mandelin et al., "Extracellular and Intracellular Mechanisms That Mediate the Metastatic Activity of Exogenous Osteopontin", Cancer, 115:1752-1764 (2009) 12 pages.

Mangale et al., "Identification of genes regulated by an interaction between αβ β3 integrin and vitronectin in murine decidua", Reprod. Fertil. Dev., 20:311-319 (2008) 10 pages.

Markgraf et al., "Sensorimotor and cognitive consequences of middle cerebral artery occlusion in rates", Brain Res., 575(2):238-246 (1992) 10 pages.

Martens et al., "Inhibition of Glioblastoma Growth in a Highly Invasive Nude Mouse Model Can Be Achieved by Targeting Epidermal Growth Factor Receptor but not Vasculap Endothelial Growth Factor Receptor-2", Clin. Cancer Res., 14(17):5447-5458 (2008) 12 pages.

Masson-Gadais et al., "Integrin αβ β3 requirement for VEGFR2-mediated activation of SAPK2/p38 and Hsp90-dependent phosphorylation of focal adhesion kinase in endothelial cells activated by VEGF", Cell Stress Chaperones, 8(1):37-52 (2003) 16 pages.

McCarty et al., "Promises and Pitfalls of Anti-Angiogenic Therapy in Clinical Trials." Trends Mol. Med. 9.2(2003):53-58 6 pages.

Meneses et al., "Recombinant angiostatin prevents retinal neovascularization in a murine proliferative retinopathy model", Gene Therapy, 8(8):646-648 (2011) 3 pages.

Mezosi et al., "Nongenomic effect of thyroid hormone on free-radical production in human polymorphonuclear leukocytes", J. Endocrinol., 185:121-129 (2005) 9 pages.

Mishkin et al., "Increased Survival of Rats Bearing Morris Hepatoma 7800 after Induction of Hypothroidism", Cancer Res., 39:2471-2375 (1979) 5 pages.

(56) References Cited

OTHER PUBLICATIONS

Miyaguchi et al., "Correlation of Epidermal Growth Factor Receptor and Radiosensitivity in Human Maxillary Carcinoma Cell Lines", ActaOtolaryngol., 118:428-431 (1998) 4 pages.

Moeller et al., "Cytosolic Action of Thyroid Hormone Leads to Induction of Hypoxia-inducible Factor-1α and Glycolytic Genes", Molec. Endo., 19(12):2955-2963 (2005) 9 pages.

Moeller et al., "Thyroid hormone mediated changes in gene expression can be initiated by cytosolic action of the thyroid hormone receptor beta through the phosphatidylinositol 3-kinase pathway", Nuclear Receptor Signaling, 4:E020 (2006) 4 pages.

Mohamed et al., "Wound healing properties of cimetidine in vitro", Drug Intel!. Clin. Pharm., 20(12):973-975 (1986) 4 pages.

Monferran et al., "α□ β3 and α□ β5 integrins control glioma cell response to ionising radiation through ILK and RhoB", Int. J. Cancer, 123:357-364 (2008) 8 pages.

Morand et al., "Effect of Iodide on Nicotinamide Adenine Dinucleotide Phosphate Oxidase Activity and Duox2 Protein Expression in Isolated Porcine Thyroid Follicles", Endo., 144(4):1241-1248 (2003) 8 pages.

Moreno et al., "Metabolic Effects of Thyroid Hormone Derivative", Thyroid, 18(2):239-253 (2008) 15 pages.

Moreno et al., "Thyroid Economy—Regulation, Cell Biology, Thyroid Hormone Metabolism and Action: The Special Edition: Metabolic Effects of Thyroid Hormones. Metabolic Effects of Thyroid Hormone Derivatives", Thyroid, 18 (2):239-253 (2008) 15 pages.

Mousa et al., "Cellular and Molecular Mechanisms of Nicotine's Pro-Angiogenesis Activity and Its Potential Impact on Cancer", J. Cell. Biochem., 97:1370-1378 (2006) 9 pages.

Mousa et al., "Discovery of Pro-Angiogenic Effects of Nicotine's Pro-Angiogenesis Activity and Its Potential Impact on Cancer", J. Cell. Biochem., 97:1370-1378 (2006) Abstract Only. 3 pages.

Mousa et al., "Proangiogenesis Action of the Thyroid Hormone Analog 3,5-Diiodothyropropionic Acid (DITPA) Is Initiated at the Cell Surface and is Integrin Mediated", Endocrinol., 147(4):1602-1607 (2006) 6 pages.

Mousa et al., "Pro-angiogenesis action of thyroid hormone and analogs in a three-dimensional in vitro microvascular endothelial sprouting model", Int. Angiol., 25(4):407-413 (2006) 7 pages.

Mousa et al., "Tetraiodothyroacetic (tetrac) inhibits angiogenesis", In: Program of the 77th Annual Meeting of the American Thyroid Association, Phoenix, AZ, 2006: Abstract 108. 4 pages.

Mousa et al., "Tetraiodothyroacetic acid, a small molecule integrin ligand, blocks angiogenesis induced by vascular endothelial growth factor and basic fibroblast growth factor", Angiogenesis, 11:183-190 (2008) 8 pages.

Mousa et al., "The Proangiogenic Action of Thyroid Hormone Analogue GC-1 Is Initiated at an Integrin", J. Cardiovasc. Pharmacol., 46(3):356-360 (2005) 6 pages.

Mousa, S.A., "Mechanisms of Angiogenesis: Potential Therapeutic Targets", in Angiogenesis Inhibotors and Stimulators: Potential Therapeutic Implications, Landes Bioscience, Georgetown, Texas, Chapter I, pp. 1-12 (2000) 14 pages.

Mousa, S.A., et al., "Effect of Resveratrol on Angiogenesis and Platelet/Fibrin-Accelerated Tumor Growth in the Chick Chorioallantoic Membrane Model," Nutr. Cancer, 52(1):59-65 (2005) 7 pages.

Muller et al., "The Double Life of the Ku Protein: Facing the DNA Breaks and the Extracellular Environment", Cell Cycle, 4(30:438-441 (2005) 4 pages.

Ndiaye et al., "Red wine polyphenol-induced, endothelium-dependent NO-mediated relaxation is due to the redox-sensitive P13-kinase / Akt-dependent phosphorylation of endothelial NO-synthase in the isolated porcine coronary artery", FASEB J., 19(3):455-457 (2005) 3 pages.

Nehls et al., "A microcarrier-based concultivation system for the investigation of factors and cells involved in angiogenesis in three-dimensional fibrin matrices in vitro", Histochem. Cell Biol., 104(6):459-466 (1995) 8 pages.

Nehls et al., "A Novel Micrcarrier-Based in Vitro Assay for Rapid and Reliable Quantification of Three-Domensional Cell Migration and Angiogenesis", Microvasc. Res., 50(3):311-322 (1995) 12 pages.

Neises et al., "Esterification of Carboxylic Acids with Dicyclohexylcarbodiimide/4-Dimethylaminopyridine: tert-Butyl Ethyl Fumarate", Org. Synth., 7:93 (1990); 63:183 (1985) 3 pages.

Newcomb et al., "Radiation Sensitivity of GL261 Murine Glioma Model and Enhanced Radiation Response by Flavopiridol", Cell Cycle., 5(1):93-99 (2006) 7 pages.

Nickoloff et al., "Aberrant Production of Interleukin-8 and Thrombospondin-1 by Psoriatic Keratinocytes Mediates Angiogenesis." Am. J. Pathol. 144.4(1994):820-828 9 pages.

Nilsson et al., "Evidence for Multiple Thyroxine-binding Sites in Human Prealbumin", J. Biol. Chem., 246(19): 6098-6105 (1971) 8 pages.

Ning et al., "Anti-integrin monoclonal antibody CNTO 95 enhances the therapeutic efficacy of fractionated radiation therapy in vivo", Mol. Cancer Ther., 7(6):1569-1578 (2008) 10 pages.

Oak et al., "Antiangiogenic properties of natural polyphenols from red wine and green tea", J. Nutr. Biochem., 16:1-8 (2005) 8 pages.

Okada et al., "A Quantitative in vivo Method of Analyzing Human Tumor-induced Angiogenesis in Mice Using Agarose Microencapsulation and Hemoglobin Enzyme-linked Immunosorbent Assay", Jpn. J. Cancer Res., 86(12):1182-1188 (1995) 7 pages.

Pages et al., "Signaling Angiogenesis via p42/p44 MAP Kinase Cascade", Ann. N.Y. Acad., Sci., 902:187-200 (2000) 14 pages.

Painter et al., "Membrane initiation of DNA synthesis", Nature, 270:543 (1977) 1 page.

Panter et al., "Pretreatment with Nmda antagonists limits release of excitatory amino acids following traumatic brain injury", Neurosci. Lett., 136(2):165-168 (1992) 4 pages.

Panyam, et al., "Biodegradable nanoparticles for drug and gene delivery to cells and tissues", Advanced Drug Delivery Reviews, 55: 329-347 (2009) 19 pages.

Pardridge, W.M., "Receptor-Mediated Peptide Transport through the Blood-Brain Barrier", Endocrine Rev., 7 (3):314-330 (1986) 18 pages.

Park et al., "Effects of Tetramethoxystilbene on Hormone-Resistant Breast Cancer Cells: Biological and Biochemical Mechanisms of Action", Cancer Res., 67:5717-5726 (2007) 10 pages.

Parveen, et al., "Polymeric nanoparticles for cancer therapy", Journal of Drug Targeting, 16(2): 108-123, Feb. 2008. 16 pages.

Patel, D.K., "Clinical Use of Anti-Epidermal Growth Factor Receptor Monoclonal Antibodies in Metastatic Colorectal Cancer", Pharacotherapy, 28(11 Pt.2):31S-41S (2008) 12 pages.

Penno et al., "Rapid and quantitative in vitro measurement of cellular chemotaxis and invasion", Meth. Cell Sci., 19:189-195 (1997) 7 pages.

Pirola, et al., "Resveratrol: One Molecule, Many Targets", IUBMB Life, vol. 60, Issue 5, pp. 323-332. 10 pages.

Plow et al., "Ligand Binding to Integrins", J. Biol. Chem., 275(29):21785-21788 (2000) 4 pages.

Powell, J., "The Serial Analysis of Gene Expression", in Meth. Mol. Biol., Chapter 20, 99:297-319 (2000) 23 pages.

Prichard et al., "Concurrent Cetuximab and Bevacizumab Therapy in a Murine Orthotopic Model of Anaplastic Thyroid Carcinoma", Laryngoscope, 117:674-679 (2007) 7 pages.

Pujol et al., "Letter to the editors: Preventioon of thyroid neoplasm recurrence with Triac and levothyroxine", Clin. Endocrinol., 46(1):121-122 (1997) 2 pages.

Raue et al., "Multiple Endocrine Neoplasia Type 2", Horm. Res., 68(Suppl.5): 101-104 (2007) 4 pages..

Rayalam et al., "Resveratrol induces apoptosis and inhibits adipogenesis in 3T3-L1 adipocytes", Phytother. Res., 22:1367-1371 (2008) 5 pages.

Rebbaa et al., "Novel function of the thyroid hormone analog tetraiodothyroacetic acide: a cancer chemosensitizing and anti-cancer agent", Angiogenesis, 11(3):269-276 (2008) 8 pages.

Reinholt et al., "Osteopontin—a possible anchor of osteoclasts to bone", Proc. Natl. Acad. Sci. U.S.A., 87:4473-4475 (1990) 3 pages.

(56) References Cited

OTHER PUBLICATIONS

Remsen et al., "Antibodies to the Neural Cell Adhesion Molecule Disrupt Functional Recovery in Injured Nerves", Exp. Neurol., 110:268-273 (1990) 6 pages.
Ren et al., "Regulation of tumor angiogenesis by thrombospondin-1", Biochim. Biophys. Acta. 1765: 178-188 (2006) 11 pages.
Risau, W., "Mechanisims of angiogenesis", Nature, 386:671-674 (1997) 4 pages.
Sahni et al., "Stimulation of endothelial cell proliferation by FGF-2 in the presence of fibrinogen requires $\alpha\square$ $\beta3$", Blood, 104(12):3635-3641 (2004) 7 pages.
Saito et al., "Vector-mediated delivery of 125I-labeled β-amyloid peptide Aβ1-40 through the blood-brain barrier and binding to Alzheimer disease of the Aβ-40/vector complex", Proc. Natl. Acad. Sci. US, 92:10227-10231 (1995) 5 pages.
Samuels et al., "Depletion of L-3-5-3'-Triiodothyronine and L-Thyroxine in Euthyroid Calf Serum for Use in Cell Culture Studies of the Action of Thyroid Hormone", Endo., 105(1):80-85 (1979) 6 pages.
SAS/STAT Guide for Personal Computers, Version 6 Edition, p. 717 (1987) 3 pages.
Sato et al., "Neovascularization: General Remarks", Biotherapy, 15(6):631-636 (2001) (English Abstract) 6 pages.
Scanlan et al., "3-Iodothyronamine is an endogenous and rapid-acting derivative of thyroid hormone", Nat. Med., 10 (6):638-642 (2004) 5 pages.
Scanlan et al., "Selective thyrmimetics: Tissue-selective thyroid hormone analogs", Curr. Opin. Drug Discov. Dev., 4(5):614-622 (2001) 9 pages.
Schlange et al., "Autocrine Wnt signaling contributes to breast cancer cell proliferation via the canonical WNT pathway and EGFR transactivation", Breast Cancer Res., 9:R63 (2007) 15 pages.
Schlumberger et al., "New therapeutic approaches to treat medullary thyroid carcinoma", Nat. Clin. Prac. Endocrinol. Metab., 4(10):22-32 (2008) 11 pages.
Schnell et al., "Expression of alpha v beta 3 integrin in patients with high and low grade glioma", Proc. Amer. Assoc. Cancer Res., 47:226 (2006) Abstract Only. 5 pages.
Schnell et al., "Expression of Integrin $\alpha\square$ $\beta3$ in Gliomas Correlates with Tumor Grade and Is not Restricted to Tumor Vasculature", Brain Pathol., 18:378-386 (2008) 9 pages.
Schreiber et al., "Hormone delivery systems to the brain-transhyretin", Exp. Clin. Endocrinol Diabetes, 103(2): 75-80 (1995) 7 pages.
Schueneman et al., "SU11248 Maintenance Therapy Prevents Tumor Regrowth after Fractionated Irradiation of Murine Tumor Models", Cancer Res., 63:4009-4016 (2003) 8 pages.
Shih et al., "Thyroid Hormone Promotes Serine Phosphorylation of p53 by Mitogen-Activated Protein Kinase", Biochem., 40:2870-2878 (2001) 10 pages.
Shih et al., "Disparate Effects of Thyroid Hormone on Actions of Epidermal Growth Factor and Transforming Growth Factor-α Are Mediated by 3.5'-Cyclic Adenosine 5'-Monophosphate-Dependent Protein Kinase II", Endo., 144(4):1708-1717 (2004) 10 pages.
Shih et al., "Inhibitory effect of epidermal growth factor on resveratrol-induced apoptosis in prostate cancer cells is mediated by protein kinase C-α", Mol. cancer Ther., 3:1355-1363 (2004) 9 page.
Shinohara et al., "Enhanced radiation damage of tumor vasculature by mTOR inhibitors", Oncogene, 24:5414-5422 (2005), 9 pages.
Skrovronsky et al., "In vivo detection of amyloid plaques in a mouse model of Alzheimer's disease", Proc. Natl. Acad. Sci US, 97(13):7609-7614 (2000) 6 pages.
Skuli et al., "$\alpha\square$ $\beta3/\alpha\square$ $\beta5$ integrins-FAK-RhoB: A Novel Pathway for Hypoxia Regulation in Glioblastoma", Cancer Res., 69*8):3308-3316 (2009) 9 pages.
Song et al., "Formulation and characterization of biodegradable nanoparticles for intravascular local drug delivery", J. Controlled Rel., 43:197-212 (1997) 16 pages.
Stefani et al., "The Effect of Resveratrol on a Cell Model of Human Aging", Ann. NY Acad. Sci., 1114:407-418 (2007) 12 pages.

Strieth, et al., "Antiangiogenic combination tumor therapy blocking $\alpha\square$ -integrins and VEGF-receptor-2 increases therapeutic effects in vivo", Int. J. Cancer, 119:423-431 (2006) 9 pages.
Sumi et al., "Wound healing using regenerative medicine", Surg. Front., 10(2):162-165 (2003) 4 pages.
Sunwoo et al., "Novel Proteasome Inhibitor PS-341 Inhibits Activation of Nuclear Factor-κB, Cell Survival, Tumor Growth, and Angiogenesis in Squamous Cell Carcinoma", Clin. Cancer Res., 7:1419-1428 (2001) 10 pages.
Szatmari et al., "Detailed characterization of the mouse glioma 261 tumor model for experimental glioblastoma therapy", Cancer Sci., 97(6):546-553 (2006) 8 pages.
Szumiel, I., "Ca2+, Mg2+ and (Adenosine Diphosphate Ribose)n. In Cellular Response to Irradiation", J. Theor. Biol., 101:441-451 (1983) 11 pages.
Takemaru et al., "Chibby, a nuclear β-catenin-associated antagonist of the Wnt/Wingless pathway", Nature, 422:905-909 (2003) 5 pages.
Tanaka et al., J. Soc. Gastroenterological Surgery, 27(2):360 (1996) 3 pages.
Tang et al., "Resveratrol-induced Cyclooxygenase-2 facilitates p53-dependent apoptosis in human breast cancer cells", Mol. Cancer Ther., 5(8):2034-2042 (2006) 9 pages.
Tang et al., "Thyroid Hormone Causes Mitogen-Activated Protein Kinase-Dependent Phosphorylation of the Nuclear Estrogen Receptor", Endocrinol., 145(7):3265-3272 (2004) 8 pages.
Tator et al., "Review of the secondary injury theory of acute spinal cord trauma with emphasis on vascular mechanisms", J. Neurosurg., 75(1):15-26 (1991) 13 pages.
Theodossiou et al., "Propylthiouracil-induced Hypothyroidism Reduces Xenograft Tumor Growth in Athymic Nude Mice", Cancer, 86:1596-1601 (1999) 6 pages.
Thompson et al., "The Clinical Manipulation of Angiogenesis: Pathology, Side-Effects, Surprises, and Opportunites with Novel Human Therapies." J. Pathol. 190(2000):330-337 8 pages.
Thraves et al., "Radiosensitization of Human Fibroblasts by 3-Aminobenzamide: An Inhibitor of Poly(ADP-Ribosylation)", Radiat Res., 104:119-127 (1985) 9 pages.
Tol et al., "Chemotherapy, Bevacizumab, and Cetuximab in Metastatic Colorectal Cancer", N. Engl. J. Med., 360 (6):563-572 (2009) 10 pages.
Tomanek et al., "A Thyroid Hormone Analog Stimulates Angiogenesis in the Post-infarcted Rat Heart", J. Mol. Cell Cardiol., 30(5):923-932 (1998) 10 pages.
Tomanek et al., "Angiogenesis: New Insights and Therapeutic Potential", Anatomical Record (New Anat.), 261:126-135 (2000) 10 pages.
Tomanek et al., "Early Coronary Angiogenesis in Resposne to Thyroxine: Growth Characteristics and Upregulation of Basic Fibroblast Growth Factor", Circ. Res., 82(5):587-593 (1998) 8 pages.
Tomanek et al., "Growth of the Coronary Vasculature in Hypertrophy: Mechanisms and Model Dependence", Cell. Mol. Bio. Res., 40(2):129-136 (1994) 8 pages.
Toms et al., "Thyroid Hormone Depletion Inhibits Astrocytoma Proliferation via a p53-Independent Induction of p21 (WAF/1CIP1)", Anticancer Res., 18:289-293 (1998) 5 pages.
Tuttle et al., "Recombinant Human TSH-Assisted Radioactive Iodine Remnant Ablation Achieves Short-Term Clinical Recurrance Rates Similar to Those of Traditional Thyroid Hormone Withdrawal", J. Nucl. Med., 49(5):764-770 (2008) 7 pages.
Tzirogiannis et al., "Enhanced Proliferation of Human Lung Adenocarcinoma and Small Cell Lung Carcinoma Cells Directed from the Cell Surface by Thyroid Hormone", in 89th Annual Meeting. The Endocrine Society (2007) Abstract Only 3 pages.
Utsumi et al., "Potentially Lethal Damage Versus Sublethal Damage: Independent Repair Processes in Actively Growing Chinese Hamster Cells", Radiat. Res., 77:346-360 (1979) 9 pages.
Van Waes et al., "Effects of the novel $\alpha\square$ integrin antagonist SM256 and cis-platinum on growth of murine squamos cell carcinoma PAM LY8", Int. J. Oncol., 16(6):1189-1195 (2000) 8 pages.
VanCutsem et al., "Cetuximab and Chemotherapy as Initial Treatment for Metastatic Colorectal Cancer", N. Engl. J. Med., 360:1408-1417 (2009) 10 pages.
Varnes et al., "The Effect of pH on Potentially Lethal Damage Recovery in A549 Cells", Radiat. Res., 108:80-90 (1986) 11 pages.

(56) References Cited

OTHER PUBLICATIONS

Velasco et al., "Dermatological Aspects of Angiogenesis." Brit. J. Dermatol. 147(2002):841-852 12 pages.
Wang et al., "DITPA stimulated bFGF, VEGF, angiopoietin, and Tie-2 and facilates coronary arteriolar growth", Am. J. Physiol. Heart Circ. Physiol., 284(2):H613-H618 (2003) 6 pages.
Wang et al., "Integrin-associated Protein Stimulates α2β1-dependent Chemotaxis via Gi-mediated inhibition of Adenylate Cyclase and Extracelular-regulated Kinases", J. Cell. Biol., 147:389-399 (1999) 11 pages.
Wen et al., "Prognostic Value of EGFR and TGF-α in Early Laryngeal Cancer Treated With Radiotherapy", Laryngoscope, 106(7):884-888 (1996) 6 pages.
Werdelin et al., "Neuropeptides and neural cell adhesion molecule (NCAM) in CSF from patients with ALS", Acta Neurol. Scand., 79(3):177-181 (1989).
Wilkinson, J.H., "Synthesis of some Possible Metabolites of Thyroxine and Triiodothyronine", Biochem. J., 63:601-605 (1956) 5 pages.
Xia et al., "Chemokines/chemokine receptors in the central nervous system and Alzheimer's disease", J. NeuroVirol., 5:32-41 (1999) 11 pages.
Yalcin et al., "Tetraidothyroacetic Acid (Tetrac) and Tetrac Nanoparticles Inhibit Growth of Human Renal Cell Carcinoma Xenografts", Anticancer Res., 29:3825-3832 (2009) 7 pages.
Yalcin et al., "Tetraiodothyroacetic Acid (Tetrac) and Nanoparticulate Tetrac Arrest Growth of Medullary Carcinoma of the Thyroid", J. Clin. Endocrinol. Metab., 95(4):1972-1980 (2010) 7 pages.
Yalcin et al., "Tetraiodothyroacetic Acid (Tetrac) and Nanoparticulate Tetrac Arrest Growth of Medullary Carcinoma of the Thyroid", J. Clin. Endocrinol. Metab., 95(4):1972-1980 (2010) 9 pages.
Yalcin et al., "Tetraiodothyroacetic Acid and Tetraiodothyroacetic Acid Nanoparticle Effectively Inhibit the Growth of Human Follicular Thyroid Cell Carcinoma", Thyroid, 20(3):281-286 (2010) 6 pages.
Yanase et al., "Role of N-methyl-D-aspartate receptor in acute spinal cord injury", J. Neurosurg., 83:884-888 (1995) 6 pages.
Yang et al., "Rab7b, a novel lysosome-associated small GTPase, is involved in monocytic differentiation of human acute promyelocytic leukemia cells", Biochem. Biophys. Res. Commun., 318:792-799 (2004) 8 pages.
Yang, et al., "Enhanced inhibition of adipogenesis and induction of apoptosis in 3T3-L1 adipocytes with combinations of resveratrol and quercetin", Life Sci., 82:1032-1039 (2008) 8 pages.
Yonkers et al., "Sensory Neuron Sodium Current Requires Nongenomic Actions of Thyroid Hormone During Development", J. Neurophysiol., 100:2719-2725 (2008) 7 pages.
Young, W., "Role of Calcium in Central Nervous System Injuries", J. Neurotrauma, 9(Suppl. 1): S9-S25 (1992) 18 pages.
Young, W., "Secondary injury mechanisms in acute spinal cord injury", J. Emerg. Med., 11:13-22 (1993) 11 pages.
Yu et al., "Osteopontin Gene is Expressed in the Dermal Papilla of Pelage Follicles in a Hair-Cycle-Dependent Manner", J. Invest. Dermatol., 117:1554-1558 (2001) 5 pages.
Yu, et al., "The Compressor Silencing Mediator for Retinoid and Thyroid Hormone Receptor Facilitates Cellular Recovery from DNA Double-Strand Breaks", Cancer Res., 66(18):9316-9322 (2006) 7 pages.
Zhang et al., "Oestrogen inhibits resveratrol-induced post-translational modification of p53 and apoptosis in breast cancer cells", Br. J. Cancer, 91:178-185 (2004) 8 pages.
Zhang et al., "Quantitative PET Imaging of Tumor Integrin αvβ3 Expression with 18F-FRGD2", J. Nucl. Med., 47:113-121 (2006) 9 pages.
Zhen et al., "Synthesis and Amyloid Binding Properties of Rhenium Complexes: Preliminary Progress Toward a Reagent for SPECT Imaging of Alzheimer's Disease Brain", J. Med. Chem., 42:2805-2815 (1999) 11 pages.
Zhuang et al., "99mTc-Labeled MIBG Derivatives: Novel 99m Tc Complexes as Myocardial Imaging Agents for Sympathetic Neurons", Bioconjugate Chem., 10:159-168 (1999) 10 pages.
Office Action (Mail Date Apr. 11, 2013) for U.S. Appl. No. 12/816,287, filed Jun. 15, 2010.
Office Action (Mail Date Apr. 8, 2013) for U.S. Appl. No. 11/786,723, filed Apr. 11, 2007.
Office Action (Mail Date Apr. 12, 2013) for U.S. Appl. No. 12/751,375, filed Mar. 31, 2010.
Office Action (Mail Date Apr. 29, 2013) for U.S. Appl. No. 13/345,194, filed Jan. 6, 2012.
Office Action (Mail Date Oct. 24, 2013) for U.S. Appl. No. 12/816,287, filed Jun. 15, 2010.
Notice of Allowance (Mail Date Oct. 4, 2013) for U.S. Appl. No. 11/786,723, filed Apr. 11, 2007.
Office Action (Mail Date Oct. 15, 2013) for U.S. Appl. No. 13/345,194, filed Jan. 6, 2012.
Office Action (Mail Date Apr. 2, 2013) for U.S. Appl. No. 13/156,047, filed Jun. 8, 2011.
Office Action (Mail Date Feb. 25, 2014) for U.S. Appl. No. 13/156,047, filed Jun. 8, 2011.
U.S. Appl. No. 14/184,889, filed Feb. 20, 2014; Confirmation No. 3033; Customer No. 5409.
U.S. Appl. No. 14/185,010, filed Feb. 20, 2014; Confirmation No. 4595; Customer No. 5409.
U.S. Appl. No. 13/975,725, filed Aug. 26, 2013; Confirmation No. 7136; Customer No. 5409.
U.S. Appl. No. 12/751,375, filed Mar. 31, 2010; Confirmation No. 1512; Customer No. 5409.
U.S. Appl. No. 13/345,194, filed Jan. 6, 2012; Confirmation No. 5479; Customer No. 5409.
U.S. Appl. No. 13/156,047, filed Jun. 8, 2011; Confirmation No. 4235; Customer No. 5409.
U.S. Appl. No. 12/644,493, filed Dec. 22, 2009; Confirmation No. 6460; Customer No. 5409.
U.S. Appl. No. 11/786,723, filed Apr. 11, 2007; Confirmation No. 2124; Customer No. 5409.
U.S. Appl. No. 12/816,287, filed Jun. 15, 2010; Confirmation No. 2994; Customer No. 5409.
U.S. Appl. No. 12/947,389, filed Nov. 16, 2010; Confirmation No. 1791; Customer No. 5409.
Office Action (Mail Date Feb. 25, 2014) for U.S. Appl. No. 13/156,147, filed Jun. 8, 2011.
Office Action (Mail Date Mar. 12, 2014) for U.S. Appl. No. 12/947,389, filed Nov. 16, 2010.
Notice of Allowance (Mail Date Feb. 6, 2014) for U.S. Appl. No. 13/345,194, filed Jan. 6, 2012.
Avgoustakis, et al., "PLGA-mPEG nanoparticles of cisplatin: in vitro nonoparticles degradation, in vitro drug release and in vivo drug residence in blood properties" J. Contr. Rel. 2002, 79, 123-135, 13 pages.
Office Action (Mail Date Sep. 4, 2014) for U.S. Appl. No. 12/947,389, filed Nov. 16, 2010.
Office Action (Mail Date May 8, 2014) for U.S. Appl. No. 12/816,287, filed Jun. 15, 2010.
Office Action (Mail Date Jul. 13, 2012) for U.S. Appl. No. 12/751,375, filed Mar. 31, 2010.
Office Action (Mail Date May 23, 2012) for U.S. Appl. No. 12/816,287, filed Jun. 15, 2010.
Office Action (Mail Date Oct. 16, 2014) for U.S. Appl. No. 12/644,493, filed Dec. 22, 2009.
Surks, Martin I. et al. "Subclinical Thyroid Disease; Scientific Review and Guidelines for Diagnosis and Management." Journal of the American Medical Association, Jan. 14, 2004, vol. 291, No. 2, pp. 228-238; especially p. 230-231.
NCI Cancer Drug Information, Cetuximab, 2006,http://www.cancergovicancertopics/druginfo/cetuxinnab,downloaded Jul. 18, 2014.
Gu et al. 2007, Nanotoday 2:14-21.
J Wood, K Bonjean, S Ruetz, A Bellahcene, L Devy, JM Foidart, V Castronovo, JR Green. "Novel Antiangiogenic Effects of the u

(56) References Cited

OTHER PUBLICATIONS

Bisphosphonate Compound Zoledronic Acid." The Journal of Pharmacology and Experimental Therapeutics, vol. 302, No. 3, 2002, pp. 1 055-1 061.

M Yalcin, DJ Bharali, L Lansing, E Dyskin, SS Mousa, A Hercbergs, FB Davis, PJ Davis, SA Mousa."Tetraidothyroacetic Acid v (Tetrac) and Tetrac Nanoparticles Inhibit Growth of Human Renal Cell Carcinoma Xenografts." Anticancer Research, vol. 29, 2009, pp. 3825-3832.

Office Action (Mail Date Jun. 21, 2011) for U.S. Appl. No. 12/947,389, filed Nov. 16, 2010.

Office Action (Mail Date Apr. 4, 2012) for U.S. Appl. No.. 12/947,389, filed Nov. 16, 2010.

Office Action (Mail Date Oct. 17, 2012) for U.S. Appl. No. 12/947,389, filed Nov. 16, 2010.

Office Action (Mail Date Apr. 4, 2014) for U.S. Appl. No. 12/947,389, filed Nov. 16, 2010.

Notice of Allowance (Mail Date May 12, 2015) for U.S. Appl. No. 12/816,287.

Office Action (Mail Date Oct. 5, 2012) for U.S. Appl. No. 12/644,493, filed Dec. 22, 2009.

Office Action (Mail Date Apr. 16, 2015) for U.S. Appl. No. 13/156,047, filed Jun. 8, 2011.

Office Action (Mail Date Jan. 12, 2015) for U.S. Appl. No. 12/751,375, filed Mar. 31, 2010.

Office Action (Mail Date Jun. 3, 2015) for U.S. Appl. No. 12/751,375, filed Mar. 31, 2010.

Office Action (Mail Date Oct. 14, 2014) for U.S. Appl. No. 14/242,041, filed Apr. 1, 2014.

Application No. PCT/US2010/038700, Supplemental European Search Report dated Apr. 20, 2015. 7 pages.

T4 and T3 stimulate angiogenesis in the chorioallantoic membrane model

| Treatment | Angiogenesis Index |
|---|---|
| PBS | 63 ± 10 |
| T3 (1 nM) | 121 ± 18** |
| T4 (0.1 μM) | 155 ± 11** |

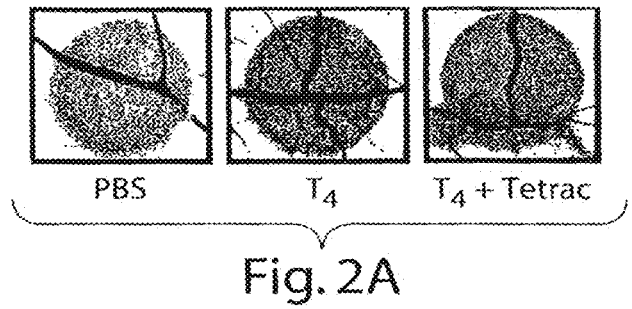
Fig. 2A
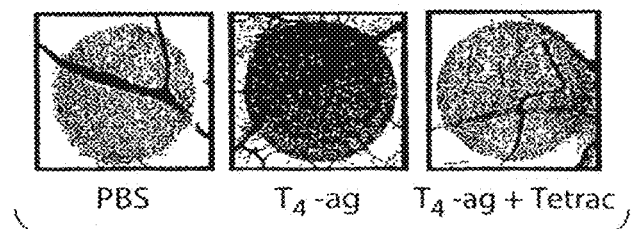
Fig. 2B
Summary of effects of $T_4$ and $T_3$-agarose and tetrac on angiogenesis
| Treatment | Angiogenesis Index |
|---|---|
| PBS | 67 ± 9 |
| $T_4$ (0.1 µM) | 156 ± 16** |
| Tetrac (0.1 µM) | 76 ± 9 |
| $T_4$ + tetrac | 66 ± 6 |
| $T_4$-agarose (0.1 µM) | 194 ± 28** |
| $T_4$-agarose + tetrac | 74 ± 7 |
Fig. 2C Effects of FGF2 and $T_4$ on angiogenesis

| Treatment | Angiogenesis Index |
|---|---|
| PBS | 86 ± 11 |
| FGF2 (0.5 μg/ml) | 126 ± 17* |
| FGF2 (1.0 μg/ml) | 172 ± 9** |
| $T_4$ (0.5 μM) | 115 ± 4* |
| $T_4$ + FGF2 (0.5 μg/ml) | 167 ± 10** |

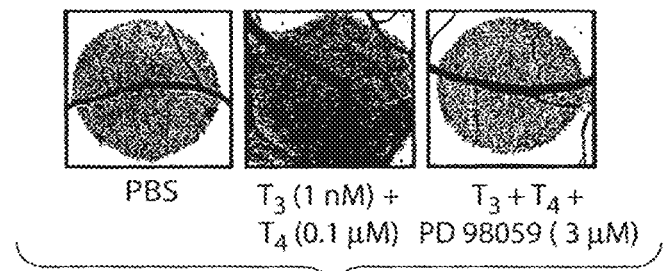
Fig. 5A
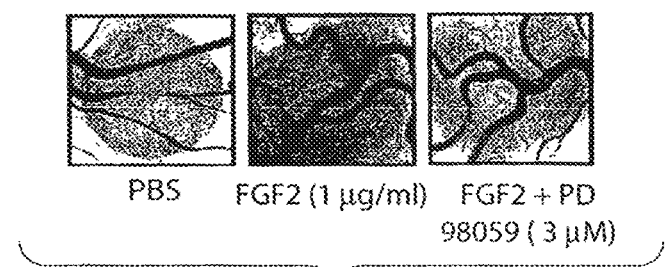
Fig. 5B
Effects of PD 98059 on angiogenesis stimulated by $T_4$ and FGF2
| Treatment | Angiogenesis Index |
| --- | --- |
| PBS | 63 ± 10 |
| $T_3$ (1 nM) + $T_4$ (0.1 μM) | 153 ± 15* |
| $T_3$ + $T_4$ + PD 98059 (3 μM) | 50 ± 10 |
| PBS | 86 ± 11 |
| FGF2 (1 μg/ml) | 191 ± 15** |
| FGF2 + PD 98059 (3 μM) | 110 ± 16 |
Fig. 5C

| CAM treatment | # of Branches ± SEM | % Inhibition ± SEM |
|---|---|---|
| PBS | 73 ± 8 | |
| $T_4$ (0.1 μM) | 170 ± 16 | 0 |
| $T_4$ + LM609 (10 μg) | 109 ± 9 | 64 ± 9 |

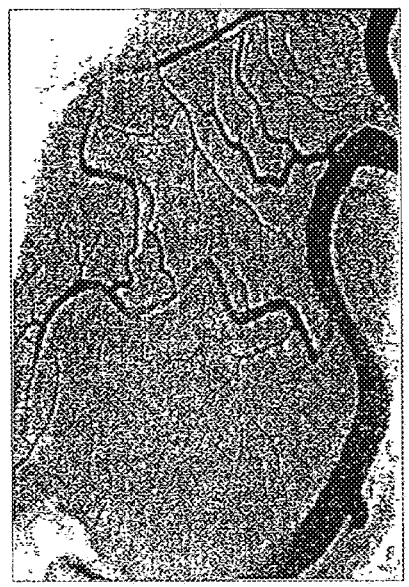
T₄ (0.1µM)
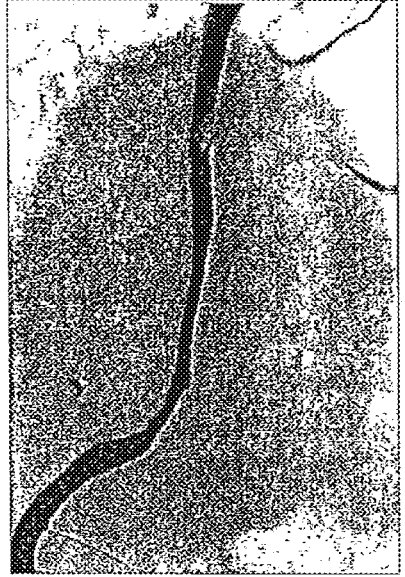
T₄ + XT199 (5µg)
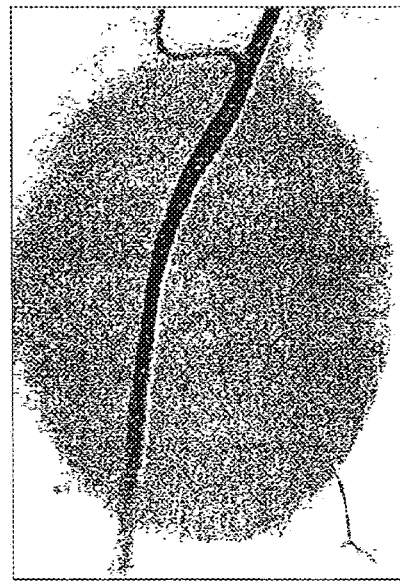
PBS
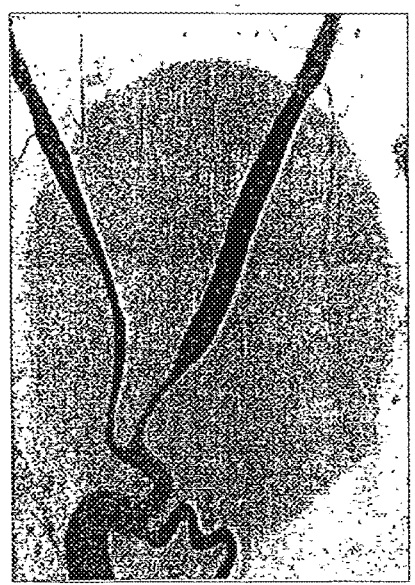
T₄ + LM609 (10µg)
Inhibitory Effect of αvβ3 MAB (LM609) and XT 199 on T4-induced angiogenesis in the CAM Model
Fig. 16C

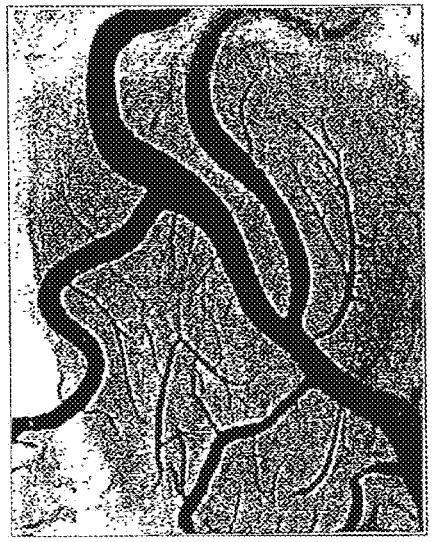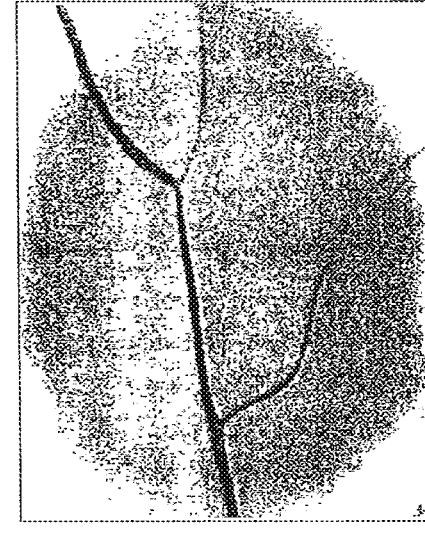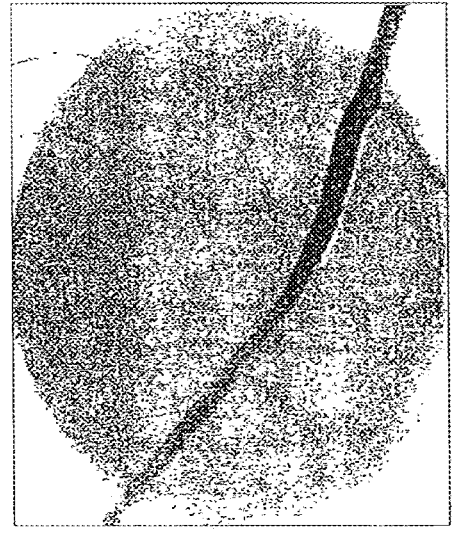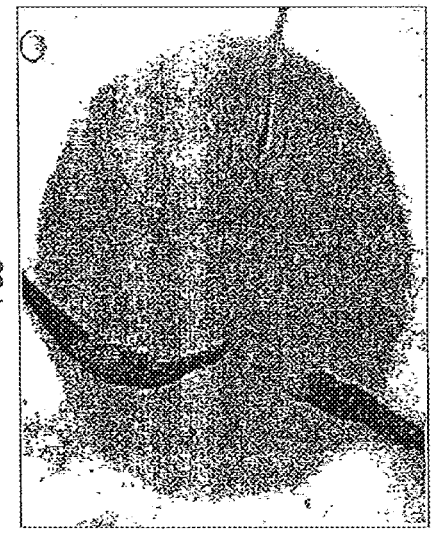
Fig. 16D

Table A

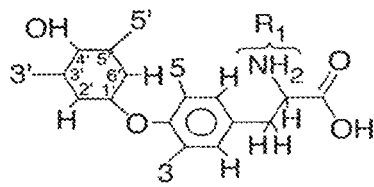

| 3' | 5' | 3 | 5 | $R_1$ | Analogue |
|---|---|---|---|---|---|
| I | I | I | I | $NH_2$ | L-$T_4$ |
| I | H | I | I | $NH_2$ | L-$T_3$ |
| I | I | I | H | $NH_2$ | r$T_3$ |
| H | H | I | I | $NH_2$ | 3,5-L-$T_2$ |
| I | I | H | H | $NH_2$ | 3',5'-L-$T_2$ |
| I | H | I | H | $NH_2$ | 3,3'-L-$T_2$ |
| I | H | H | H | $NH_2$ | 3'-L-$T_3$ |
| Br | Br | Br | Br | $NH_2$ | 3,5,3'-tetra-bromo-L-thyronine |
| H | H | Br | Br | $NH_2$ | 3,5,3',-dibromo-L-thyronine |
| Isop[a] | H | Me[b] | Me | $NH_2$ | DIMIT |
| Isop | H | Me | Me | NH-$COCH_3$ | N-acetyl DIMIT |

[a] Isop, isopropyl
[b] Me, methyl

Fig. 20A

Table B

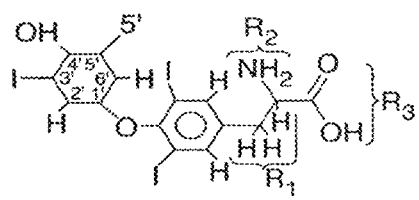

| $R_1$ | $R_2$ | $R_3$ | 5' | Analogue |
|---|---|---|---|---|
| $CH_2CH$ | H | $CO_2H$ | I | 3,5,3',5'-tetraiodo-thyropropionic acid |
| $CH_2$ | H | $CO_2H$ | I | 3,5,3',5'-tetraiodo-thyroacetic acid |
| $CH_2$ | H | $CO_2H$ | H | 3,5,3'-triiodothyroacetic acid |
| $CH_2CH$ | $NH_2$ | $COC_2H_5$ | I | L-$T_4$ ethylester |
| $CH_2CH$ | $NH_2$ | H | H | 3,5,3'-triiodothyronamine |

Fig. 20B

Table C

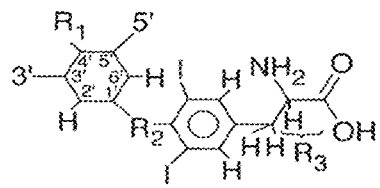

| $R_1$ | $R_2$ | $R_3$ | 3' | 5' | 3 | 5 | Analogue |
|---|---|---|---|---|---|---|---|
| H | O | L | H | H | I | I | 4'-deoxy $T_2$ |
| OH | S | L | I | H | I | I | S-bridged $T_3$ |
| OH | O | D | I | I | I | I | D-$T_4$ |
| OH | O | D | I | H | I | I | D-$T_3$ |

Fig. 20C

Table D

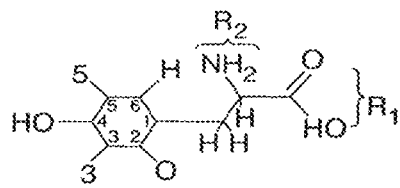

| 3 | 5 | $R_1$ | $R_3$ | Analogue |
|---|---|---|---|---|
| I | I | COOH | $NH_2$ | 3,5-diiodo-L-tyrosine |
| Br | Br | COOH | $NH_2$ | 3,5-dibromo-L-tyrosine |
| Me | Me | COOH | $NH_2$ | 3,5-dimethyl-DL-tyrosine |
| $NO_2$ | $NO_2$ | COOH | $NH_2$ | 3,5-dinitro-L-tyrosine |
| I | H | COOH | $NH_2$ | 3-iodo-L-tyrosine |
| $NO_2$ | H | COOH | $NH_2$ | 3-nitro-L-tyrosine |
| H | H | COOH | $NH_2$ | L-tyrosine |
| I | I | H | $NH_2$ | 3,5-diiodotyramine |
| H | H | H | $NH_2$ | tyramine |
| I | I | COOH | H | 3-(3,5-diiodo-4-hydroxyphenyl) propionic acid |
| H | H | COOH | H | 3-(p-hydroxyphenyl) propionic acid |

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 1
tggtatgtgg cactgaaacg                                                   20

<210> SEQ ID NO 2
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 2
ctcaatgacc tggcgaagac                                                   20

<210> SEQ ID NO 3
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 3
aaggtcatcc ctgagctgaa cg                                                22

<210> SEQ ID NO 4
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 4
gggtgtcgct gttgaagtca ga                                                22
```

THYROID HORMONE ANALOGS AND METHODS OF USE

RELATED APPLICATIONS

This application is a continuation-in-part of U.S. patent application Ser. No. 13/975,735 entitled THYROID HORMONE ANALOGS AND METHODS OF USE IN ANGIOGENESIS, filed Aug. 26, 2013, which is a continuation-in-part of U.S. patent application Ser. No. 12/626,068, filed Nov. 25, 2009, which is a divisional application of U.S. Pat. No. 7,785,632 filed Sep. 15, 2004, which claims priority to U.S. Patent Application No. 60/502,721, filed Sep. 15, 2003, the content of which is incorporated herein by reference in its entirety.

FIELD OF THE INVENTION

This invention relates to thyroid hormone, thyroid hormone analogs and derivatives, and polymeric forms thereof. Methods of using such compounds and pharmaceutical compositions containing the same are also disclosed. The invention also relates to methods of preparing such compounds.

BACKGROUND OF THE INVENTION

Thyroid hormones, L-thyroxine (T4) and L-triiodothyronine (T3), regulate many different physiological processes in different tissues in vertebrates. Most of the actions of thyroid hormones are mediated by the thyroid hormone receptor ("TR"), which is a member of the nuclear receptor superfamily of ligand-activated transcription regulators. This superfamily also includes receptors for steroid hormones, retinoids, and 1,25-dihydroxyvitamin D3. These receptors are transcription factors that can regulate expression of specific genes in various tissues and are targets for widely used drugs, such as tamoxifen, an estrogen receptor partial antagonist. There are two different genes that encode two different TRs, TRα and TRβ. These two TRs are often co-expressed at different levels in different tissues. Most thyroid hormones do not discriminate between the two TRs and bind both with similar affinities.

Gene knockout studies in mice indicate that TRβ plays a role in the development of the auditory system and in the negative feedback of thyroid stimulating hormone by T3 in the pituitary, whereas TRα modulates the effect of thyroid hormone on calorigenesis and on the cardiovascular system. The identification of TR antagonists could play an important role in the future treatment of hypothyroidism. Such molecules would act rapidly by directly antagonizing the effect of thyroid hormone at the receptor level, a significant improvement for individuals with hypothyroidism who require surgery, have cardiac disease, or are at risk for life-threatening thyrotoxic storm.

Thus, there remains a need for the development of compounds that selectively modulate thyroid hormone action by functioning as isoform-selective agonists or antagonists of the thyroid hormone receptors (TRs). Recent efforts have focused on the design and synthesis of thyroid hormone (T3/T4) antagonists as potential therapeutic agents and chemical probes. There is also a need for the development of thyromimetic compounds that are more accessible than the natural hormone and have potentially useful receptor binding and activation properties.

It is estimated that five million people are afflicted with chronic stable angina in the United States. Each year 200,000 people under the age of 65 die from what is termed "premature ischemic heart disease." Despite medical therapy, many others go on to suffer myocardial infarction and debilitating symptoms prompting the need for revascularization with either percutaneous transluminal coronary angioplasty or coronary artery bypass surgery. It has been postulated that one way of relieving myocardial ischemia would be to enhance coronary collateral circulation.

Correlations have now been made between the anatomic appearance of coronary collateral vessels ("collaterals") visualized at the time of intracoronary thrombolytic therapy during the acute phase of myocardial infarction and the creatine kinase time-activity curve, infarct size, and aneurysm formation. These studies demonstrate a protective role of collaterals in hearts with coronary obstructive disease, showing smaller infarcts, less aneurysm formation, and improved ventricular function compared with patients in whom collaterals were not visualized. When the cardiac myocyte is rendered ischemic, collaterals develop actively by growth with DNA replication and mitosis of endothelial and smooth muscle cells. Once ischemia develops, these factors are activated and become available for receptor occupation, which may initiate angiogenesis after exposure to exogenous heparin. Unfortunately, the "natural" process by which angiogenesis occurs is inadequate to reverse the ischemia in almost all patients with coronary artery disease.

During ischemia, adenosine is released through the breakdown of ATP. Adenosine participates in many cardio-protective biological events. Adenosine has a role in hemodynamic changes such as bradycardia and vasodilation, and has been suggested to have a role in such unrelated phenomena as preconditioning and possibly the reduction in reperfusion injury (Ely and Beme, Circulation, 85: 893 (1992).

Angiogenesis is the development of new blood vessels from preexisting blood vessels (Mousa, S. A., In *Angiogenesis Inhibitors and Stimulators: Potential Therapeutic Implications*, Landes Bioscience, Georgetown, Tex.; Chapter 1, (2000)). Physiologically, angiogenesis ensures proper development of mature organisms, prepares the womb for egg implantation, and plays a key role in wound healing. The development of vascular networks during embryogenesis or normal and pathological angiogenesis depends on growth factors and cellular interactions with the extracellular matrix (Breier et al., *Trends in Cell Biology* 6:454-456 (1996); Folkman, *Nature Medicine* 1:27-31 (1995); Risau, *Nature* 386: 671-674 (1997). Blood vessels arise during embryogenesis by two processes: vasculogenesis and angiogenesis (Blood et al., *Bioch. Biophys. Acta* 1032:89-118 (1990). Angiogenesis is a multi-step process controlled by the balance of pro- and anti-angiogenic factors. The latter stages of this process involve proliferation and the organization of endothelial cells (EC) into tube-like structures. Growth factors such as FGF2 and VEGF are thought to be key players in promoting endothelial cell growth and differentiation.

Control of angiogenesis is a complex process involving local release of vascular growth factors (P Carmeliet, Ann NY Acad Sci 902:249-260, 2000), extracellular matrix, adhesion molecules, and metabolic factors (R J Tomanek, G C Schatteman, Anat Rec 261:126-135, 2000). Mechanical forces within blood vessels may also play a role (O Hudlicka, Molec Cell Biochem 147:57-68, 1995). The principal classes of endogenous growth factors implicated in new blood vessel growth are the fibroblast growth factor (FGF) family and vascular endothelial growth factor (VEGF)(G Pages, Ann NY Acad Sci 902:187-200, 2000). The mitogen-activated protein kinase (MAPK; ERK1/2) signal transduction cascade is involved both in VEGF gene expression and in control of proliferation of vascular endothelial cells.

Intrinsic adenosine may facilitate the coronary flow response to increased myocardial oxygen demands and so modulate the coronary flow reserve (Ethier et al., Am. J. Physiol., H131 (1993)) by demonstrating that the addition of physiological concentrations of adenosine to human umbilical vein endothelial cell cultures stimulates proliferation, possibly via a surface receptor. Adenosine may be a factor for human endothelial cell growth and possibly angiogenesis. Angiogenesis appears to be protective for patients with obstructive blood flow such as coronary artery disease ("CAD"), but the rate at which blood vessels grow naturally is inadequate to reverse the disease. Thus, strategies to enhance and accelerate the body's natural angiogenesis potential should be beneficial in patients with CAD.

Similarly, wound healing is a major problem in many developing countries and diabetics have impaired wound healing and chronic inflammatory disorders, with increased use of various cyclooxygenase-2 (COX2) inhibitors. Angiogenesis is necessary for wound repair since the new vessels provide nutrients to support the active cells, promote granulation tissue formation, and facilitate the clearance of debris. Approximately 60% of the granulation tissue mass is composed of blood vessels which also supply the necessary oxygen to stimulate repair and vessel growth. It is well documented that angiogenic factors are present in wound fluid and promote repair while antiangiogenic factors inhibit repair. Wound angiogenesis is a complex multi-step process. Despite a detailed knowledge about many angiogenic factors, little progress has been made in defining the source of these factors, the regulatory events involved in wound angiogenesis, and in the clinical use of angiogenic stimulants to promote repair. Further complicating the understanding of wound angiogenesis and repair is the fact that the mechanisms and mediators involved in repair likely vary depending on the depth of the wound, type of wound (burn, trauma, etc.), and the location (muscle, skin, bone, etc.). The condition and age of the patient (diabetic, paraplegic, on steroid therapy, elderly vs infant, etc) can also determine the rate of repair and response to angiogenic factors. The sex of the patient and hormonal status (premenopausal, post menopausal, etc.) may also influence the repair mechanisms and responses. Impaired wound healing particularly affects the elderly and many of the 14 million diabetics in the United States. Because reduced angiogenesis is often a causative agent for wound healing problems in these patient populations, it is important to define the angiogenic factors important in wound repair and to develop clinical uses to prevent and/or correct impaired wound healing.

Thus, there remains a need for an effective therapy in the way of angiogenic agents as either primary or adjunctive therapy for promotion of wound healing, coronary angiogenesis, or other angiogenic-related disorders, with minimum side effects. Such a therapy would be particularly useful for patients who have vascular disorders such as myocardial infarctions, stroke or peripheral artery diseases and could be used prophylactically in patients who have poor coronary circulation, which places them at high risk of ischemia and myocardial infarctions.

It is interesting to note that angiogenesis also occurs in other situations, but which are undesirable, including solid tumor growth and metastasis; rheumatoid arthritis; psoriasis; scleroderma; and three common causes of blindness—diabetic retinopathy, retrolental fibroplasia, and neovascular glaucoma (in fact, diseases of the eye are almost always accompanied by vascularization). The process of wound angiogenesis actually has many features in common with tumor angiogenesis. Thus, there are some conditions, such as diabetic retinopathy or the occurrence of primary or metastatic tumors, where angiogenesis is undesirable. Thus, there remains a need for methods by which to inhibit the effect of angiogenic agents.

SUMMARY OF THE INVENTION

The invention is based, in part, on the discovery that thyroid hormone, thyroid hormone analogs, and their polymeric forms, act at the cell membrane level and have pro-angiogenic properties that are independent of the nuclear thyroid hormone effects. Accordingly, these thyroid hormone analogs and polymeric forms (i.e., angiogenic agents) can be used to treat a variety of disorders. Similarly, the invention is also based on the discovery that thyroid hormone analog antagonists inhibit the pro-angiogenic effect of such analogs, and can also be used to treat a variety of disorders.

Accordingly, in one aspect the invention features methods for treating a condition amenable to treatment by inhibiting angiogenesis by administering to a subject in need thereof an effective amount of a compound selected from the group consisting of tetraiodothyroacetic acid (tetrac), triiodothyroacetic acid (triac) and a combination thereof conjugated via a covalent bond to a polymer, wherein said polymer is polyglycolide, polylactic acid, or co-polymers thereof, wherein said polymer is formulated into a nanoparticle, wherein said nanoparticle is less than 200 nanometers, and wherein the administered compound acts at the cell membrane level for inhibiting pro-angiogenesis agents.

In one embodiment, the thyroid hormone analog may be used to treat a condition wherein the condition amenable to treatment by anti-angiogenesis is a primary tumor, metastatic tumor, or diabetic retinopathy.

Thyroid hormone, thyroid hormone analogs, or polymeric forms thereof according to the invention can also be co-administered with one or more biologically active substances that can include, for example, growth factors, vasodilators, anti-coagulants, anti-virals, anti-bacterials, anti-inflammatories, immuno-suppressants, analgesics, vascularizing agents, or cell adhesion molecules, or combinations thereof. In one embodiment, the thyroid hormone analog or polymeric form is administered as a bolus injection prior to or post-administering one or more biologically active substance.

Examples of the conditions amenable to treatment by inhibiting angiogenesis include, but are not limited to, primary or metastatic tumors, diabetic retinopathy, and related conditions. Examples of the anti-angiogenesis agents used for inhibiting angiogenesis are also provided by the invention and include, but are not limited to, tetraiodothyroacetic acid (tetrac), triiodothyroacetic acid (triac), monoclonal antibody LM609, XT 199 or combinations thereof. Such anti-angiogenesis agents can act at the cell surface to inhibit the pro-angiogenesis agents.

In one embodiment, the anti-angiogenesis agent is administered by a parenteral, oral, rectal, or topical mode, or combination thereof. In another embodiment, the anti-angiogenesis agent can be co-administered with one or more anti-angiogenesis therapies or chemotherapeutic agents. Chemotherapeutic agents may include, but are not limited to, doxorubicin, etoposide, cyclophophamide, 5-fluoracil, cisplatin, trichostatin A, paclitaxel, gemcitabine, taxotere, cis-platinum, carboplatinum, irinotecan, topotecan, adrimycin, bortezomib, and any combinations or derivatives thereof.

The details of one or more embodiments of the invention have been set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural references unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference in their entirety.

BRIEF DESCRIPTION OF THE DRAWINGS

FIG. 2A: depicts tetrac inhibiting stimulation of angiogenesis by T4, including 2.5-fold increase in blood vessel branch formation is seen in a representative CAM preparation exposed to 0.1 µM T4 for 3 days. In 3 similar experiments, there was a 2.3-fold increase. This effect of the hormone is inhibited by tetrac (0.1 µM), a T4 analogue shown previously to inhibit plasma membrane actions of T4.

FIG. 2B: depicts T4-ag (0.1 µM) stimulating angiogenesis 2.3-fold (2.9-fold in 3 experiments), an effect also blocked by tetrac.

FIG. 2C: depicts a summary of the results of 3 experiments that examine the actions of tetrac (which when administered alone does not stimulate angiogenesis), T4-ag, and T4 in the CAM assay. Data (means±SEM) were obtained from 10 images for each experimental condition in each of 3 experiments. **P<0.001 by ANOVA, comparing T4-treated and T4-agarose-treated samples with PBS-treated control samples.

FIG. 5A: depicts the effect of PD 98059, a MAPK (ERK1/2) signal transduction cascade inhibitor, on angiogenesis induced by T4, T3, and FGF2 specifically, demonstrating that angiogenesis stimulated by T4 (0.1 µM) and T3 (1 nM) together is fully inhibited by PD 98059 (3 µM).

FIG. 5B: depicts angiogenesis induced by FGF2 (1 µg/mL) is also inhibited by PD 98059, indicating that the action of the growth factor is also dependent on activation of the ERK1/2 pathway. In the context of the experiments involving T4-agarose (T4-ag) and tetrac (FIG. 2) indicating that T4 initiates its proangiogenic effect at the cell membrane, results shown in FIGS. 5A and B are consistent with 2 roles played by MAPK in the proangiogenic action of thyroid hormone: ERK1/2 transduces the early signal of the hormone that leads to FGF2 elaboration and transduces the subsequent action of FGF2 on angiogenesis.

FIG. 5C: depicts the summary of results of 3 experiments, represented by A and B, showing the effect of PD98059 on the actions of T4 and FGF2 in the CAM model.

*P<0.01; **P<0.001, indicating results of ANOVA on data from 3 experiments.

Figure 6A:
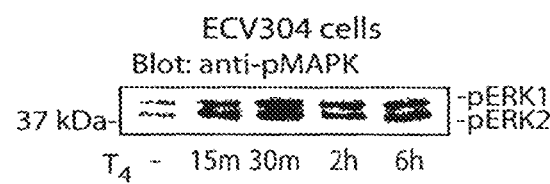

FIG. 6A: depicts that T4 and FGF2 activate MAPK in ECV304 endothelial cells. Cells were prepared in M199 medium with 0.25% hormone-depleted serum and treated with T4 (0.1 µM) for 15 minutes to 6 hours. Cells were harvested and nuclear fractions were prepared. Nucleoproteins, separated by gel electrophoresis, were immunoblotted with antibody to phosphorylated MAPK (pERK1 and pERK2, 44 and 42 kDa, respectively), followed by a second antibody linked to a luminescence-detection system. A β-actin immunoblot of nuclear fractions serves as a control for gel loading in each part of this figure. Each immunoblot is representative of 3 experiments. T4 causes increased phosphorylation and nuclear translocation of ERK1/2 in ECV304 cells. The effect is maximal in 30 minutes, although the effect remains for ≥6 hours.

Figure 6B:
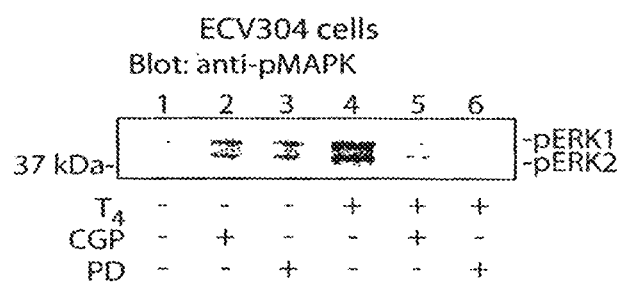

FIG. 6B: depicts ECV304 cells treated with the ERK1/2 activation inhibitor PD 98059 (PD; 30 µM) or the PKC inhibitor CGP41251 (CGP; 100 nM) for 30 minutes, after which $10^{-7}$ M T4 was added for 15 minutes to cell samples as shown. Nuclei were harvested, and this representative experiment shows increased phosphorylation (activation) of ERK1/2 by T4 (lane 4), which is blocked by both inhibitors (lanes 5 and 6), suggesting that PKC activity is a requisite for MAPK activation by T4 in endothelial cells.

Figure 6C:
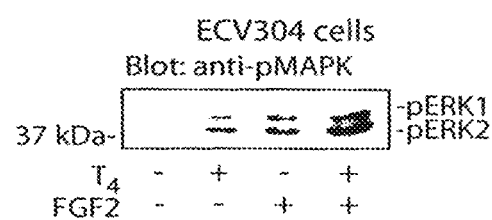

FIG. 6C: depicts ECV304 cells treated with either T4 ($10^{-7}$ mol/L), FGF2 (10 ng/mL), or both agents for 15 minutes. The figure shows pERK1/2 accumulation in nuclei with either hormone or growth factor treatment and enhanced nuclear pERK1/2 accumulation with both agents together.

Figure 7:
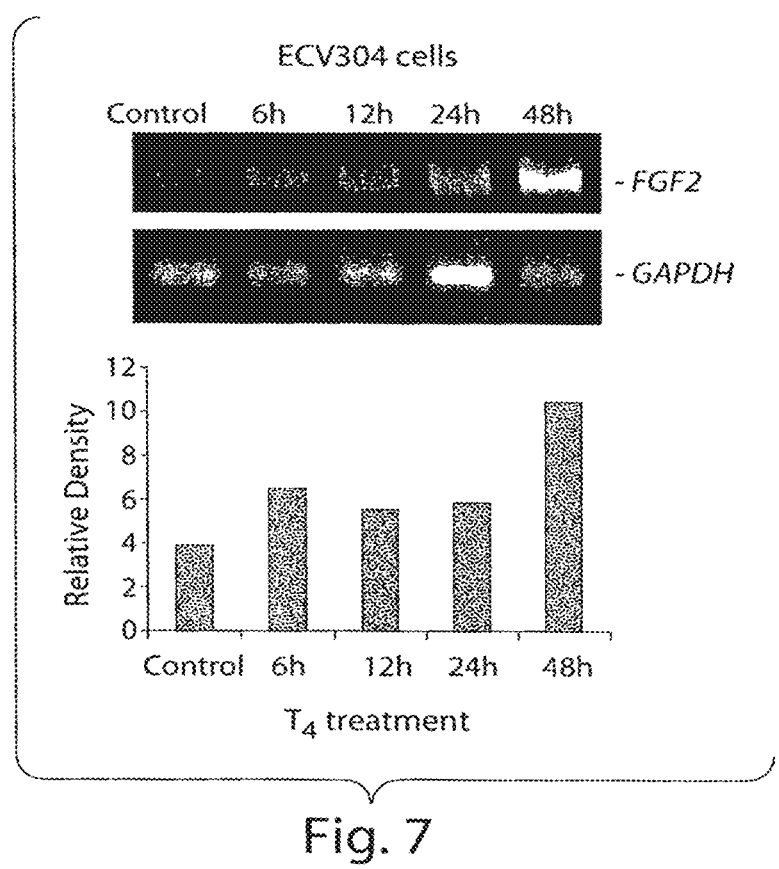

FIG. 7: depicts T4 increasing accumulation of FGF2 cDNA in ECV304 endothelial cells. Cells were treated for 6 to 48 hours with T4 ($10^{-7}$ mol/L) and FGF2 and GAPDH cDNAs isolated from each cell aliquot. The levels of FGF2 cDNA, shown in the top blot, were corrected for variations in GAPDH cDNA content, shown in the bottom blot, and the corrected levels of FGF2 are illustrated below in the graph (mean±SE of mean; n=2 experiments). There was increased abundance of FGF2 transcript in RNA extracted from cells treated with T4 at all time points. *P<0.05; **P<0.01, indicating comparison by ANOVA of values at each time point to control value.

Figure 8:
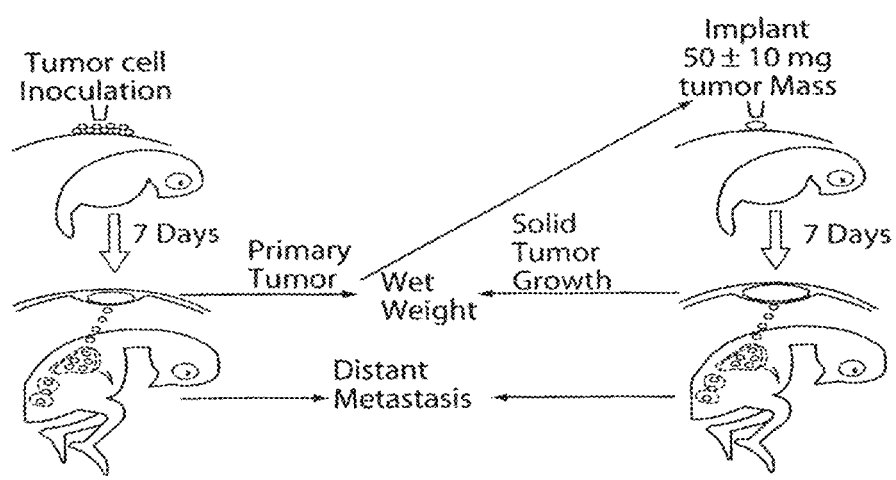
Figure 9:
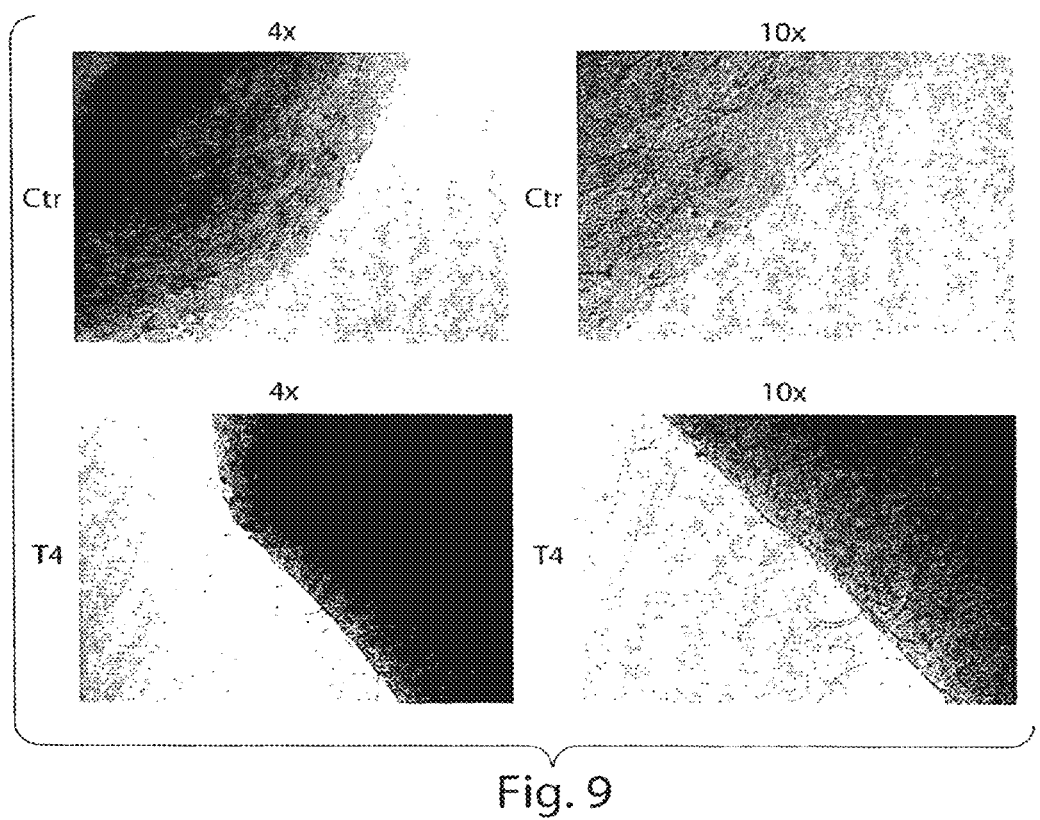

FIG. 8: depicts an illustration of the CAM model of tumor implant of the 7 day chick embryo tumor growth model FIG. 9: depicts photographs of human dermal fibroblast cells exposed to T4 and control, according to the 3D Wound Healing Assay described herein.

Figure 10:
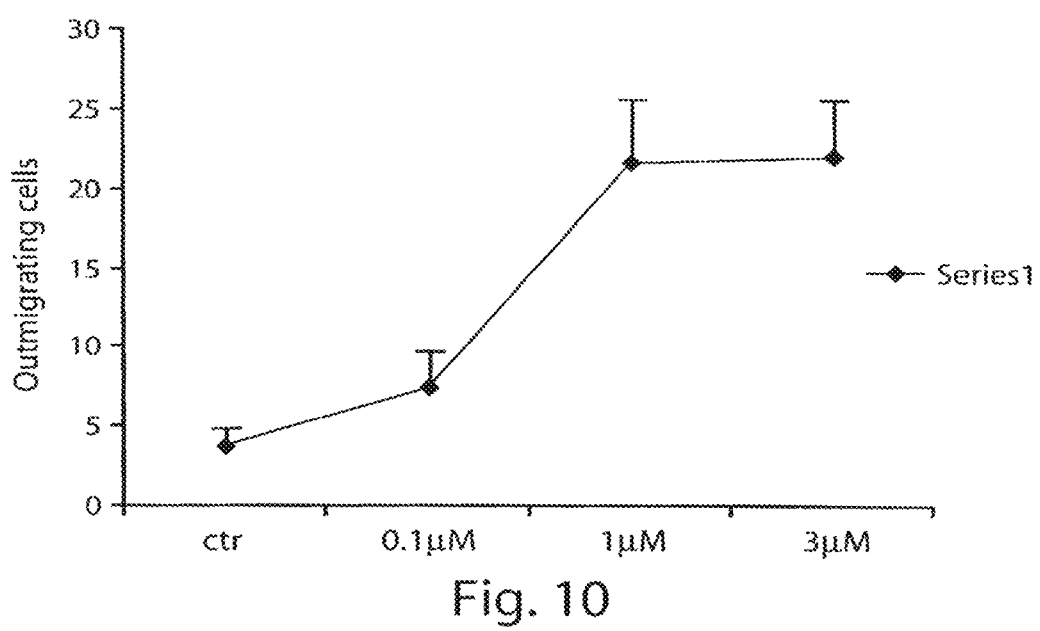

FIG. 10: depicts T4 increasing wound healing (measured by out migrating cells) in a dose-dependent manner between concentrations of 0.1 μM and 1.0 μM. This same increase is not seen in concentrations of T4 between 1.0 μM and 3.0 μM.

Figure 11A:
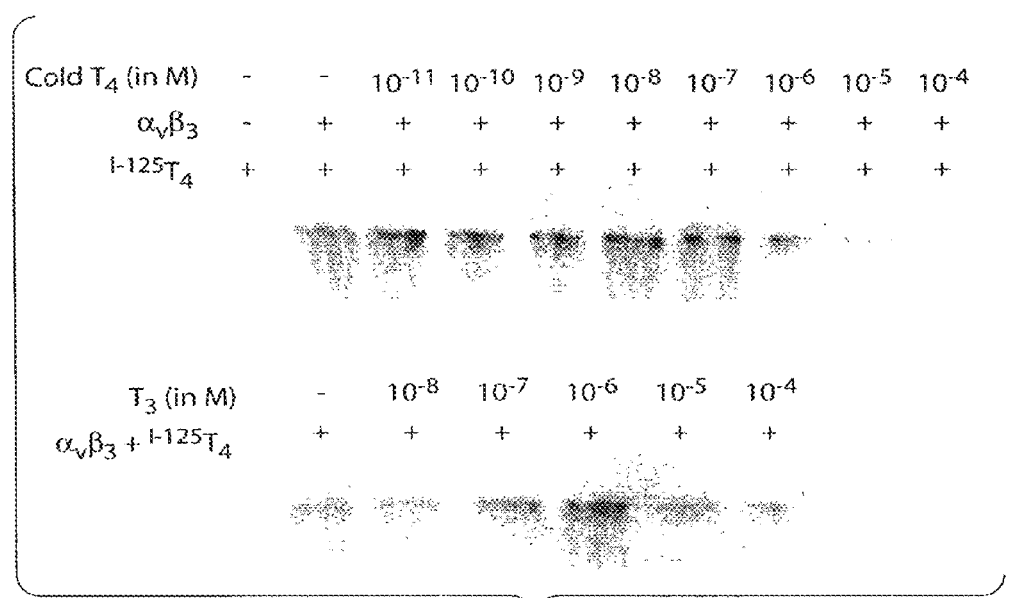
Figure 11B:
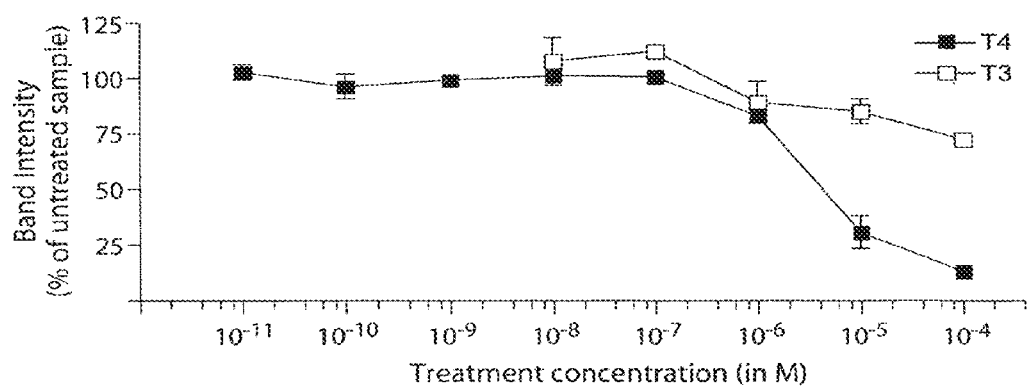

FIGS. 11A and 11B: depict the effect of unlabeled T4 and T3 on $I^{125}$-T4 binding to purified integrin. Unlabeled T4 (10-4M to 10-11M) or T3 (10-4M to 10-8M) were added to purified αVβ3 integrin (2 μg/sample) and allowed to incubate for 30 min. at room temperature. Two microcuries of $I^{125}$ labeled T4 was added to each sample. The samples were incubated for 20 min. at room temperature, mixed with loading dye, and run on a 5% Native gel for 24 hrs. at 4° C. at 45 mÅ. Following electrophoresis, the gels were wrapped in plastic wrap and exposed to film. $I^{125}$-T4 binding to purified αVβ3 is unaffected by unlabeled T4 in the range of 10-11M to 10-7M, but is competed out in a dose-dependent manner by unlabeled T4 at a concentration of 10-6M. Radiolabeled T4 binding to the integrin is almost completely displaced by 10-4M unlabeled T4. T3 is less effective at competing out T4 binding to αVβ3, reducing the signal by 11%, 16%, and 28% at 10-6M, 10-5M, and 10-4M T3, respectively.

Figure 12A:
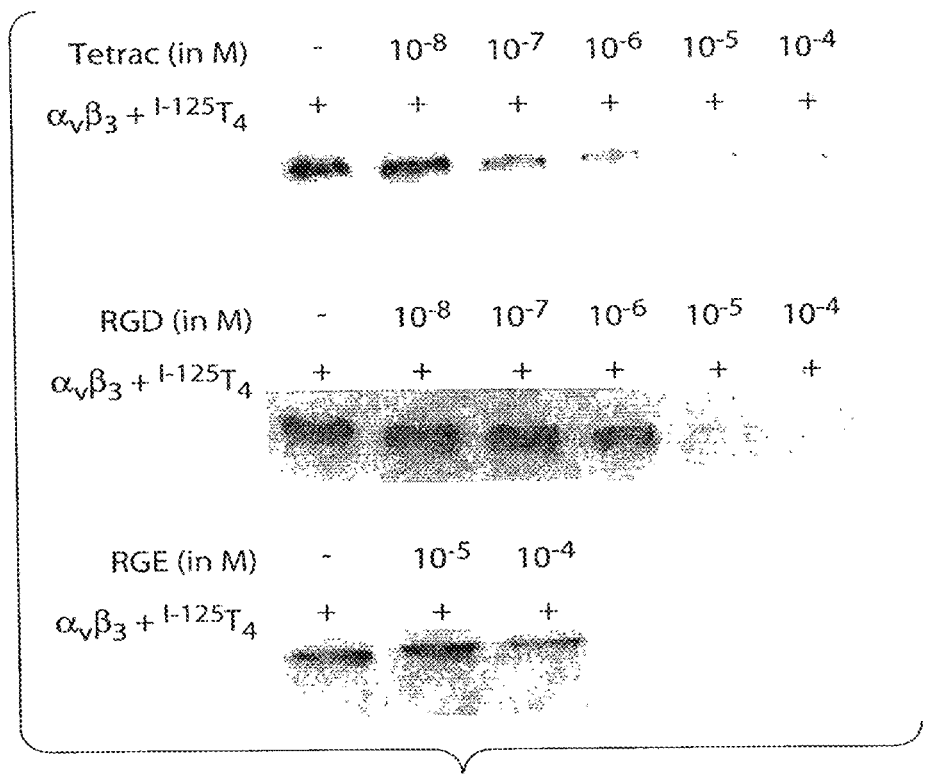

FIG. 12A: depicts tetrac and an RGD containing peptide, but not an RGE containing peptide compete out T4 binding to purified αVβ3. The tetrac addition to purified αVβ3 reduces $I^{125}$-labeled T4 binding to the integrin in a dose dependent manner. 10-8M tetrac is ineffective at competing out T4 binding to the integrin. The association of T4 and αVβ3 was reduced by 38% in the presence of 10-7M tetrac and by 90% with 10-5M tetrac. Addition of an RGD peptide at 10-5M competes out T4 binding to αVβ3. Application of 10-5M and 10-4M RGE peptide, as a control for the RGD peptide, was unable to diminish T4 binding to purified αVβ3.

Figure 12B:
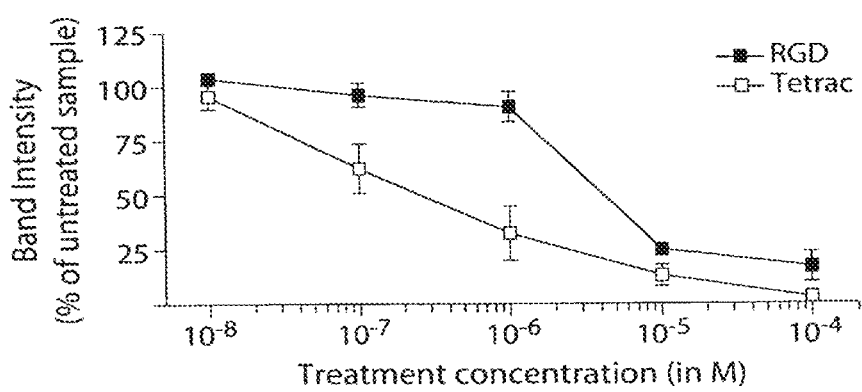

FIG. 12B: depicts a graphical representation of the tetrac and RGD data from FIG. 12A. Data points are shown as the mean±S.D. for 3 independent experiments.

Figure 13A:
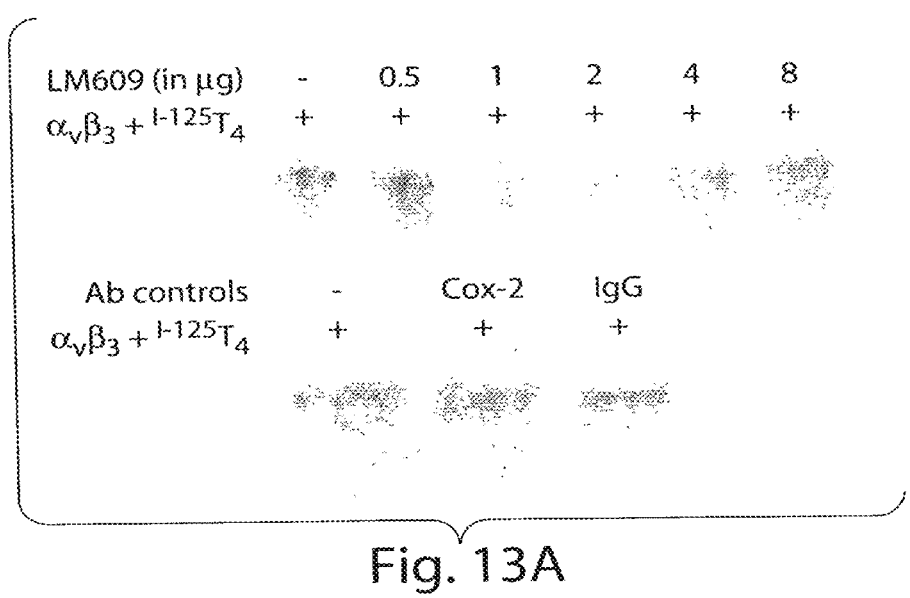

FIG. 13A: depicts the effects of the monoclonal antibody LM609 on T4 binding to αVβ3. LM609 was added to αVβ3 at the indicated concentrations. One μg of LM609 per sample reduces $I^{125}$-labeled T4 binding to the integrin by 52%. Maximal inhibition of T4 binding to the integrin is reached when concentrations of LM609 are 2 μg per sample and is maintained with antibody concentrations as high as 8 μg. As a control for antibody specificity, 10 μm/sample COX-2 mAB and 10 μm/sample mouse IgG were added to αVβ3 prior to incubation with T4.

Figure 13B:
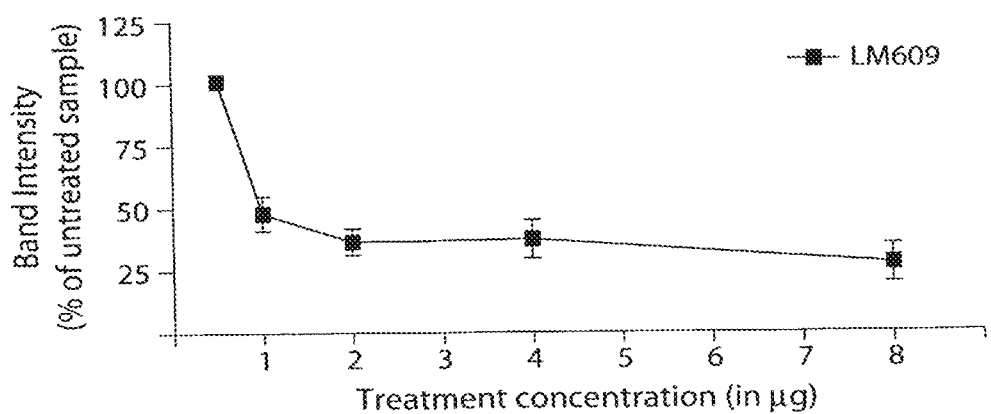

FIG. 13B: depicts a graphical representation of data from FIG. 13A. Data points are shown as the mean±S.D. for 3 independent experiments.

Figure 14A:
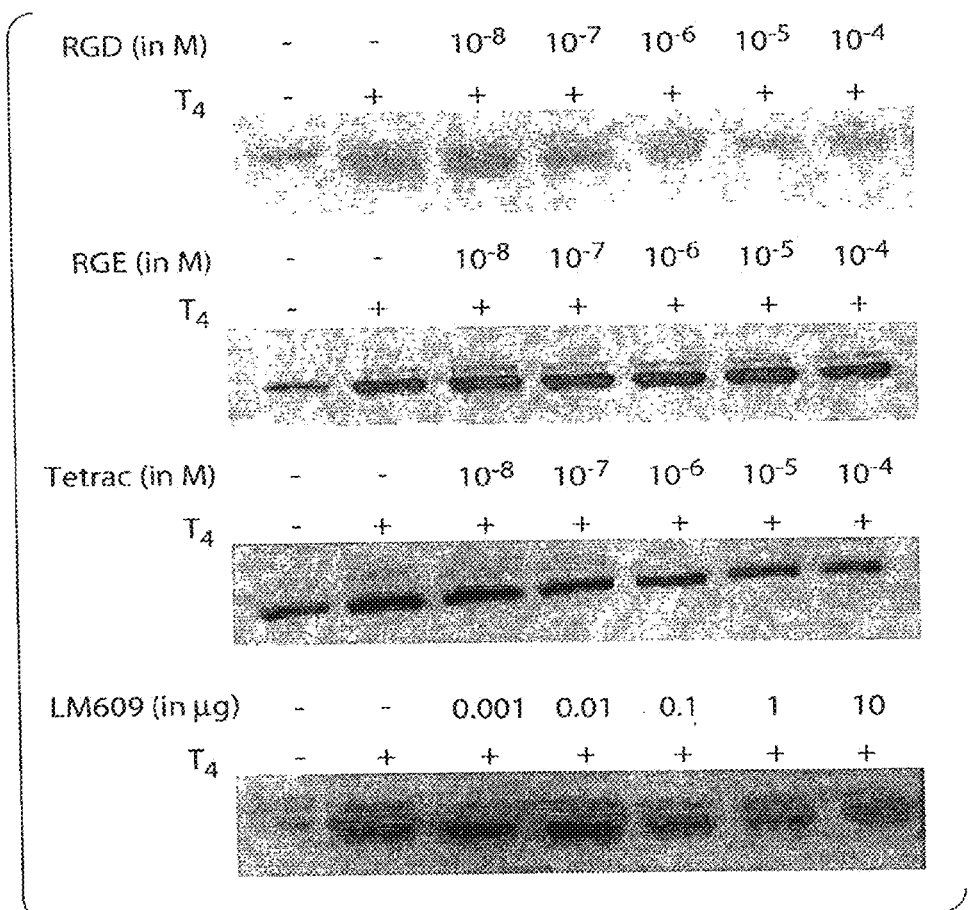

FIG. 14A: depicts the effect of RGD, RGE, tetrac, and the mAB LM609 on T4-induced MAPK activation. CV-1 cells (50-70% confluency) were treated for 30 min. with $10^{-7}$ M T4 ($10^{-7}$ M total concentration, $10^{-10}$ M free concentration). Selected samples were treated for 16 hours with the indicated concentrations of either an RGD containing peptide, an RGE containing peptide, tetrac, or LM609 prior to the addition of T4. Nuclear proteins were separated by SDS-PAGE and immunoblotted with anti-phospho-MAPK (pERK1/2) antibody. Nuclear accumulation of pERK1/2 is diminished in samples treated with $10^{-6}$ M RGD peptide or higher, but not significantly altered in samples treated with $10^{-4}$ M RGE. pERK1/2 accumulation is decreased 76% in CV1 cells treated with $10^{-6}$M tetrac, while $10^{-5}$M and higher concentrations of tetrac reduce nuclear accumulation of pERK1/2 to levels similar to the untreated control samples. The monoclonal antibody to αVβ3 LM609 decrease accumulation of activated MAPK in the nucleus when it is applied to CV1 cultures a concentration of 1 μg/ml.

Figure 14B:
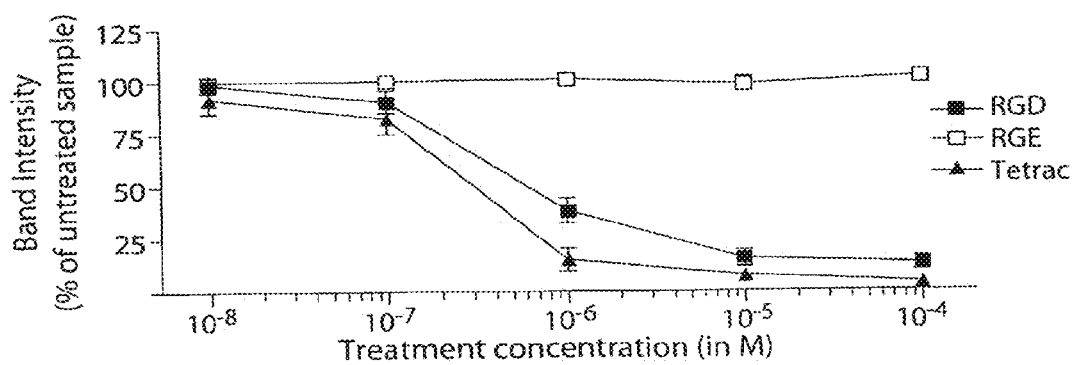

FIG. 14B: depicts a graphical representation of the data for RGD, RGE, and tetrac shown in FIG. 14A. Data points represent the mean±S.D. for 3 separate experiments.

Figure 15A:
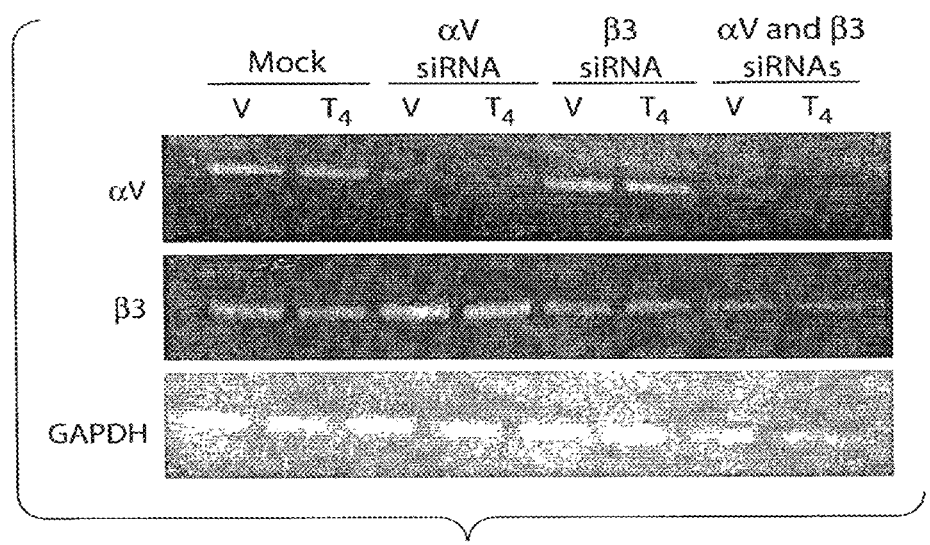

FIG. 15A: depicts the effects of siRNA to αV and β3 on T4 induced MAPK activation. CV1 cells were transfected with siRNA (100 nM final concentration) to αV, β3, or αV and β3 together. Two days after transfection, the cells were treated with $10^{-7}$M T4. A) RT-PCR was performed from RNA isolated from each transfection group to verify the specificity and functionality of each siRNA.

Figure 15B:
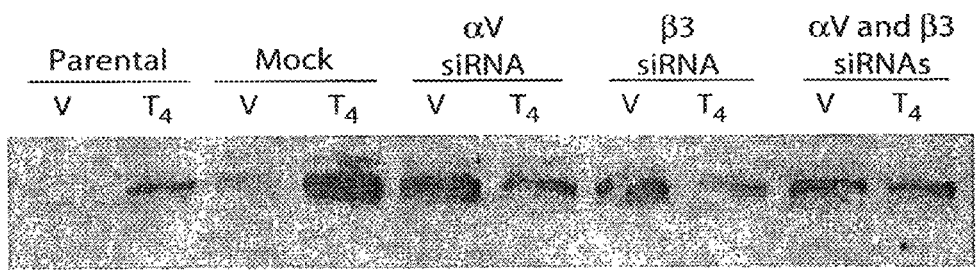

FIG. 15B: depicts nuclear proteins from each transfection of FIG. 15A which were isolated and subjected to SDS-PAGE.

Figures 16A, 16B:
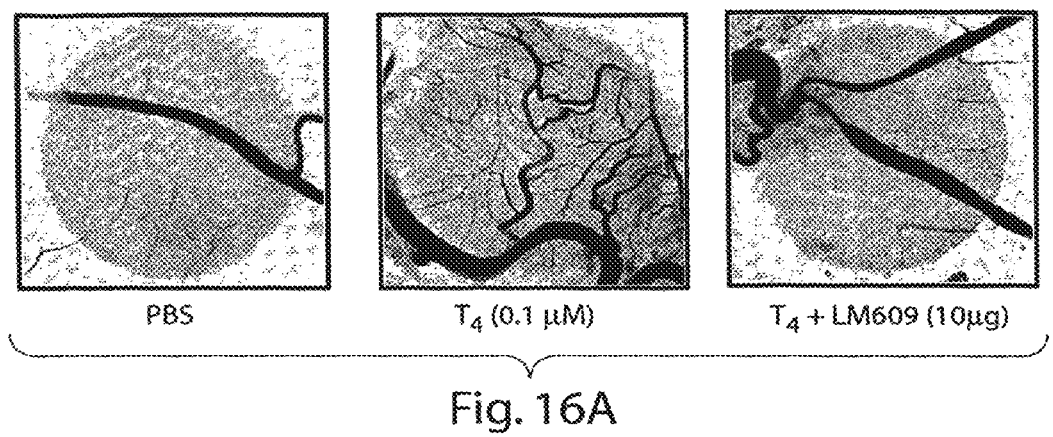

FIG. 16A: depicts the inhibitory effect of αVβ3 mAB (LM609) on T4-stimulated angiogenesis in the CAM Model. Samples were exposed to PBS, T4 (0.1 μM), or T4 plus 10 mg/ml LM609 for 3 days. Angiogenesis stimulated by T4 is substantially inhibited by the addition of the αVβ3 monoclonal antibody LM609.

FIG. 16B: depicts the tabulation of the mean±SEM of new branches formed from existing blood vessels during the experimental period of FIG. 16A. Data was drawn from 3 separate experiments, each containing 9 samples in each treatment group.

FIGS. 16C and 16D: depicts angiogenesis stimulated by T4 or FGF2 is also inhibited by the addition of the αVβ3 monoclonal antibody LM609 or XT 199.

Figure 17:
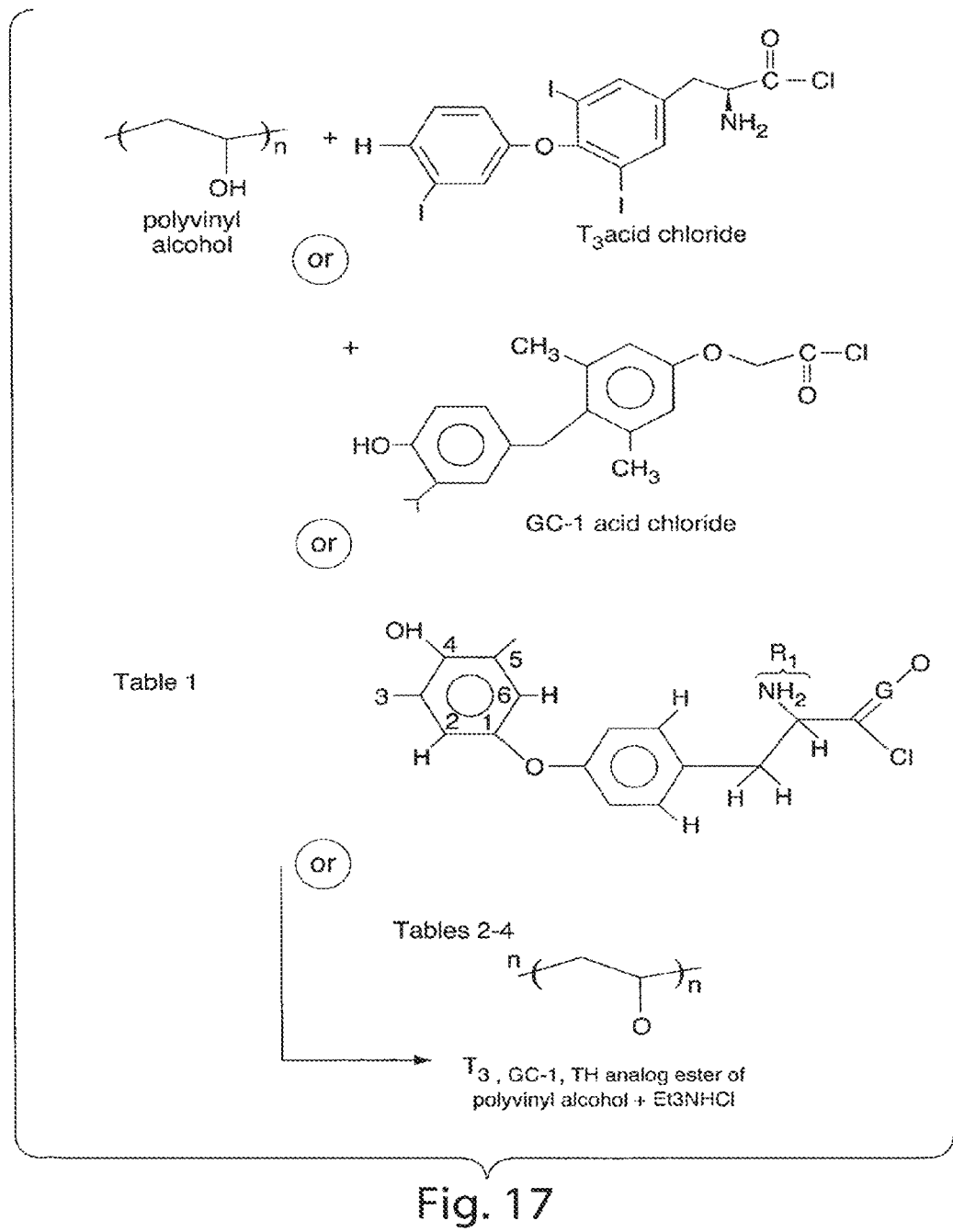

FIG. 17: depicts a preparation of commercially available polyvinyl alcohol (or related co-polymers) esterified by treatment with the acid chloride of thyroid hormone analogs, namely the acid chloride form. The hydrochloride salt is neutralized by the addition of triethylamine to afford triethylamine hydrochloride which can be washed away with water upon precipitation of the thyroid hormone ester polymer form for different analogs.

Figure 18:
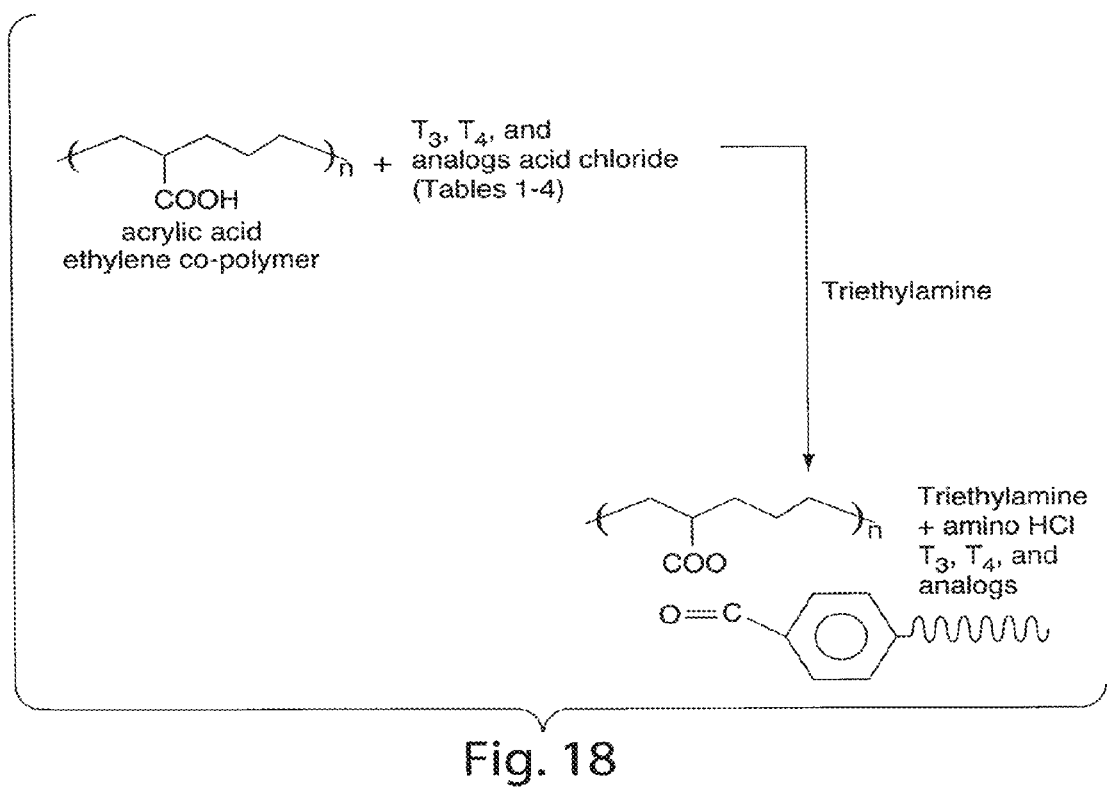

FIG. 18: depicts a polymer covalent conjugation using an anhydride linkage that is derived from reaction of an acrylic acid co-polymer. Neutralization of the hydrochloric acid is accomplished by treatment with triethylamine and subsequent washing of the precipitated polyanhydride polymer with water removes the triethylamine hydrochloride byproduct. This reaction will lead to the formation of Thyroid hormone analog acrylic acid co-polymer+triethylamine.

Figure 19:
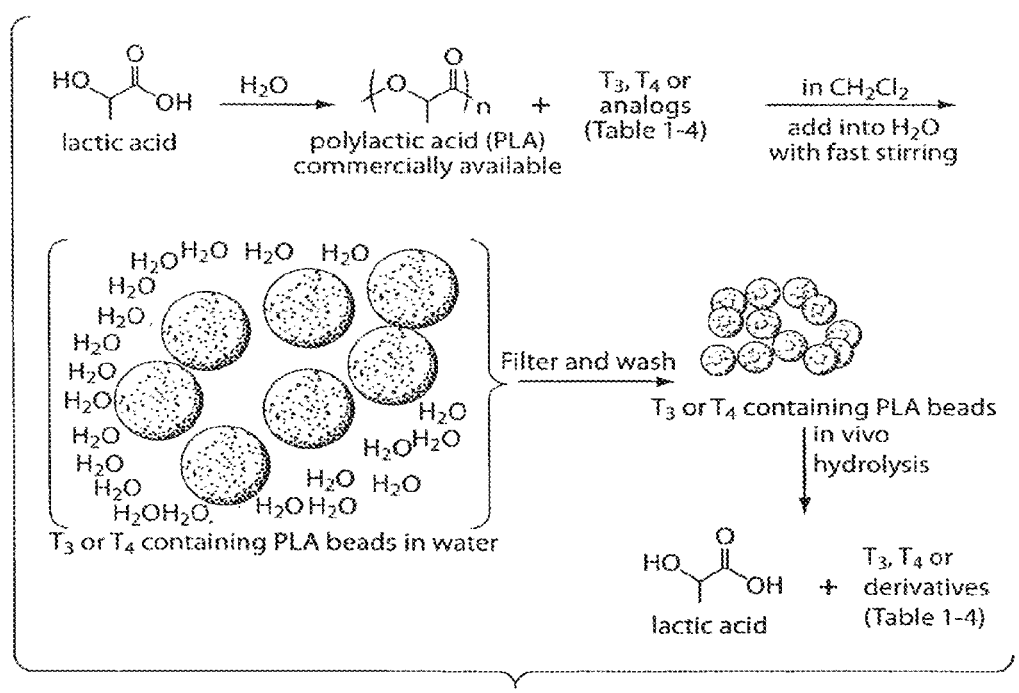

FIG. 19: depicts the process of entrapment in a polylactic acid polymer. Polylactic acid polyester polymers (PLA) undergo hydrolysis in vivo to the lactic acid monomer and this has been exploited as a vehicle for drug delivery systems in humans. Unlike the prior two covalent methods where the thyroid hormone analog is linked by a chemical bond to the polymer, this would be a non-covalent method that would encapsulate the thyroid hormone analog into PLA polymer beads. This reaction will lead to the formation of thyroid hormone analog containing PLA beads in water. Filter and washing will result in the formation of thyroid hormone analog containing PLA beads, which upon in vivo hydrolysis will lead to the generation of controlled levels of thyroid hormone plus lactic acid.

FIGS. 20A, 20B, 20C and 20D: depict substitutions required to achieve various thyroid hormone analogs which can be conjugated to create polymeric forms of thyroid hormone analogs of the invention.

Figure 21:
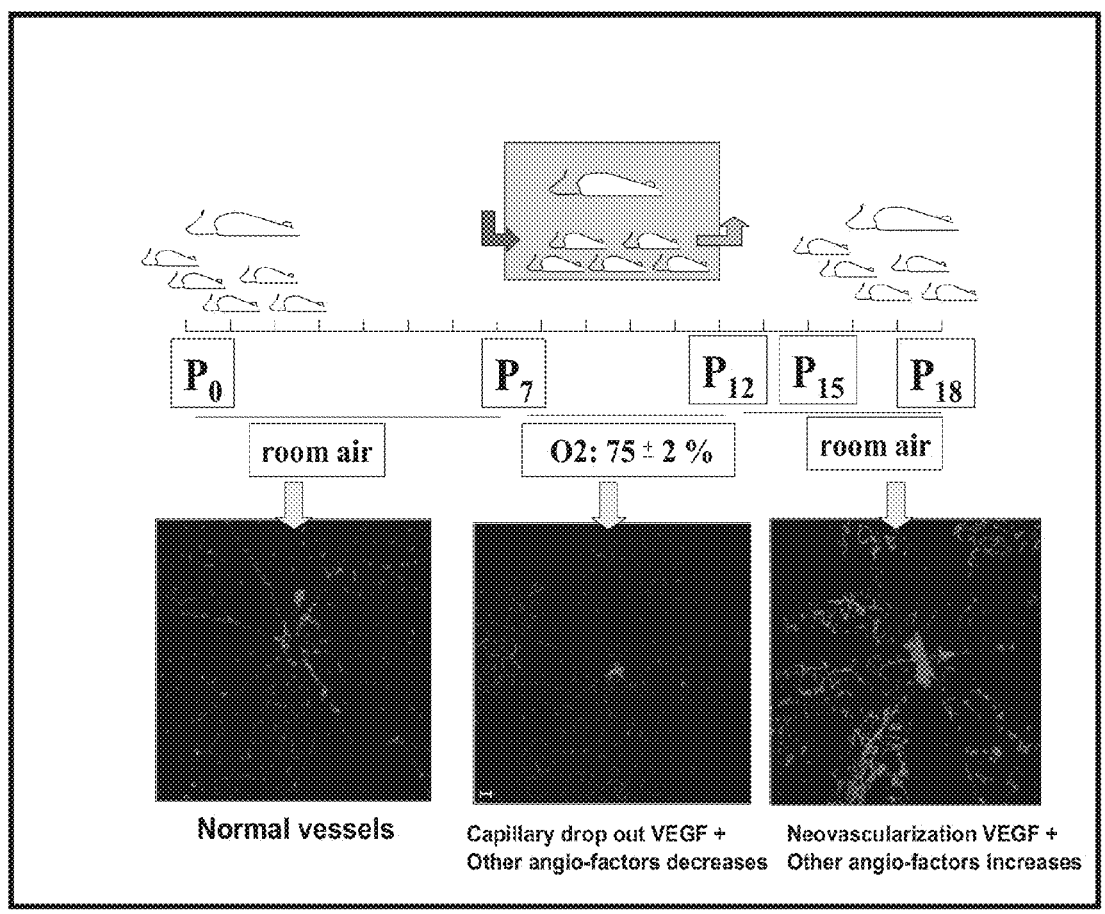

FIG. 21: depicts the induction of oxygen-induced retinopathy in a mouse mode and immunohistochemical staining of ROP mice indicating normal vessels in the eye at room air, capillary drop out due to decreased VEGF at 75% oxygen, and neovascularization due to increased VEGF and other angiogenic factors when mice are brought back to room air.

Figure 22:
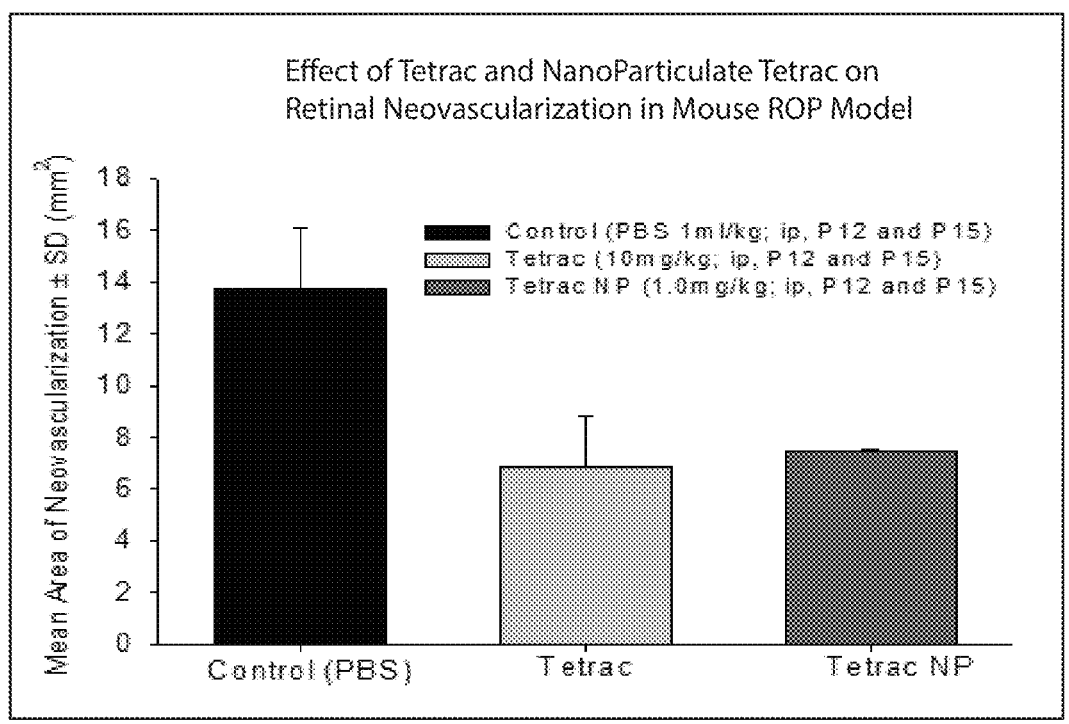

FIG. 22: depicts data representing the mean total area of neovascularization after the administration of tetrac at 10 mg/kg, IP or nano-tetrac at 1 mg/kg, IP on day 12 and 15. Tetrac and nano-tetrac resulted in approximately 50% inhibition of neovascularization.

Figure 23A:
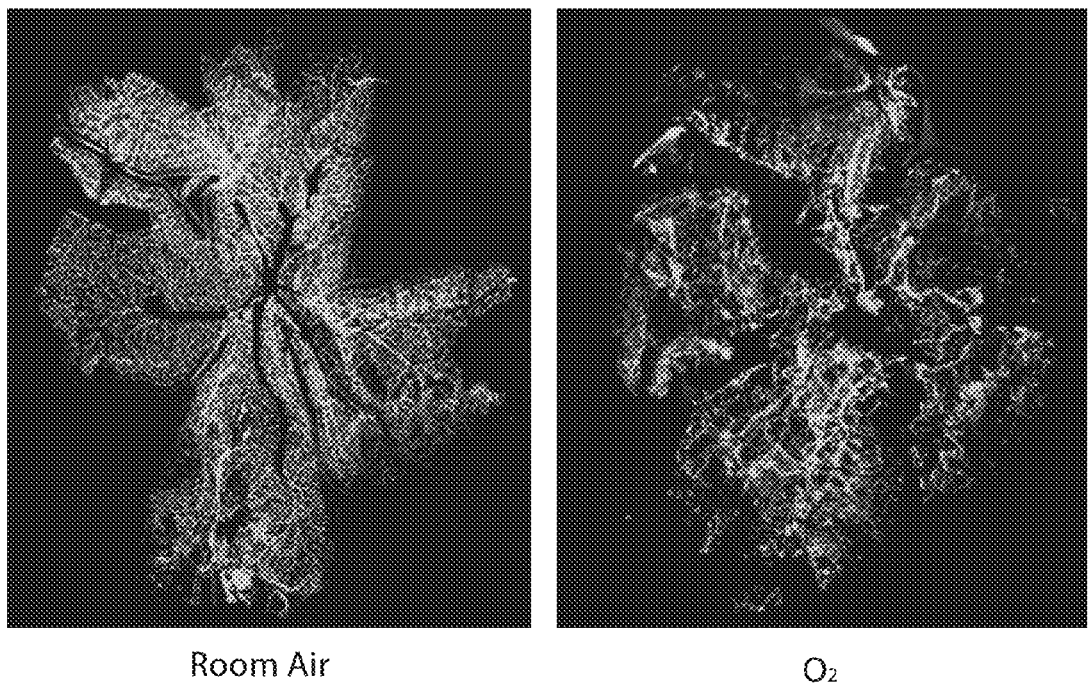

FIG. 23A: depicts the effects on mice pups after exposure to room air and 75% $O_2$ on vascularization area of murine retinas showing increased neovascularization.

Figure 23B:
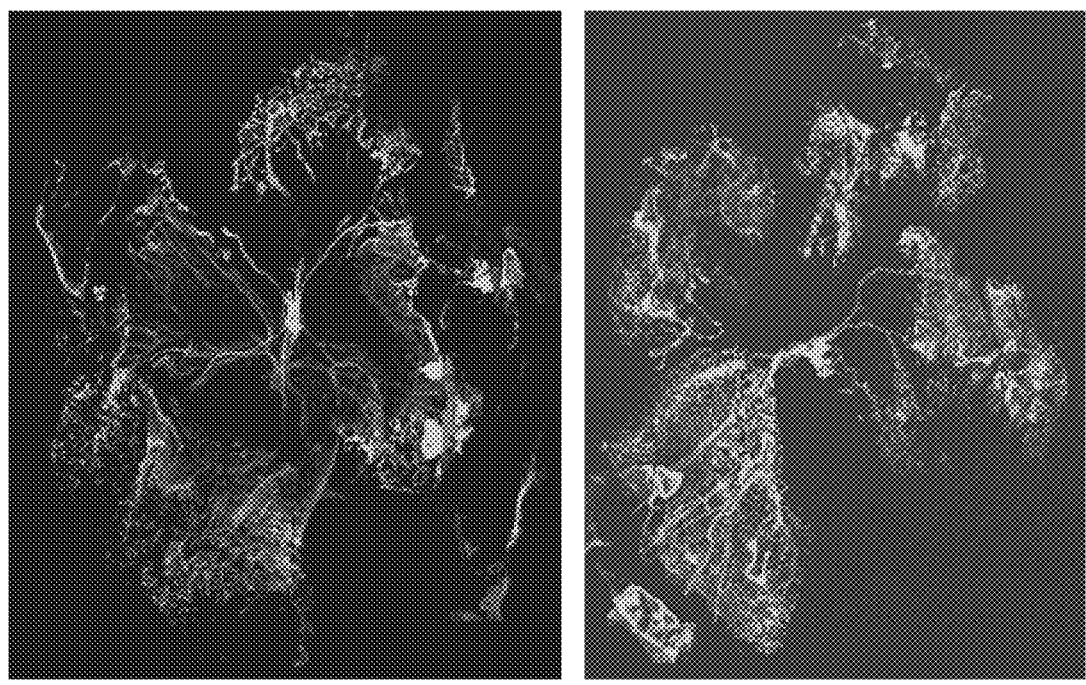

FIG. 23B: depicts the effects of injected tetrac nanoparticles and tetrac on vascularization area of murine retinas showing suppression of neovascularization.

Figure 24A:
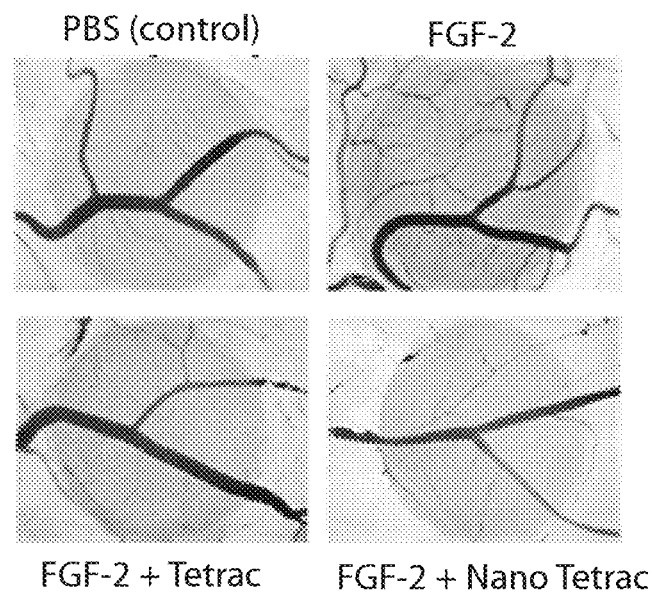

FIG. 24A: depicts photomicrographs of representative chick chorioallantoic membranes treated with tetrac and tetrac-nanoparticles at 2 µg/CAM.

Figure 24B:
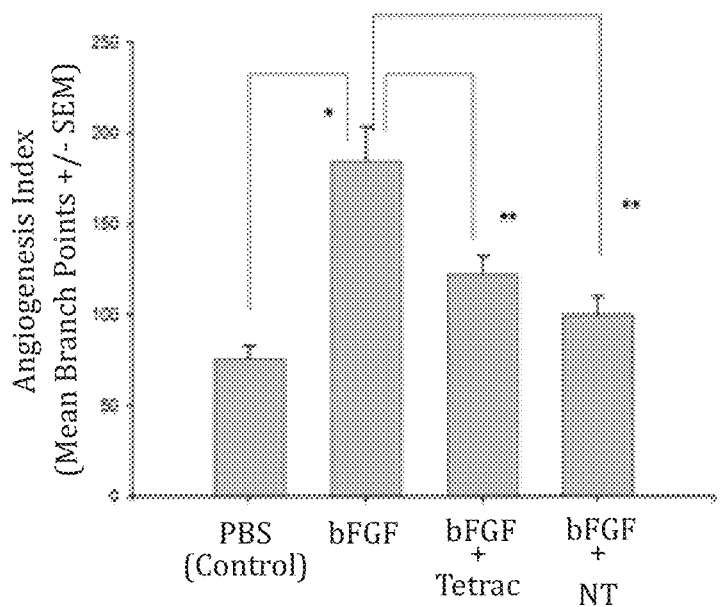

FIG. 24B: depicts graphically the quantification of the angiogenesis index of the micrographs described in FIG. 24A by quantification of angiogenic branch points under each treatment compared with the PBS control.

Figure 25:
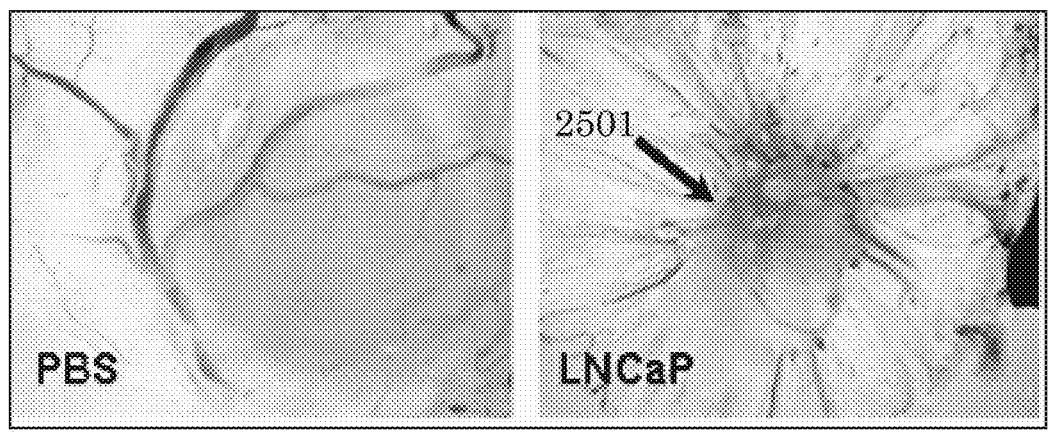

FIG. 25: depicts the CAM model of angiogenesis and a tumor implant, illustrating the induction of angiogenesis by LNCaP cancer cells implanted in matrigel.

Figure 26:
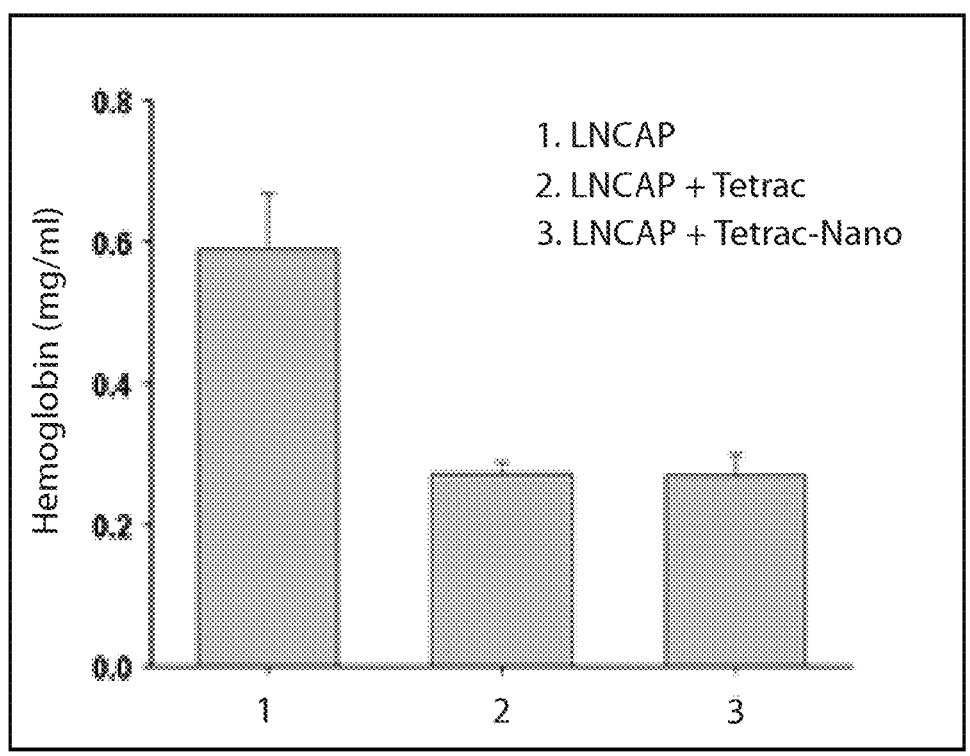

FIG. 26: depicts graphically the ability of tetrac and tetrac nanoparticles to inhibit tumor-induced angiogenesis by a determination of hemoglobin concentration.

Figure 27:
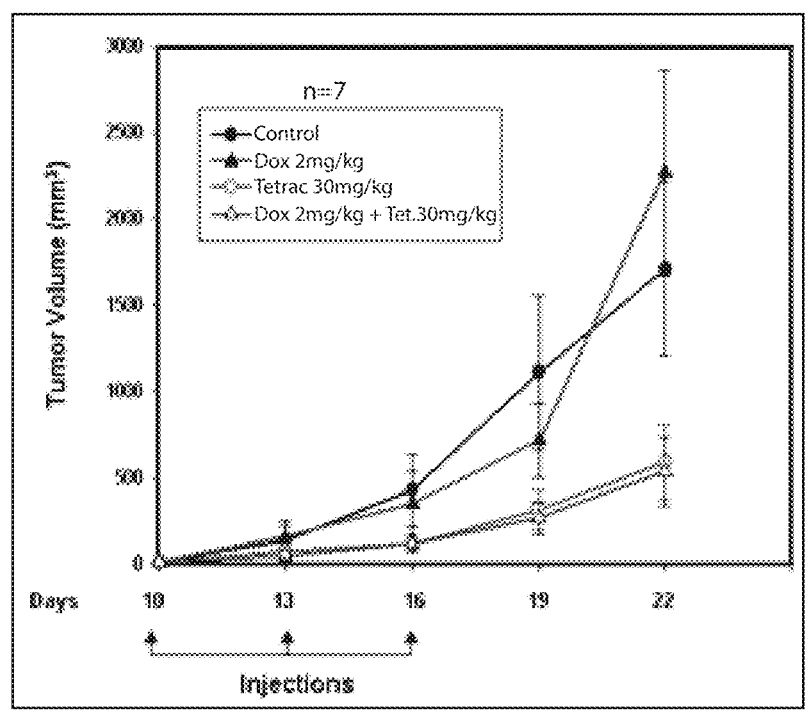

FIG. 27: depicts graphically the effects of tetrac on the proliferation of a drug resistant breast cancer xenograft.

Figure 28A:
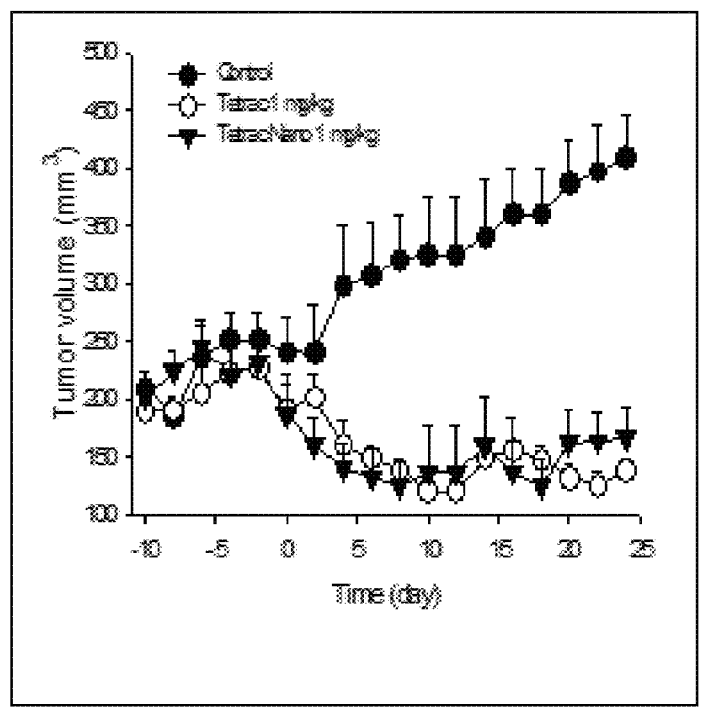

FIG. 28A: depicts the effects of tetrac and tetrac-PLGA nanoparticles on LNCaP tumor growth in male mice xenografts.

Figure 28B:
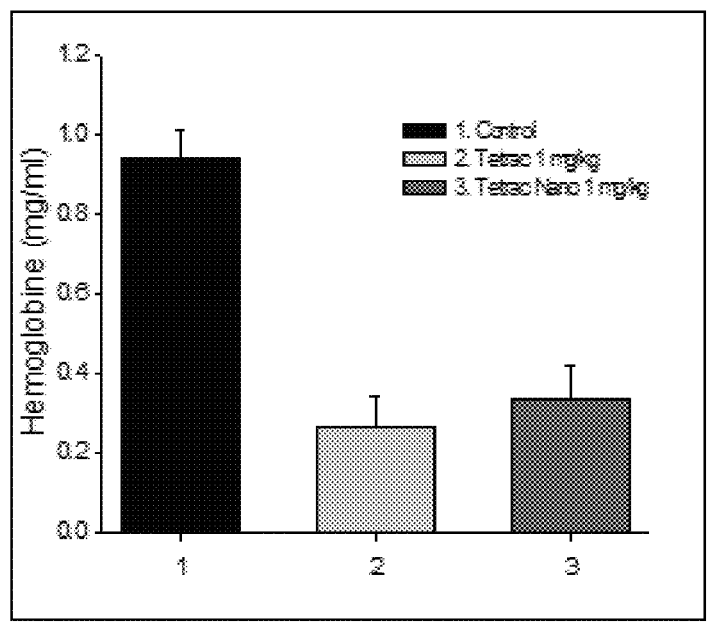

FIG. 28B: depicts the effects of tetrac and tetrac-PLGA nanoparticles on LNCaP tumor angiogenesis in male mice xenografts.

Figure 29:
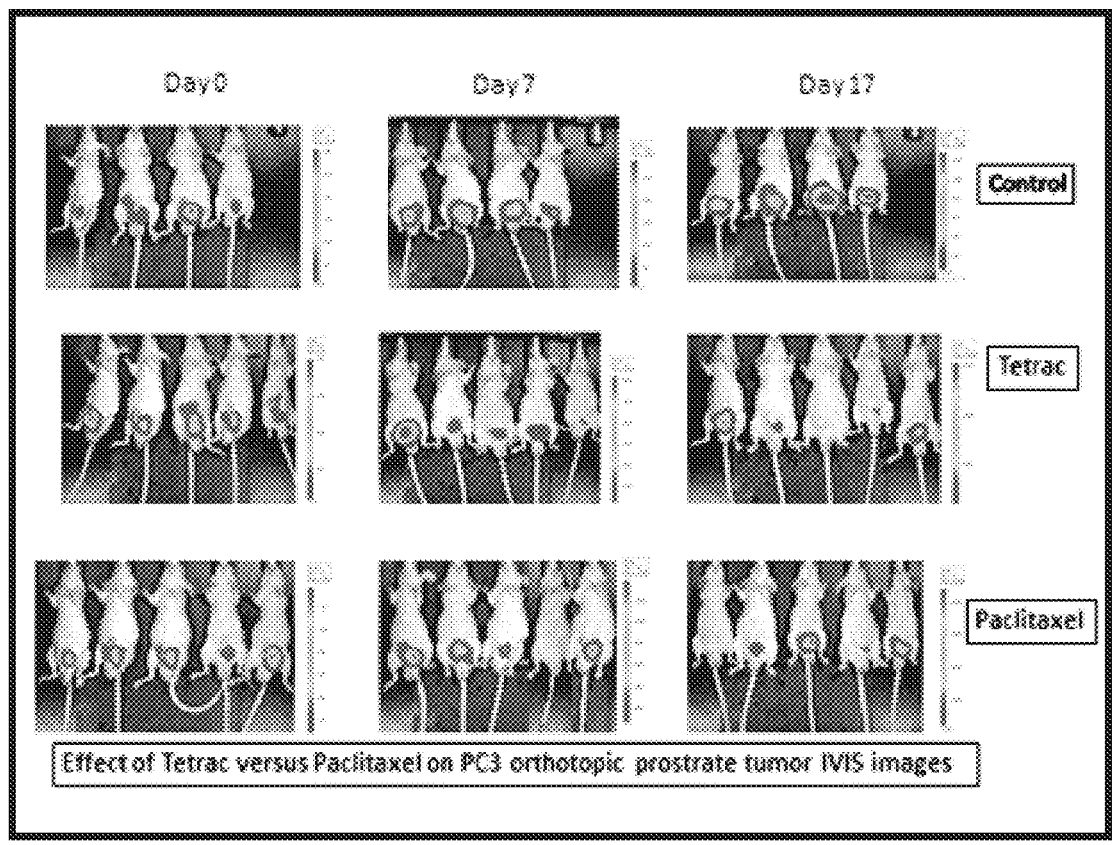

FIG. 29: depicts comparison of tetrac administered at 1 mg/kg daily for 17 days and paclitaxel administration for 17 days. Comparison shows distinct suppression of prostate tumor growth by tetrac comparable to the effects of the cytotoxic chemotherapeutic agent, paclitaxel.

Figure 30:
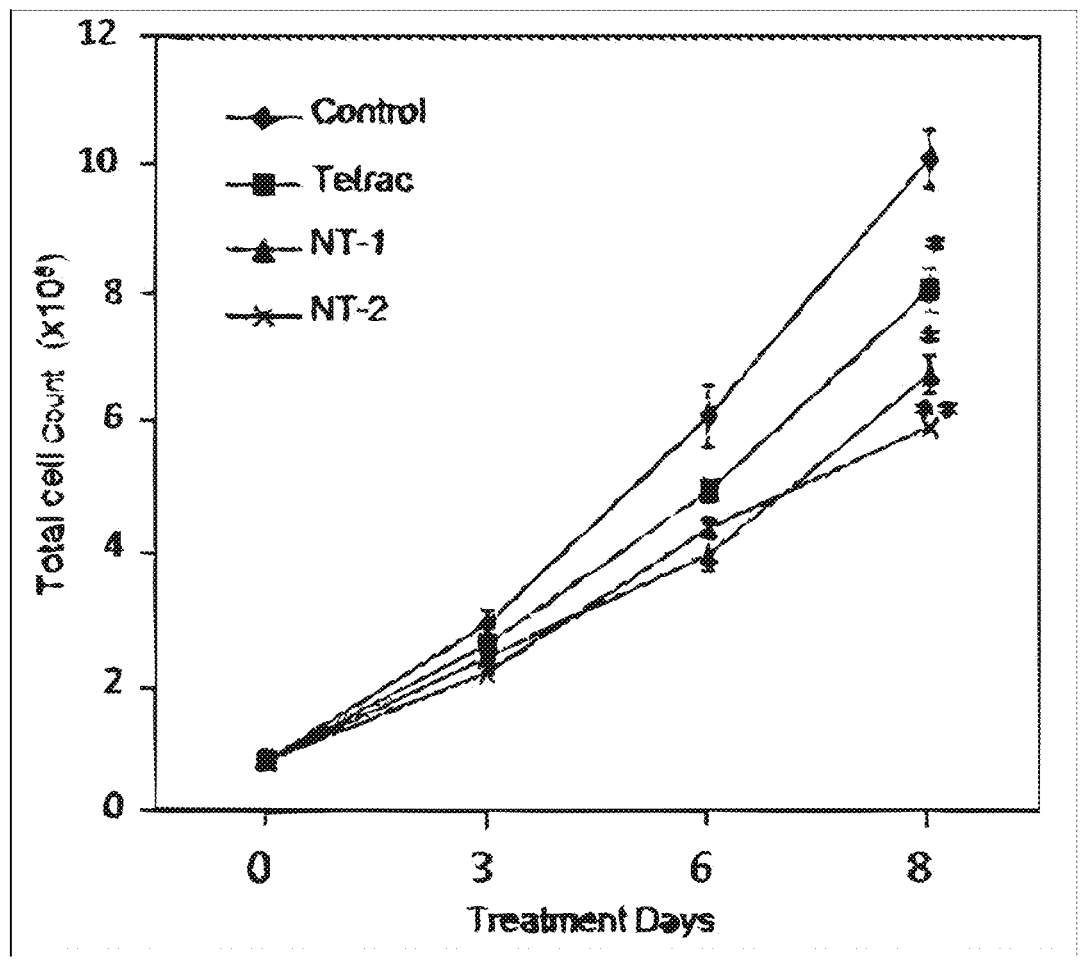

FIG. 30: depicts the effects of tetrac and tetrac-nanoparticles on the cell proliferation of pancreatic cancer, Panc-1 cells. Cells were cultured for 8 days in the presence of vehicle (control), tetrac, or nanoparticulate tetrac ("NT", wherein NT-1 and NT-2 denote separately prepared batches). Cells were counted on days 3, 6, and 8. By day 8, significant suppression of cell growth was observed in the tetrac-treated (*P<0.04) and NT-treated (**P≤0.01) samples, compared to untreated controls.

Figure 31A:
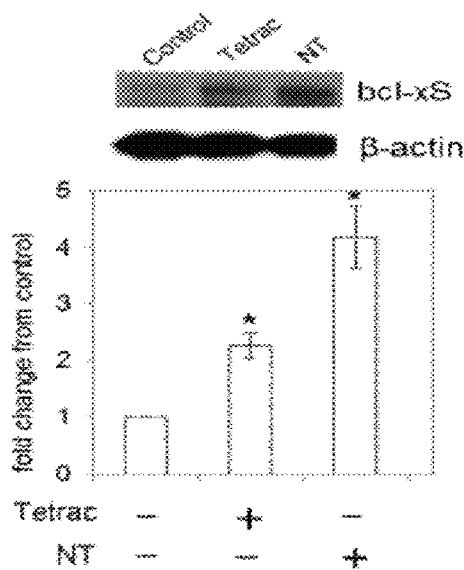

FIG. 31A: depicts the up-regulation of pro-apoptotic bcl-X's protein expression by tetrac and tetrac-nanoparticle administration. Total cell extracts from treated Panc-1 cells were analyzed by immunoblotting for bcl-Xs protein. Significant accumulation of bcl-Xs protein was observed with either unmodified tetrac or NT (*P<0.05).

Figure 31B:
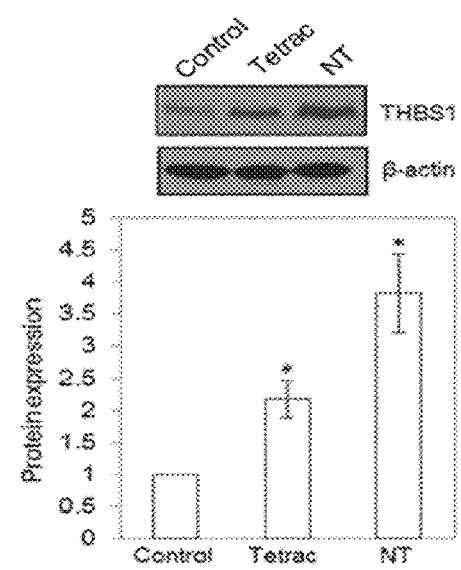

FIG. 31B: depicts the up-regulation of anti-angiogenic THBS1 protein expression by tetrac and tetrac-nanoparticle administration. Cells were treated for 3 days with control solvent, tetrac, or NT. Total cell lysates were probed for THBS1. Both tetrac (P<0.05) and NT (P<0.01) increased the levels of THBS1.

Figure 31C:
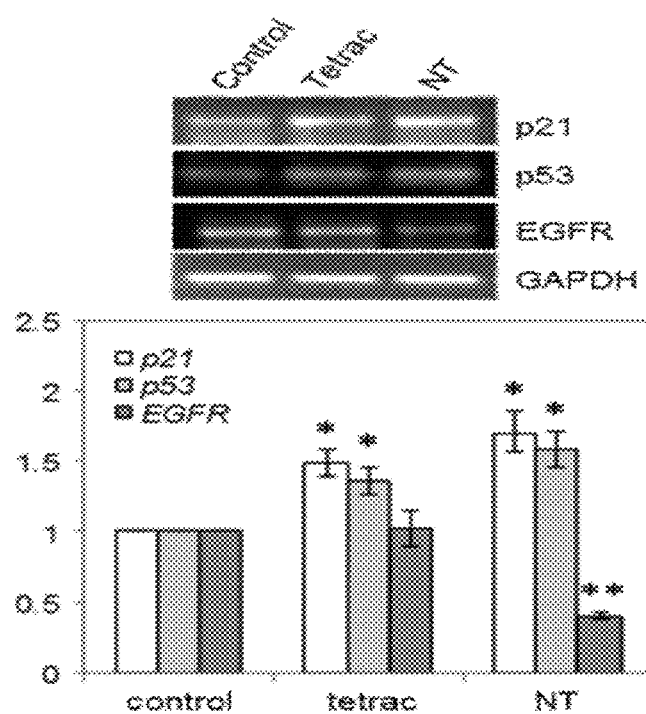

FIG. 31C: depicts the up-regulation of cell cycle gene expression to slow proliferation by the administration of tetrac and tetrac-nanoparticles. Total RNA was used as the template for RT-PCR. Treatment of cells with either tetrac or nanoparticulate tetrac decreased p21 and p53 mRNA expression (p<0.05) and nanoparticulate tetrac alone significantly reduced EGFR expression levels.

Figure 32A:
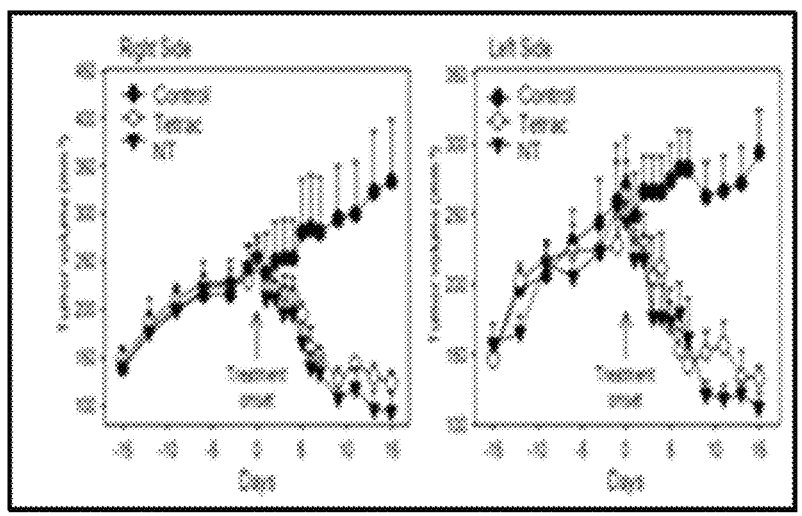

FIG. 32A: depicts graphically, the anti-tumorigenic effects of tetrac and tetrac-nanoparticles on pancreatic xenografts of AsPc-1 cells by comparing the tumor volumes over a 15 day treatment period.

Figure 32B:
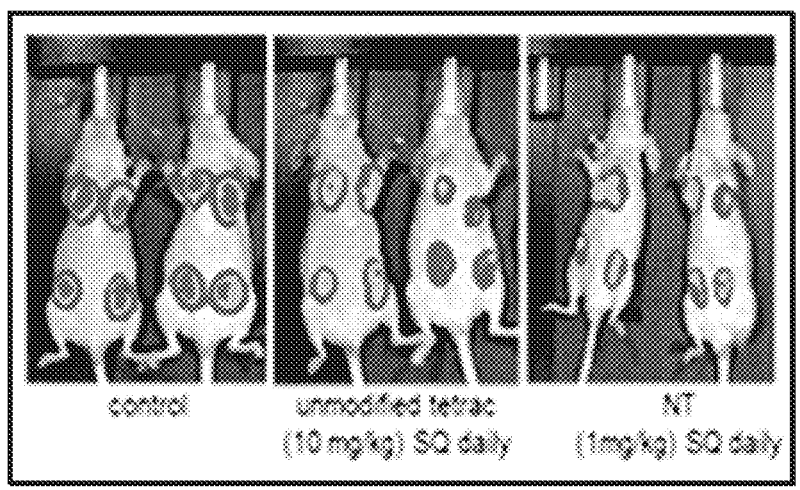

FIG. 32B: depicts a comparison of IVIS imaging of tumor masses of FIG. 32A on day 15 after the final measurement was taken.

Figure 32C:
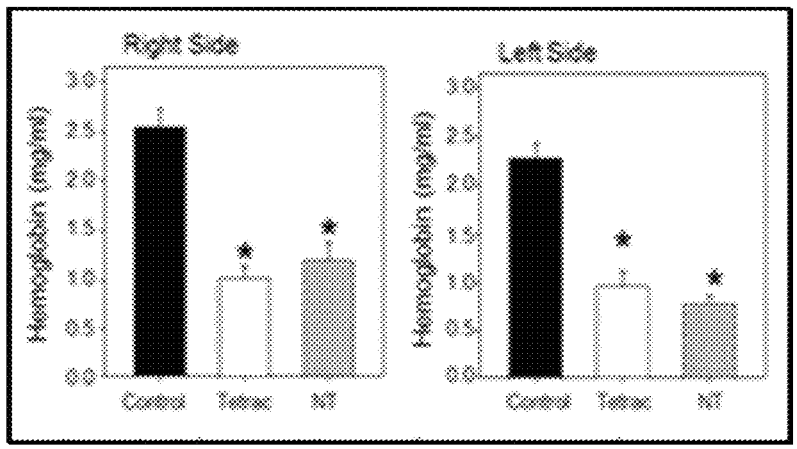

FIG. 32C: depicts the hemoglobin content as an index of tumor angiogenesis for the AsPc-1 cells xenografts depicted in FIG. 32A. The hemoglobin content decreased by 60% in animals treated for 15 days with either tetrac or tetrac-nanoparticles.

Figure 33:
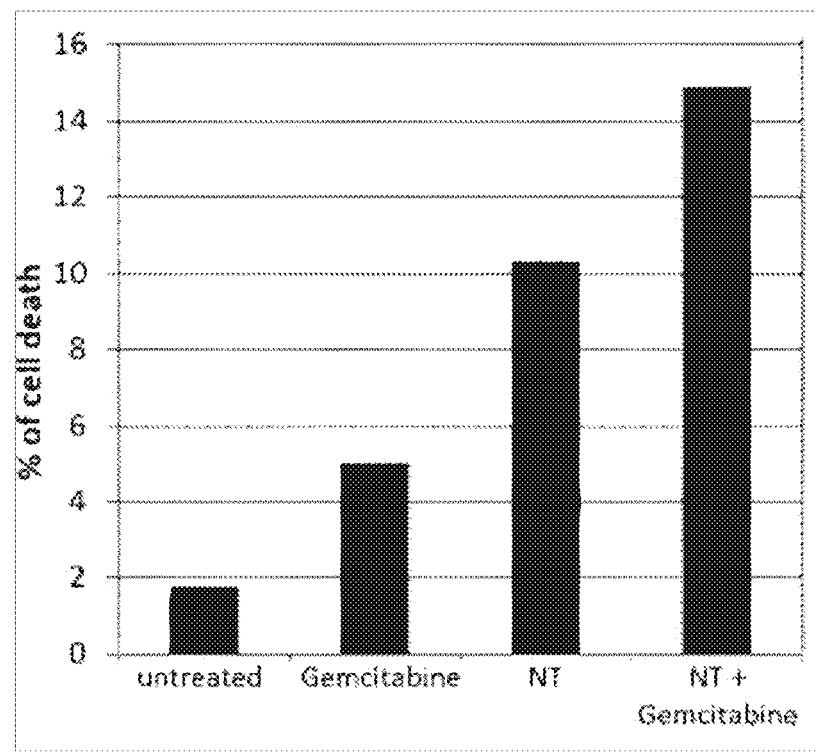

FIG. 33: depicts graphically the percentage of cell death of AsPc-1 cells resistant to Gemcitabine, comparing untreated, Gemcitabine, tetrac-nanoparticles, and tetrac-nanoparticles+Gemcitabine combination treatment.

Figure 34:
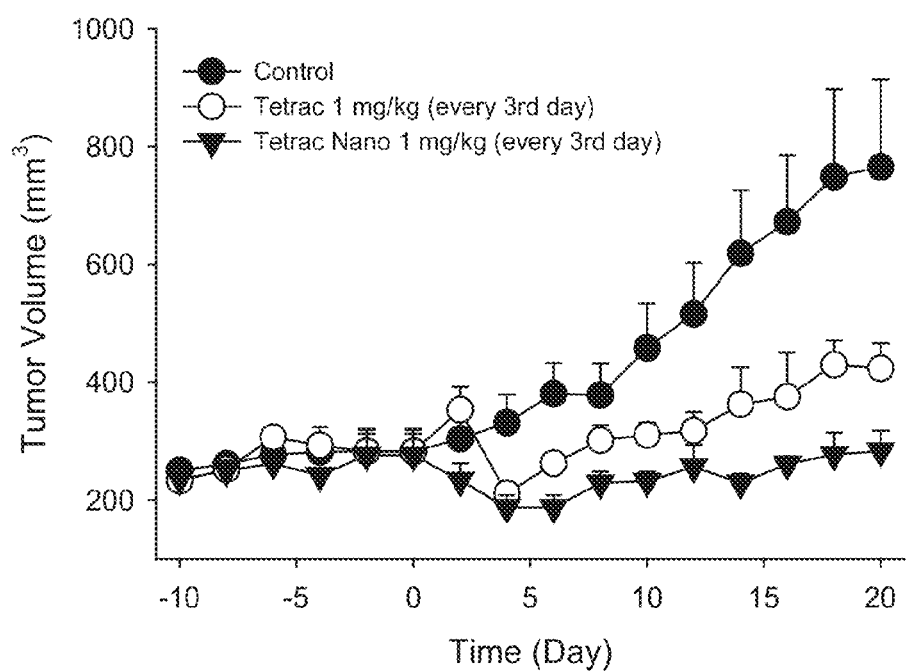

FIG. 34: depicts graphically the effects of tetrac and tetrac nanoparticles on primary and metastatic non-small cell lung cancer tumor volume.

Figure 35A:
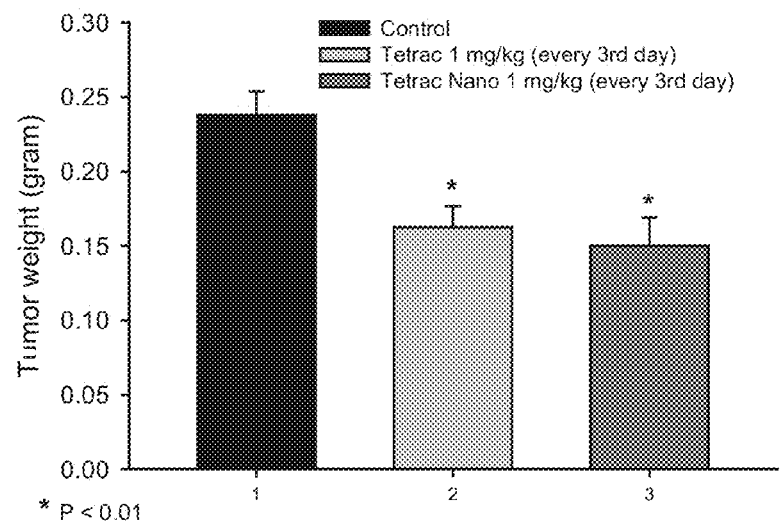

FIG. 35A: depicts graphically the effects of tetrac and tetrac nanoparticles on primary and metastatic non-small cell lung cancer tumor weight.

Figure 35B:
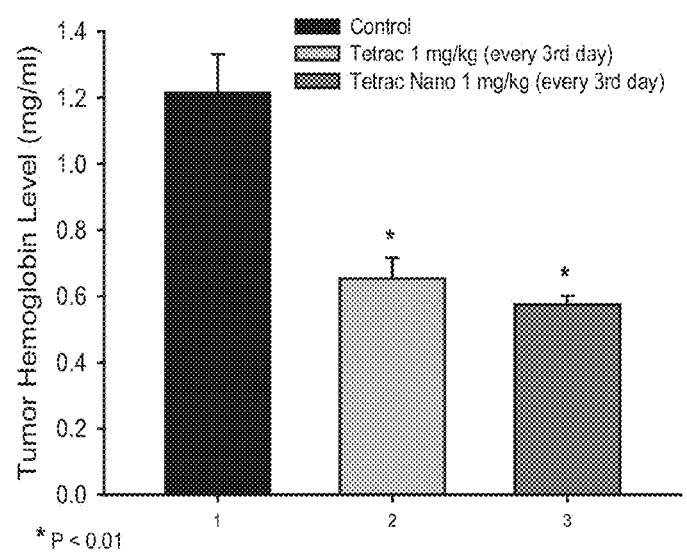

FIG. 35B: depicts graphically the effects of tetrac and tetrac nanoparticles on primary and metastatic non-small cell lung cancer tumor hemoglobin content.

Figure 36A:
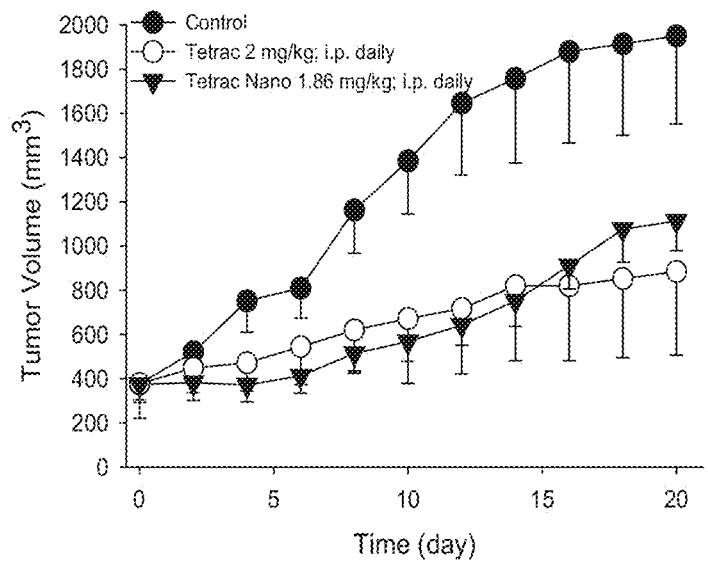

FIG. 36A: depicts graphically the effects of tetrac and tetrac nanoparticles on the tumor volume of $10\times10^6$ primary and metastatic lung cancer cells.

Figure 36B:
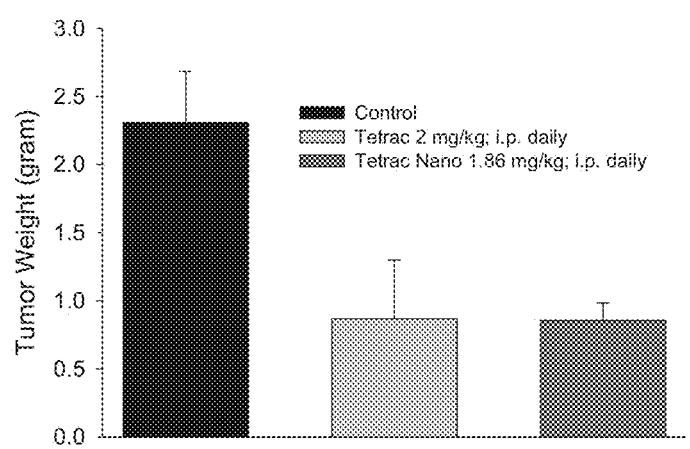

FIG. 36B: depicts graphically the effects of tetrac and tetrac nanoparticles on the tumor weight of $10\times10^6$ primary and metastatic lung cancer cells.

Figure 37A:
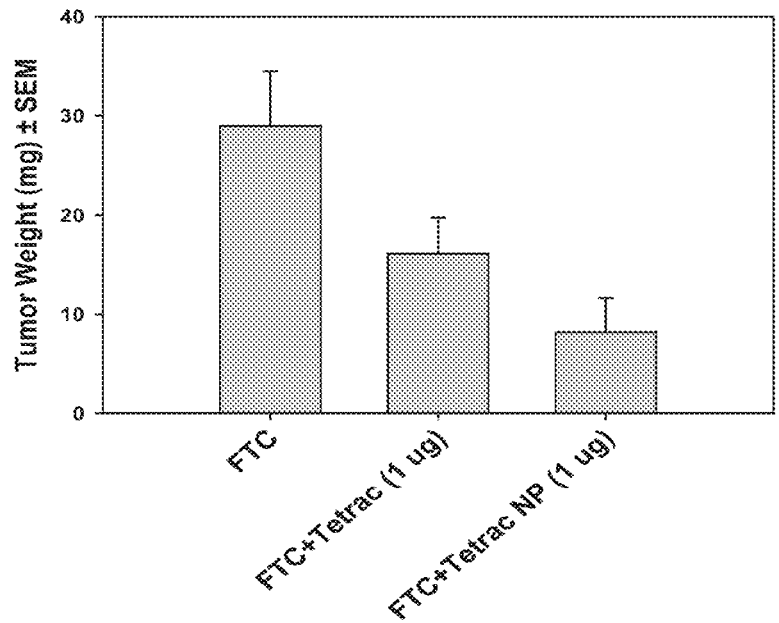

FIG. 37A: depicts graphically the effects of tetrac and tetrac nanoparticles at 1 µg on the weight of primary and metastatic follicular thyroid carcinoma (FTC) tumors in the CAM model.

Figure 37B:
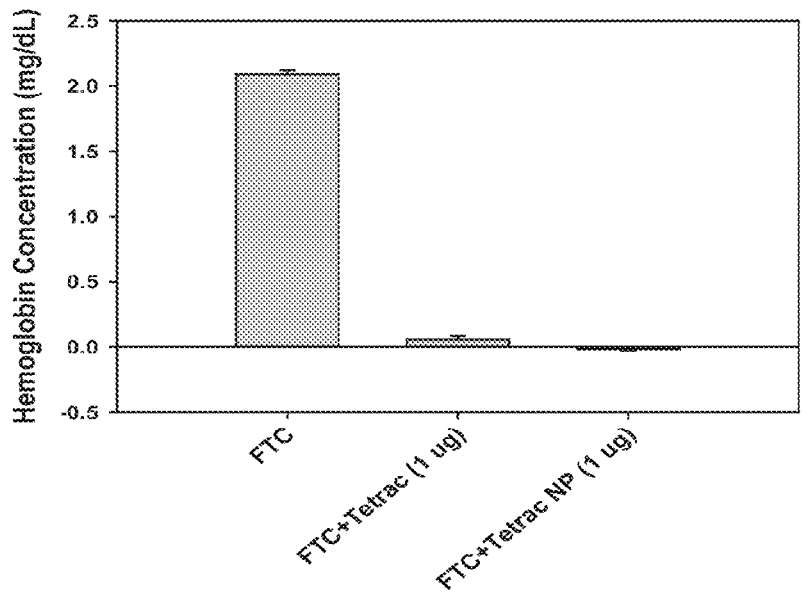

FIG. 37B: depicts graphically the effects of tetrac and tetrac nanoparticles 1 µg on hemoglobin content of primary and metastatic follicular thyroid carcinoma (FTC) tumors in the CAM model.

Figure 37C:
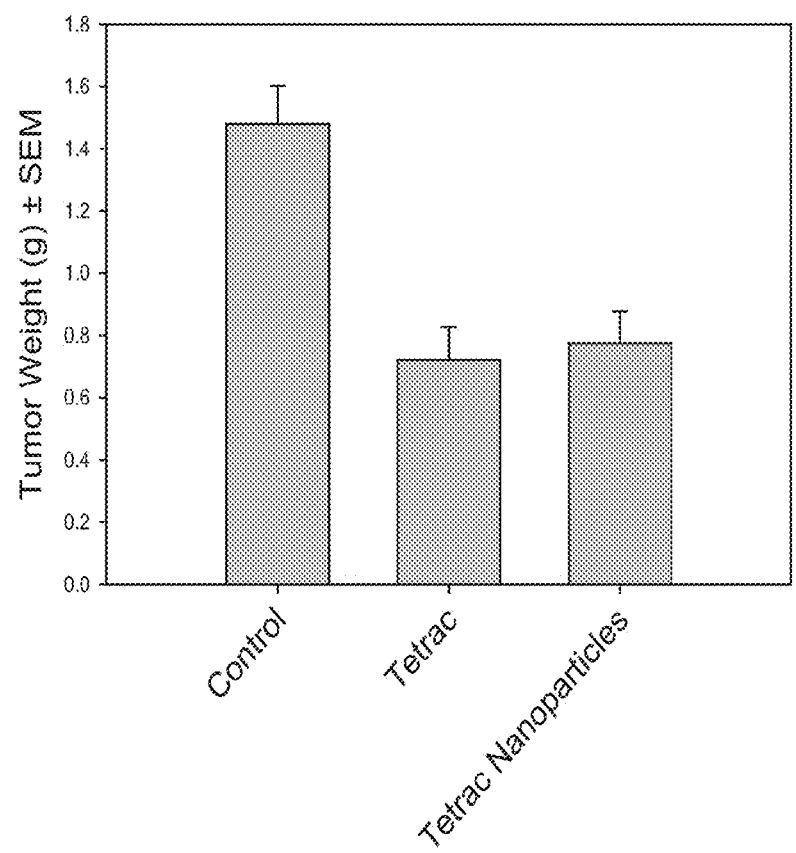

FIG. 37C: depicts graphically the effects of tetrac and tetrac nanoparticles on the tumor weight of primary and metastatic follicular thyroid carcinoma (FTC) tumors.

Figure 38A:
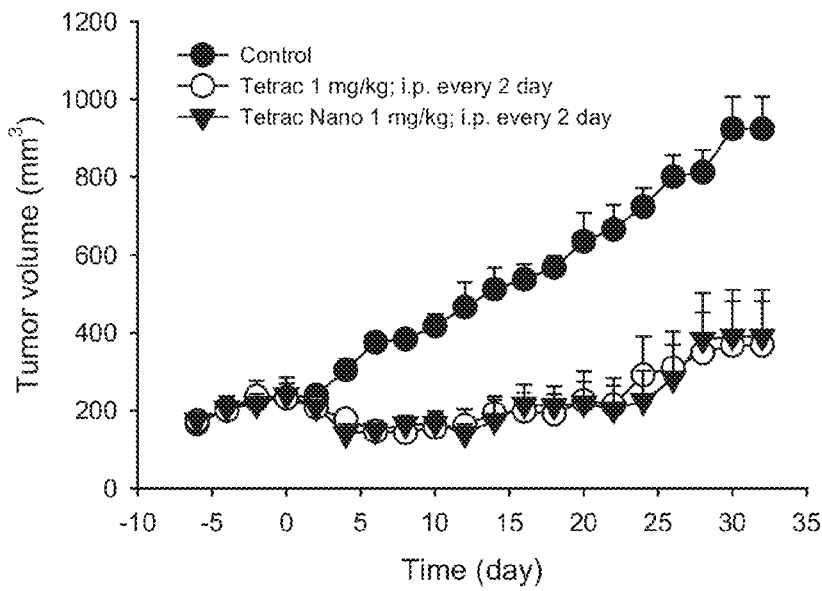

FIG. 38A: depicts graphically the effects of tetrac and tetrac nanoparticles on the tumor volume of primary and metastatic human follicular tumors growth in nude mice xenografts.

Figure 38B:
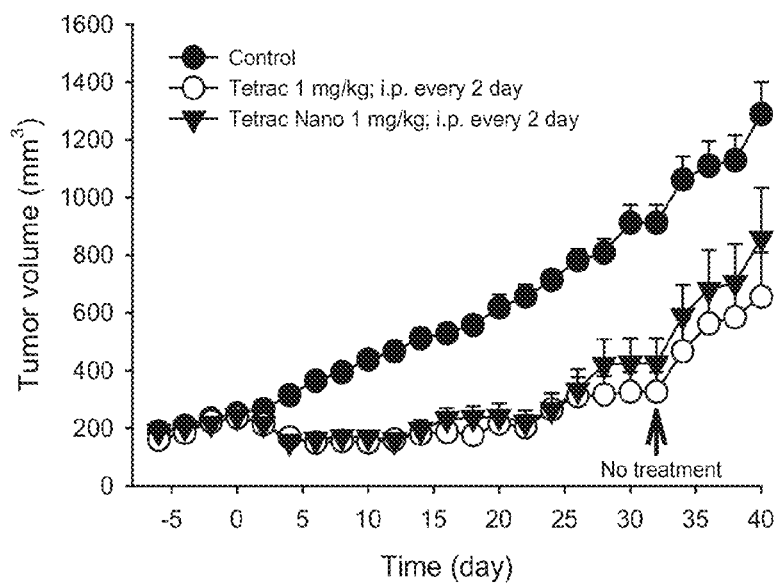

FIG. 38B: depicts graphically the tumor regrowth after discontinuing the tetrac and tetrac nanoparticles in FIG. 38A.

Figure 39A:
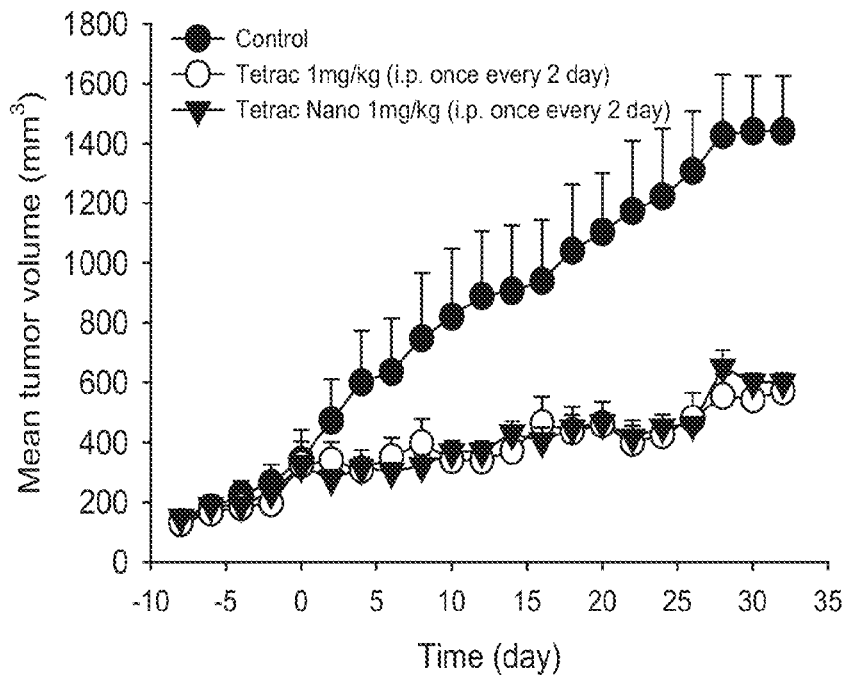

FIG. 39A: depicts graphically the effects of tetrac and tetrac nanoparticles on the tumor volume of primary and metastatic renal tumors in nude mice xenografts.

Figure 39B:
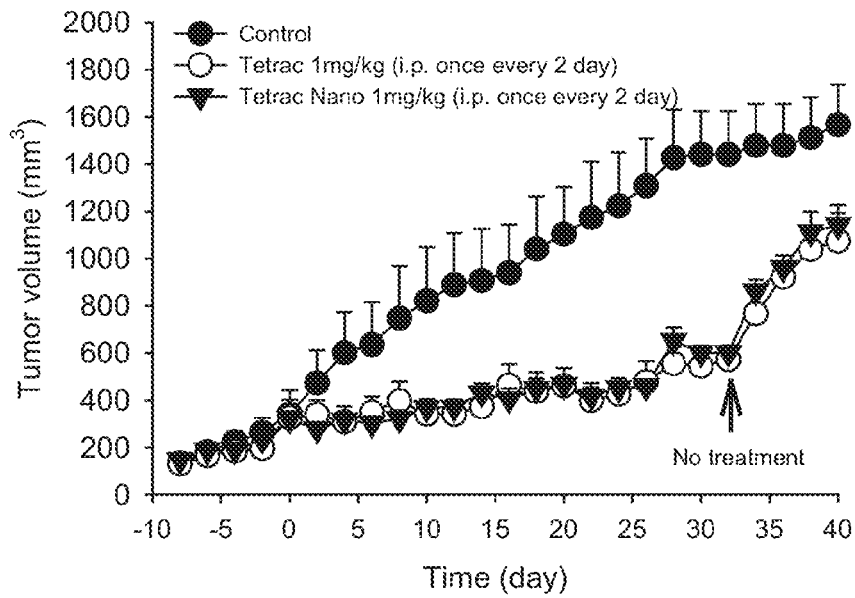

FIG. 39B: depicts graphically tumor regrowth after discontinuing treatment with tetrac and tetrac nanoparticles as depicted in FIG. 39A.

Figure 40A:
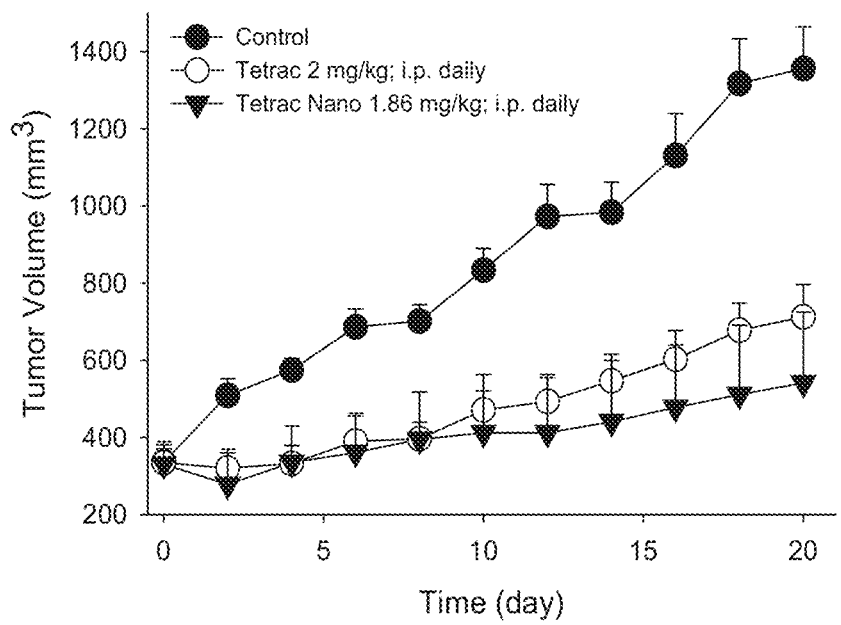

FIG. 40A: depicts graphically the effects of tetrac and tetrac nanoparticles on the tumor volume of renal cell carcinoma primary and metastatic tumors.

Figure 40B:
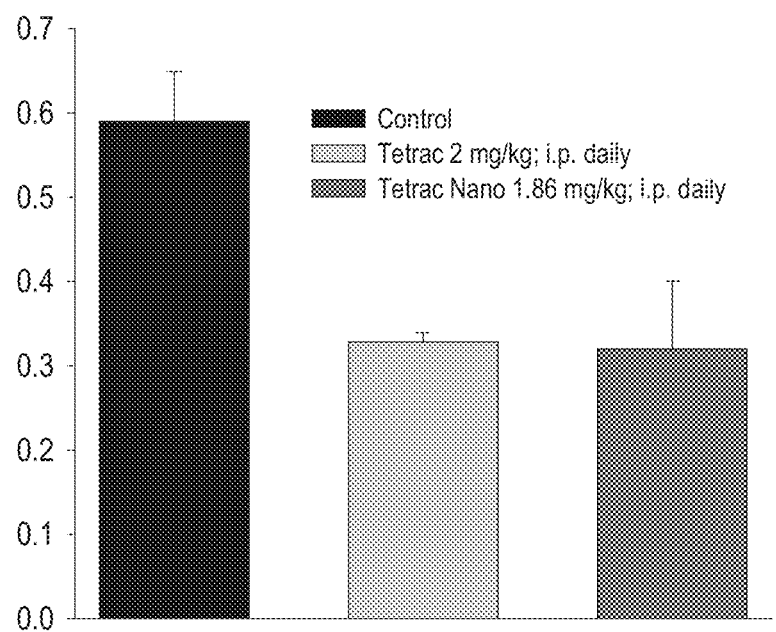

FIG. 40B: depicts graphically the effects of tetrac and tetrac nanoparticles on the tumor weight of renal cell carcinoma primary and metastatic tumors.

DETAILED DESCRIPTION OF THE INVENTION

The features and other details of the invention will now be more particularly described with references to the accompanying drawings, and as pointed out by the claims. For convenience, certain terms used in the specification, examples and claims are collected here. Unless otherwise defined, all technical and scientific terms used herein have the same meaning as commonly understood by one of ordinary skill in the art to which this invention pertains.

As used herein, the term "angiogenic agent" includes any compound or substance that promotes or encourages angiogenesis, whether alone or in combination with another substance. Examples include, but are not limited to, T3, T4, T3-agarose or T4-agarose, polymeric analogs of T3, T4, 3,5-dimethyl-4-(4'-hydroxy-3'-isopropylbenzyl)-phenoxy acetic acid (GC-1), or DITPA. In contrast, the terms "anti-angiogenesis agent" or "anti-angiogenic agent" refer to any compound or substance that inhibits or discourages angiogenesis, whether alone or in combination with another substance. Examples include, but are not limited to, tetrac, triac, XT 199, and mAb LM609.

As used herein, the term "myocardial ischemia" is defined as an insufficient blood supply to the heart muscle caused by a decreased capacity of the heart vessels. As used herein, the term "coronary disease" is defined as diseases/disorders of cardiac function due to an imbalance between myocardial function and the capacity of coronary vessels to supply sufficient blood flow for normal function. Specific coronary diseases/disorders associated with coronary disease which can be treated with the compositions and methods described herein include myocardial ischemia, angina pectoris, coronary aneurysm, coronary thrombosis, coronary vasospasm, coronary artery disease, coronary heart disease, coronary occlusion and coronary stenosis.

As used herein the term "occlusive peripheral vascular disease" (also known as peripheral arterial occlusive disorder) is a vascular disorder-involving blockage in the carotid or femoral arteries, including the iliac artery. Blockage in the femoral arteries causes pain and restricted movement. A specific disorder associated with occlusive peripheral vascular disease is diabetic foot, which affects diabetic patients, often resulting in amputation of the foot.

As used herein the terms "regeneration of blood vessels," "angiogenesis," "revascularization," and "increased collateral circulation" (or words to that effect) are considered as synonymous. The term "pharmaceutically acceptable" when referring to a natural or synthetic substance means that the substance has an acceptable toxic effect in view of its much greater beneficial effect, while the related term, "physiologically acceptable," means the substance has relatively low toxicity. The term, "co-administered" means two or more drugs are given to a patient at approximately the same time or in close sequence so that their effects run approximately concurrently or substantially overlap. This term includes sequential as well as simultaneous drug administration.

"Pharmaceutically acceptable salts" refers to pharmaceutically acceptable salts of thyroid hormone analogs, polymeric forms, and derivatives, which salts are derived from a variety of organic and inorganic counter ions well known in the art and include, by way of example only, sodium, potassium, calcium, magnesium, ammonium, tetra-alkyl ammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt.

"Subject" includes living organisms such as humans, monkeys, cows, sheep, horses, pigs, cattle, goats, dogs, cats, mice, rats, cultured cells therefrom, and transgenic species thereof. In a preferred embodiment, the subject is a human. Administration of the compositions of the present invention to a subject to be treated can be carried out using known procedures, at dosages and for periods of time effective to treat the condition in the subject. An effective amount of the therapeutic compound necessary to achieve a therapeutic effect may vary according to factors such as the age, sex, and weight of the subject, and the ability of the therapeutic compound to treat the foreign agents in the subject. Dosage regimens can be adjusted to provide the optimum therapeutic response. For example, several divided doses may be administered daily or the dose may be proportionally reduced as indicated by the exigencies of the therapeutic situation.

"Administering" includes routes of administration which allow the compositions of the invention to perform their intended function, e.g., promoting angiogenesis. A variety of routes of administration are possible including, but not necessarily limited to parenteral (e.g., intravenous, intra-arterial, intramuscular, subcutaneous injection), oral (e.g., dietary), topical, nasal, rectal, intratumoral (direct injection into the tumor site), intraocular, or via slow releasing microcarriers depending on the disease or condition to be treated. Oral, parenteral and intravenous administration are preferred modes of administration. Formulation of the compound to be administered will vary according to the route of administration selected (e.g., solution, emulsion, gels, aerosols, capsule). An appropriate composition comprising the compound to be administered can be prepared in a physiologically acceptable vehicle or carrier and optional adjuvants and preservatives. For solutions or emulsions, suitable carriers include, for example, aqueous or alcoholic/aqueous solutions, emulsions or suspensions, including saline and buffered media, sterile water, creams, ointments, lotions, oils, pastes, and solid carriers. Parenteral vehicles can include sodium chloride solution, Ringer's dextrose, dextrose and sodium chloride, lactated Ringer's, or fixed oils. Intravenous vehicles can include various additives, preservatives, or fluid, nutrient or electrolyte replenishers (See generally, *Remington's Pharmaceutical Science,* 16th Edition, Mack, Ed. (1980)).

"Effective amount" includes those amounts of pro-angiogenic or anti-angiogenic compounds which allow it to perform its intended function, e.g., promoting or inhibiting angiogenesis in angiogenesis-related disorders as described herein. The effective amount will depend upon a number of factors, including biological activity, age, body weight, sex, general health, severity of the condition to be treated, as well as appropriate pharmacokinetic properties. For example, dosages of the active substance may be from about 0.01 mg/kg/day to about 500 mg/kg/day, advantageously from about 0.1 mg/kg/day to about 100 mg/kg/day. A therapeutically effective amount of the active substance can be administered by an appropriate route in a single dose or multiple doses. Further, the dosages of the active substance can be proportionally increased or decreased as indicated by the exigencies of the therapeutic or prophylactic situation.

"Pharmaceutically acceptable carrier" includes any and all solvents, dispersion media, coatings, antibacterial and antifungal agents, isotonic and absorption delaying agents, and the like which are compatible with the activity of the compound and are physiologically acceptable to the subject. An example of a pharmaceutically acceptable carrier is buffered normal saline (0.15M NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

"Additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described.

Compositions

Disclosed herein are angiogenic agents comprising thyroid hormones, analogs thereof, and polymer conjugations of the hormones and their analogs. The disclosed compositions can be used for promoting angiogenesis to treat disorders wherein angiogenesis is beneficial. Additionally, the inhibition of these thyroid hormones, analogs and polymer conjugations can be used to inhibit angiogenesis to treat disorders associated with such undesired angiogenesis. As used herein, the term "angiogenic agent" includes any compound or substance that promotes or encourages angiogenesis, whether alone or in combination with another substance. Examples include, but are not limited to, T3, T4, T3-agarose or T4-agarose, polymeric analogs of T3, T4, 3,5-dimethyl-4-(4'-hydroxy-3'-isopropylbenzyl)-phenoxyl acetic acid (GC-1), or DITPA.

Polymer conjugations are used to improve drug viability. While old and new therapeutics are well-tolerated, many compounds need advanced drug discovery technologies to decrease toxicity, increase circulatory time, or modify biodistribution. One strategy for improving drug viability is the utilization of water-soluble polymers. Various water-soluble polymers have been shown to modify biodistribution, improve the mode of cellular uptake, change the permeability through physiological barriers, and modify the rate of clearance through the body. To achieve either a targeting or sustained-release effect, water-soluble polymers have been synthesized that contain drug moieties as terminal groups, as part of the backbone, or as pendent groups on the polymer chain.

Representative compositions of the present invention include thyroid hormone or analogs thereof conjugated to polymers. Conjugation with polymers can be either through covalent or non-covalent linkages. In preferred embodiments, the polymer conjugation can occur through an ester, ether, anhydride, or sulfhydryl linkage. Representative compositions of the present invention include thyroid hormone or analogs thereof conjugated to polymers. Conjugation with polymers can be either through covalent (i.e., ester, ether, sulfhydryl, or anhydride linkages) or non-covalent linkages. (See WO2008/140507, incorporated herein by reference, for specific examples).

An example of a polymer conjugation through an ester linkage using polyvinyl alcohol is shown in FIG. 17. In this preparation commercially available polyvinyl alcohol (or related co-polymers) can be esterified by treatment with the acid chloride of thyroid hormone analogs, including the acid chloride form. The hydrochloride salt is neutralized by the addition of triethylamine to afford triethylamine hydrochloride which can be washed away with water upon precipitation of the thyroid hormone ester polymer form for different analogs. The ester linkage may stabilize the conjugated thyroid hormone analog nanoparticle and avoid local or systemic release of free thyroid hormone. Local release of unmodified thyroid hormone may be undesired because of its intracellular effects on mitochondrial energetics.

An example of a polymer conjugation through an anhydride linkage using acrylic acid ethylene co-polymer is shown in FIG. 18. This is similar to the previous polymer covalent conjugation, however, this time it is through an anhydride linkage that is derived from reaction of an acrylic acid co-polymer. Neutralization of the hydrochloric acid is accomplished by treatment with triethylamine and subsequent washing of the precipitated polyanhydride polymer with water removes the triethylamine hydrochloride byproduct. This reaction will lead to the formation of thyroid hormone analog acrylic acid co-polymer+triethylamine. Similar to the ester linkage, the anhydride linkage may also stabilize the conjugated thyroid hormones and avoid local or systemic release of free thyroid hormone. Instead the conjugated thyroid hormone will act at the cell surface receptor $\alpha V\beta 3$ and it will not produce the intracellular effects observed by unmodified thyroid hormones and analogs.

Another representative polymer conjugation includes thyroid hormone or its analogs conjugated to polyethylene glycol (PEG). Attachment of PEG to various drugs, proteins and liposomes has been shown to improve residence time and decrease toxicity. PEG can be coupled to active agents through the hydroxyl groups at the ends of the chains and via other chemical methods. Peg itself, however, is limited to two active agents per molecule. In a different approach, copolymers of PEG and amino acids were explored as novel biomaterials which would retain the biocompatibility properties of PEG, but which would have the added advantage of numerous attachment points per molecule and which could be synthetically designed to suit a variety of applications.

Another representative polymer conjugation includes thyroid hormone or its analogs in non-covalent conjugation with polymers. This is shown in detail in FIG. 19. A preferred non-covalent conjugation is entrapment of thyroid hormone or analogs thereof in a polylactic acid polymer. Polylactic acid polyester polymers (PLA) undergo hydrolysis in vivo to the lactic acid monomer and this has been exploited as a vehicle for drug delivery systems in humans. Unlike the prior two covalent methods where the thyroid hormone analog is linked by a chemical bond to the polymer, this would be a non-covalent method that would encapsulate the thyroid hormone analog into PLA polymer beads. This reaction will lead to the formation of thyroid hormone analog containing PLA beads in water. Filtering and washing will result in the formation of thyroid hormone analog containing PLA beads, which upon in vivo hydrolysis will lead to the generation of controlled levels of thyroid hormone plus lactic acid.

Furthermore, nanotechnology can be used for the creation of useful materials and structures sized at the nanometer scale. The main drawback with biologically active substances is fragility. Nanoscale materials can be combined with such biologically active substances to dramatically improve the durability of the substance, create localized high concentrations of the substance, and reduce costs by minimizing losses. Therefore, additional polymeric conjugations include nanoparticle formulations of thyroid hormones and analogs thereof. In such an embodiment, nano-polymers and nanoparticles can be used as a matrix for local delivery of thyroid hormone and its analogs. This will aid in time controlled delivery into the cellular and tissue target.

Compositions of the present invention include thyroid hormone, analogs, and derivatives either alone or in covalent or non-covalent conjugation with polymers. Examples of representative analogs and derivatives are shown in FIG. 20, Tables A-D. Table A shows T2, T3, T4, and bromo-derivatives. Table B shows alanyl side chain modifications. Table C shows hydroxy groups, diphenyl ester linkages, and D-configurations. Table D shows tyrosine analogs.

The terms "anti-angiogenesis agent" or "anti-angiogenic agent" refer to any compound or substance that inhibits or discourages angiogenesis, whether alone or in combination with another substance. Examples include, but are not limited to, tetrac, triac, XT 199, and mAb LM609.

The Role of Thyroid Hormone, Analogs, and Polymeric Conjugations in Promoting Angiogenesis The pro-angiogenic effect of thyroid hormone analogs or polymeric forms depends upon a non-genomic initiation, as tested by the susceptibility of the hormonal effect to reduction by pharmacological inhibitors of the MAPK signal transduction pathway. Such results indicate that another consequence of activation of MAPK by thyroid hormone is new blood vessel growth. The latter is initiated non-genomically, but of course, requires a consequent complex gene transcription program. The ambient concentrations of thyroid hormone are relatively stable. The CAM model, at the time we tested it, was thyroprival and thus may be regarded as a system, which does not reproduce the intact organism.

The availability of a chick chorioallantoic membrane (CAM) assay for angiogenesis has provided a model in which to quantitate angiogenesis and to study possible mechanisms involved in the induction by thyroid hormone of new blood vessel growth. The present application discloses a pro-angiogenic effect of T4 that approximates that in the CAM model of FGF2 and that can enhance the action of suboptimal doses of FGF2. It is further disclosed that the pro-angiogenic effect of the hormone is initiated at the plasma membrane and is dependent upon activation by T4 of the MAPK signal transduction pathway. As provided above, methods for treatment of occlusive peripheral vascular disease and coronary diseases, in particular, the occlusion of coronary vessels, and disorders associated with the occlusion of the peripheral vasculature and/or coronary blood vessels are disclosed. Also disclosed are compositions and methods for promoting angiogenesis and/or recruiting collateral blood vessels in a patient in need thereof. The compositions include an effective amount of thyroid hormone analogs, polymeric forms, and derivatives. The methods involve the co-administration of an effective amount of thyroid hormone analogs, polymeric forms, and derivatives in low, daily dosages for a week or more with other standard pro-angiogenesis growth factors, vasodilators, anticoagulants, thrombolytics, or other vascular-related therapies.

The CAM assay has been used to validate angiogenic activity of a variety of growth factors and compounds believed to promote angiogenesis. For example, T4 in physiological concentrations was shown to be pro-angiogenic in this in vitro model and on a molar basis to have the activity of FGF2. The presence of 6-N-propyl-2-thiouracil (PTU) did not reduce the effect of T4, indicating that de-iodination of T4 to generate T3 was not a prerequisite in this model. A summary of the pro-angiogenesis effects of various thyroid hormone analogs is listed in Table 1.

TABLE 1

Pro-angiogenesis Effects of Various Thyroid Hormone Analogs in the CAM Model

| TREATMENT | ANGIOGENESIS INDEX |
|---|---|
| PBS (Control) | 89.4 ± 9.3 |
| DITPA (0.01 uM) | 133.0 ± 11.6 |
| DITPA (0.1 uM) | 167.3 ± 12.7 |
| DITPA (0.2 mM) | 117.9 ± 5.6 |
| GC-1 (0.01 uM) | 169.6 ± 11.6 |
| GC-1 (0.1 uM) | 152.7 ± 9.0 |
| T4 agarose (0.1 uM) | 195.5 + 8.5 |
| T4 (0.1 uM) | 143.8 ± 7.9 |
| FGF2 (1 ug) | 155 ± 9 | n = 8 per group

The appearance of new blood vessel growth in this model requires several days, indicating that the effect of thyroid hormone was wholly dependent upon the interaction of the nuclear receptor for thyroid hormone (TR) with the hormone. Actions of iodothyronines that require intranuclear complexing of TR with its natural ligand, T3, are by definition, genomic, and culminate in gene expression. On the other hand, the preferential response of this model system to T4 rather than T3, the natural ligand of TR-raised the possibility that angiogenesis might be initiated nongenomically at the plasma membrane by T4 and culminate in effects that require gene transcription. Non-genomic actions of T4 have been widely described, are usually initiated at the plasma membrane and may be mediated by signal transduction pathways. They do not require intranuclear ligand of iodothyronine and TR, but may interface with or modulate gene transcription. Non-genomic actions of steroids have also been well described and are known to interface with genomic actions of steroids or of other compounds. Experiments carried out with T4 and tetrac or with agarose-T4 indicated that the pro-angiogenic effect of T4 indeed very likely was initiated at the plasma membrane. Tetrac blocks membrane-initiated effects of T4, but does not, itself activate signal transduction. Thus, it is a probe for non-genomic actions of thyroid hormone. Agarose-T4 has a molecular weight of 120,000 daltons and does not to gain entry to the cell interior and has been used to examine models for cell surface-initiated actions of the hormone. The thyroid hormone may be covalently bonded via the amino nitrogen on the alanine side chain of the agarose.

In part, this invention provides compositions and methods for promoting angiogenesis in a subject in need thereof. Conditions amenable to treatment by promoting angiogenesis include, for example, occlusive peripheral vascular disease and coronary diseases, in particular, the occlusion of coronary vessels, and disorders associated with the occlusion of the peripheral vasculature and/or coronary blood vessels, erectile dysfunction, stroke, and wounds. Also disclosed are compositions and methods for promoting angiogenesis and/or recruiting collateral blood vessels in a patient in need thereof. The compositions include an effective amount of polymeric forms of thyroid hormone analogs and derivatives and an effective amount of an adenosine and/or nitric oxide donor. The compositions can be in the form of a sterile, injectable, pharmaceutical formulation that includes an angiogenically effective amount of thyroid hormone-like substance and adenosine derivatives in a physiologically and pharmaceutically acceptable carrier, optionally with one or more excipients.

Myocardial Infarction

A major reason for heart failure following acute myocardial infarction is an inadequate response of new blood vessel formation, i.e., angiogenesis. Thyroid hormone and its analogs are beneficial in heart failure and stimulate coronary angiogenesis. The methods of the invention include, in part, delivering a single treatment of a thyroid hormone analog at the time of infarction either by direct injection into the myocardium, or by simulation of coronary injection by intermittent aortic ligation to produce transient isovolumic contractions to achieve angiogenesis and/or ventricular remodeling.

Accordingly, in one aspect the invention features methods for treating occlusive vascular disease, coronary disease, myocardial infarction, ischemia, stroke, and/or peripheral artery vascular disorders by promoting angiogenesis by administering to a subject in need thereof an amount of a polymeric form of thyroid hormone, or an analog thereof, effective for promoting angiogenesis.

Examples of polymeric forms of thyroid hormone analogs are also provided herein and can include triiodothyronine (T3), levothyroxine (T4), (GC-1), or 3,5-diiodothyropropionic acid (DITPA) conjugated to polyvinyl alcohol, acrylic acid ethylene co-polymer, polylactic acid, or agarose.

The methods also involve the co-administration of an effective amount of thyroid hormone-like substance and an effective amount of an adenosine and/or NO donor in low, daily dosages for a week or more. One or both components can be delivered locally via catheter. Thyroid hormone analogs and derivatives in vivo can be delivered to capillary beds surrounding ischemic tissue by incorporation of the compounds into an appropriately sized liposome, microparticle or nanoparticle. Thyroid hormone analogs, polymeric forms and derivatives can be targeted to ischemic tissue by covalent linkage with a suitable antibody.

The method may be used as a treatment to restore cardiac function after a myocardial infarction. The method may also be used to improve blood flow in patients with coronary artery disease suffering from myocardial ischemia or inadequate blood flow to areas other than the heart including, for example, occlusive peripheral vascular disease (also known as peripheral arterial occlusive disease), or erectile dysfunction.

Wound Healing

Wound angiogenesis is an important part of the proliferative phase of healing. Healing of any skin wound other than the most superficial cannot occur without angiogenesis. Not only does any damaged vasculature need to be repaired, but the increased local cell activity necessary for healing requires an increased supply of nutrients from the bloodstream. Moreover, the endothelial cells which form the lining of the blood vessels are important in themselves as organizers and regulators of healing.

Thus, angiogenesis provides a new microcirculation to support the healing wound. The new blood vessels become clinically visible within the wound space by four days after injury. Vascular endothelial cells, fibroblasts, and smooth muscle cells all proliferate in coordination to support wound granulation. Simultaneously, re-epithelialization occurs to reestablish the epithelial cover. Epithelial cells from the wound margin or from deep hair follicles migrate across the wound and establish themselves over the granulation tissue and provisional matrix. Growth factors such as keratinocyte growth factor (KGF) mediate this process. Several models (sliding versus rolling cells) of epithelialization exist.

As thyroid hormones regulate metabolic rate, when the metabolism slows down due to hypothyroidism, wound healing also slows down. The role of topically applied thyroid hormone analogs or polymeric forms in wound healing therefore represents a novel strategy to accelerate wound healing in diabetics and in non-diabetics with impaired wound healing abilities. Topical administration can be in the form of attachment to a Band-Aid. Additionally, nano-polymers and nano-particles prevent the thyroid hormone and analogs thereof from entering the intracellular portions of the cell thus reducing the side effects exhibited through genomic actions on gene expression.

Accordingly, another embodiment of the invention features methods for treating wounds by promoting angiogenesis by administering to a subject in need thereof an amount of a polymeric form of thyroid hormone, or an analog thereof, effective for promoting angiogenesis. For details, see Example 9.

The Role of Thyroid Hormone, Analogs, and Polymeric Conjugations in Inhibiting Angiogenesis The invention also provides, in another part, compositions and methods for inhibiting angiogenesis in a subject in need thereof. Conditions amenable to treatment by inhibiting angiogenesis include, for example, primary or metastatic tumors and diabetic retinopathy. The compositions can include an effective amount of tetrac, triac, or mAb LM609. The compositions can be in the form of a sterile, injectable, pharmaceutical formulation that includes an anti-angiogenically effective amount of an anti-angiogenic substance in a physiologically and pharmaceutically acceptable carrier, optionally with one or more excipients. In a further aspect, the invention provides methods for treating a condition amenable to treatment by inhibiting angiogenesis by administering to a subject in need thereof an amount of an anti-angiogenesis agent effective for inhibiting angiogenesis.

Examples of the anti-angiogenesis agents used for inhibiting angiogenesis are also provided by the invention and include, but are not limited to, tetraiodothyroacetic acid (tetrac), triiodothyroacetic acid (triac), monoclonal antibody LM609, or combinations thereof. Such anti-angiogenesis agents can act at the cell surface to inhibit the pro-angiogenesis agents.

Cancer-Related New Blood Vessel Growth

Examples of the conditions amenable to treatment by inhibiting angiogenesis include, but are not limited to, primary or metastatic tumors. In such a method, compounds which inhibit the thyroid hormone-induced angiogenic effect are used to inhibit angiogenesis. Details of such a method are illustrated in Examples 12, 14, 16, 17, 20, and 21.

Diabetic Retinopathy

Examples of the conditions amenable to treatment by inhibiting angiogenesis include, but are not limited to diabetic retinopathy, and related conditions. In such a method, compounds which inhibit the thyroid hormone-induced angiogenic effect are used to inhibit angiogenesis. Details of such a method and experimental data confirming treatment of diabetic retinopathy are illustrated in Examples 8A, 8B and 13. While the provided examples are illustrated using tetrac, nanoparticulate tetrac or polymers thereof conjugated via a covalent bond, triac and mAb LM609 and nanoparticle formulations and polymer formulations thereof may be substituted in place of tetrac and achieve similar results.

Retinopathy of Prematurity (ROP) is a blindness-causing neovascularizing disease affecting premature infants treated with high concentrations of oxygen. ROP develops in two distinct stages: 1) the hyperoxic insult leads to obliteration of immature retinal vessels and 2) initiated upon resumption of the breathing of normal air, is an adverse compensatory neovascularization response. The formation of new vessels is excessive, neovessels may be leaky, and the inner limiting membrane of the retina may be breached, allowing vessel growth into the vitreous which might ultimately lead to retinal detachment and vision loss. The formation of new vessels is mediated by ischemia-induced vascular endothelial growth factor (VEGF). VEGF is a potent and specific endothelial cell cytokine that can be up-regulated by hypoxia. Evidences show that VEGF is a significant mediator in retinal neovascular diseases and other disorders in which hypoxia is believed to influence the pathogenesis. Tetrac is a potent inhibitor of VEGF or other growth factor-induced angiogenesis.

It is known that proliferative retinopathy induced by hypoxia (rather than diabetes) depends upon alphaV ($\alpha$V) integrin expression. Thyroid hormone action on a specific integrin alpha-V-beta-3 ($\alpha$V$\beta$3) is permissive in the development of diabetic retinopathy. Integrin $\alpha$V$\beta$3 contains the cell surface receptor for thyroid hormone and thyroid hormone analogues. Thyroid hormone, its analogues, and polymer conjugations, act via this receptor to induce angiogenesis.

Methods of Treatment

Thyroid hormone analogs, polymeric forms, and derivatives can be used in a method for promoting angiogenesis in a patient in need thereof. The method involves the co-administration of an effective amount of thyroid hormone analogs, polymeric forms, and derivatives in low, daily dosages for a week or more. The method may be used as a treatment to restore cardiac function after a myocardial infarction. The method may also be used to improve blood flow in patients with coronary artery disease suffering from myocardial ischemia or inadequate blood flow to areas other than the heart, for example, peripheral vascular disease, for example, peripheral arterial occlusive disease, where decreased blood flow is a problem.

The compounds can be administered via any medically acceptable means which is suitable for the compound to be administered, including oral, rectal, topical, intraocular, intranasal, intratumoral or parenteral (including subcutaneous, intramuscular and intravenous) administration. For example, adenosine has a very short half-life. For this reason, it is preferably administered intravenously. However, adenosine agonists have been developed which have much longer half-lives, and which can be administered through other means. Thyroid hormone analogs, polymeric forms, and derivatives can be administered, for example, intravenously, orally, topically, intraocularly, intratumorally or intranasally.

In some embodiments, the thyroid hormone analogs, polymeric forms, and derivatives are administered via different means.

The amounts of the thyroid hormone, its analogs, polymeric forms, and derivatives required to be effective in stimulating angiogenesis will, of course, vary with the individual being treated and is ultimately at the discretion of the physician. The factors to be considered include the condition of the patient being treated, the efficacy of the particular adenosine $A_2$ receptor agonist being used, the nature of the formulation, and the patient's body weight. Occlusion-treating dosages of thyroid hormone analogs or its polymeric forms, and derivatives are any dosages that provide the desired effect.

Formulations

The compounds described above are preferably administered in a formulation including thyroid hormone analogs or its polymeric forms, and derivatives together with an acceptable carrier for the mode of administration. Any formulation or drug delivery system containing the active ingredients, which is suitable for the intended use, as are generally known to those of skill in the art, can be used. Suitable pharmaceutically acceptable carriers for oral, rectal, topical, parenteral (including subcutaneous, intraperitoneal, intramuscular and intravenous), or intratumoral (direct injection to the tumor site) administration are known to those of skill in the art. The carrier must be pharmaceutically acceptable in the sense of being compatible with the other ingredients of the formulation and not deleterious to the recipient thereof.

Formulations suitable for parenteral administration and intratumoral administration conveniently include sterile aqueous preparation of the active compound, which is preferably isotonic with the blood of the recipient. Thus, such formulations may conveniently contain distilled water, 5% dextrose in distilled water or saline. Useful formulations also include concentrated solutions or solids containing the compound which upon dilution with an appropriate solvent give a solution suitable for parental administration above.

For enteral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion, or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active, or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

In one embodiment, the thyroid hormone analogs or its polymeric forms, and adenosine derivatives can be formulated into a liposome, microparticle or nanoparticle, which is suitably sized to lodge in capillary beds following intravenous administration. When the liposome, microparticle or nanoparticle is lodged in the capillary beds surrounding ischemic tissue, the agents can be administered locally to the site at which they can be most effective. Suitable liposomes for targeting ischemic tissue are generally less than about 200 nanometers and are also typically unilamellar vesicles, as disclosed, for example, in U.S. Pat. No. 5,593,688 to Baldeschweiler, entitled "Liposomal targeting of ischemic tissue," the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

In one embodiment, the formulations are administered via catheter directly to the inside of blood vessels. The administration can occur, for example, through holes in the catheter. In those embodiments wherein the active compounds have a relatively long half-life (on the order of 1 day to a week or more), the formulations can be included in biodegradable polymeric hydrogels, such as those disclosed in U.S. Pat. No. 5,410,016 to Hubbell et al. These polymeric hydrogels can be delivered directly to the inside of the tissue lumen.

The formulations may conveniently be presented in unit dosage form and may be prepared by any of the methods well known in the art of pharmacy. All methods include the step of bringing the active compound into association with a carrier, which constitutes one or more accessory ingredients. In general, the formulations are prepared by uniformly and intimately bringing the active compound into association with a liquid carrier or a finely divided solid carrier and then, if necessary, shaping the product into desired unit dosage form.

The formulations can optionally include additional components, such as various biologically active substances such as growth factors (including TGF-beta., basic fibroblast growth factor (FGF2), epithelial growth factor (EGF), transforming growth factors alpha and beta (TGF alpha. and beta.), nerve growth factor (NGF), platelet-derived growth factor (PDGF), and vascular endothelial growth factor/vascular permeability factor (VEGF/VPF)), antiviral, antibacterial, antiinflammatory, immuno-suppressant, analgesic, vascularizing agent, and cell adhesion molecule.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants), and the like.

Materials & Methods

Reagents:

All reagents were chemical grade and purchased from Sigma Chemical Co. (St. Louis, Mo.) or through VWR Scientific (Bridgeport, N.J.). Cortisone acetate, bovine serum albumin (BSA) and gelatin solution (2% type B from bovine skin) were purchased from Sigma Chemical Co. Fertilized chicken eggs were purchased from Charles River Laboratories, SPAFAS Avian Products & Services (North Franklin, Conn.). T4, 3,5,3'-triiodo-L-thyronine (T3), tetraiodothyroacetic acid (tetrac), T4-agarose, and 6-N-propyl-2-thiouracil (PTU) were obtained from Sigma; PD 98059 from Calbiochem; and CGP41251 was a gift from Novartis Pharma (Basel, Switzerland). Polyclonal anti-FGF2 and monoclonal anti-β-actin were obtained from Santa Cruz Biotechnology and human recombinant FGF2 from Invitrogen. Polyclonal antibody to phosphorylated ERK1/2 was from New England Biolabs and goat anti-rabbit IgG from DAKO.

Chorioallantoic Membrane (CAM) Model of Angiogenesis:

In vivo Neovascularization was examined by methods described previously. 9-12 Ten-day-old chick embryos were purchased from SPAFAS (Preston, Conn.) and incubated at 37° C. with 55% relative humidity. A hypodermic needle was used to make a small hole in the shell concealing the air sac, and a second hole was made on the broad side of the egg, directly over an avascular portion of the embryonic membrane that was identified by candling. A false air sac was created beneath the second hole by the application of negative pressure at the first hole, causing the CAM to separate from the shell. A window approximately 1.0 $cm^2$ was cut in the shell over the dropped CAM with a small-crafts grinding wheel (Dremel, division of Emerson Electric Co.), allowing direct access to the underlying CAM. FGF2 (1 µg/mL) was used as a standard proangiogenic agent to induce new blood vessel branches on the CAM of 10-day-old embryos. Sterile disks of No. 1 filter paper (Whatman International) were pretreated with 3 mg/mL cortisone acetate and 1 mmol/L PTU and air dried under sterile conditions. Thyroid hormone, hormone analogues, FGF2 or control solvents, and inhibitors were then applied to the disks and the disks allowed to dry. The disks were then suspended in PBS and placed on growing CAMs. Filters treated with T4 or FGF2 were placed on the first day of the 3-day incubation, with antibody to FGF2 added 30 minutes later to selected samples as indicated. At 24 hours, the MAPK cascade inhibitor PD 98059 was also added to CAMs topically by means of the filter disks.

Microscopic Analysis of CAM Sections:

After incubation at 37° C. with 55% relative humidity for 3 days, the CAM tissue directly beneath FGF2 and TF/VIIa filter disk was resected from control and treated CAM samples. Tissues were washed 3× with PBS, placed in 35-mm Petri dishes (Nalge Nunc), and examined under an SV6 stereomicroscope (Zeiss) at X50 magnification. Digital images of CAM sections exposed to filters were collected using a 3-charge—coupled device color video camera system (Toshiba) and analyzed with Image-Pro software (Media Cybernetics). The number of vessel branch points contained in a circular region equal to the area of each filter disk were counted. One image was counted in each CAM preparation, and findings from 8 to 10 CAM preparations were analyzed for each treatment condition (thyroid hormone or analogues, FGF2, FGF2 antibody, PD 98059). In addition, each experiment was performed 3 times. The resulting angiogenesis index is the mean±SEM of new branch points in each set of samples.

Results:

Effects of topically applied formulations of tetrac and tetrac-nanoparticles on Fibroblast Growth Factor (FGF2) inhibited angiogenesis in the CAM model. Tetrac or tetrac immobilized on PLGA nanoparticles were administered to chick embryos topically, onto growth factor (FGF)-impregnated filter disk placed over the branch point of a selected vessel. After 3 days, CAM tissues directly beneath the growth factor filter disk were removed, examined microscopically, and the images analyzed with the Image-Pro Plus software. The number of branch points in a circular region equal to the area of a filter was counted. Nanoparticulate tetrac and tetrac significantly inhibited branch point formation-induced by FGF2

FGF2 Assays:

ECV304 endothelial cells were cultured in M199 medium supplemented with 10% fetal bovine serum. ECV304 cells ($10^6$ cells) were plated on 0.2% gel-coated 24-well plates in complete medium overnight, and the cells were then washed with serum-free medium and treated with T4 or T3 as indicated. After 72 hours, the supernatants were harvested and assays for FGF performed without dilution using a commercial ELISA system (R&D Systems).

MAPK Activation:

ECV304 endothelial cells were cultured in M199 medium with 0.25% hormone-depleted serum 13 for 2 days. Cells were then treated with T4 ($10^{-7}$ mol/L) for 15 minutes to 6 hours. In additional experiments, cells were treated with T4 or FGF2 or with T4 in the presence of PD 98059 or CGP41251. Nuclear fractions were prepared from all samples by our method reported previously, the proteins separated by polyacrylamide gel electrophoresis, and transferred to membranes for immunoblotting with antibody to phosphorylated ERK 1/2. The appearance of nuclear phosphorylated ERK1/2 signifies activation of these MAPK isoforms by T4.

Reverse Transcription—Polymerase Chain Reaction:

Confluent ECV304 cells in 10-cm plates were treated with T4 ($10^{-7}$ mol/L) for 6 to 48 hours and total RNA extracted using guanidinium isothiocyanate (Biotecx Laboratories). RNA (1 µg) was subjected to reverse transcription-polymerase chain reaction (RT-PCR) using the Access RT-PCR system (Promega). Total RNA was reverse transcribed into cDNA at 48° C. for 45 minutes, then denatured at 94° C. for 2 minutes. Second-strand synthesis and PCR amplification were performed for 40 cycles with denaturation at 94° C. for 30 s, annealing at 60° C. for 60 s, and extension at 68° C. for 120 s, with final ex-tension for 7 minutes at 68° C. after completion of all cycles. PCR primers for FGF2 were as follows: FGF2 sense strand 5'-TGGTATGTGGCACT-GAAACG-3' (SEQ ID NO:1), antisense strand 5' CTCAAT-GACCTGGCGAAGAC-3' (SEQ ID NO:2); the length of the PCR product was 734 bp. Primers for GAPDH included the sense strand 5'-AAGGTCATCCCTGAGCTGAACG-3' (SEQ ID NO:3), and antisense strand 5'-GGGTGTCGCTGT-TGAAGTCAGA-3' (SEQ ID NO:4); the length of the PCR product was 218 bp. The products of RT-PCR were separated by electrophoresis on 1.5% agarose gels and visualized with ethidium bromide. The target bands of the gel were quantified using LabImage software (Kapelan), and the value for [FGF2/GAPDH]X10 calculated for each time point.

Statistical Analysis:

Statistical analysis was performed by 1-way ANOVA comparing experimental with control samples.

In Vivo Angiogenesis in Matrigel $FGF_2$ or Cancer Cell Lines Implant in Mice: In Vivo Murine Angiogenesis Model:

The murine matrigel model will be conducted according to previously described methods (Grant et al., 1991; Okada et al., 1995) and as implemented in our laboratory (Powel et al., 2000). Briefly, growth factor free matrigel (Becton Dickinson, Bedford Mass.) will be thawed overnight at 4° C. and placed on ice. Aliquots of matrigel will be placed into cold polypropylene tubes and FGF2, thyroid hormone analogs or cancer cells ($1\times10^6$ cells) will be added to the matrigel. Matrigel with saline, FGF2, thyroid hormone analogs or cancer cells will be subcutaneously injected into the ventral midline of the mice. At day 14, the mice will be sacrificed and the solidified gels will be resected and analyzed for presence of new vessels. T4, T4-agarose, FgF2 Control in PBS and thyroid inhibitor tetrac and nanoparticulate tetrac dissolved in PBS will be injected subcutaneously at different doses. Control and experimental gel implants will be placed in a micro centrifuge tube containing 0.5 ml of cell lysis solution (Sigma, St. Louis, Mo.) and crushed with a pestle. Subsequently, the tubes will be allowed to incubate overnight at 4° C. and centrifuged at 1,500×g for 15 minutes on the following day. A 200 µl aliquot of cell lysate will be added to 1.3 ml of Drabkin's reagent solution (Sigma, St. Louis, Mo.) for each sample. The solution will be analyzed on a spectrophotometer at a 540 nm. The absorption of light is proportional to the amount of hemoglobin contained in the sample.

Tumor Growth and Metastasis—Chick Chorioallantoic Membrane (CAM) Model of Tumor Implant:

The protocol is as previously described (Kim et al., 2001). Briefly, $1\times10^7$ tumor cells will be placed on the surface of each CAM (7 day old embryo) and incubated for one week. The resulting primary and metastatic tumors will be excised and cut into 50 mg fragments. These fragments are placed on additional 10 CAMs per group and treated topically the following day with 25 µl of T4, T4-agarose, FGF2 Control in PBS and thyroid inhibitor tetrac and nanoparticulate tetrac dissolved in PBS. Seven days later, tumors will then be excised from the egg and tumor weights will be determined for each CAM. FIG. 8 is a diagrammatic sketch showing the steps involved in the in vivo tumor growth model in the CAM.

The effects of tetrac, triac, and thyroid hormone antagonists on tumor growth rate, tumor angiogenesis, and tumor metastasis of cancer cell lines can be determined.

Tumor Growth and Metastasis—Tumor Xenograft Model in Mice:

The model is as described in our publications by Kerr et al., 2000; Van Waes et al., 2000; Ali et al., 2001; and Ali et al., 2001, each of which is incorporated herein by reference in its entirety). The anti-cancer efficacy for tetrac, triac, and other thyroid hormone antagonists at different doses and against different primary and metastatic tumor types can be determined and compared.

Tumor Growth and Metastasis—Experimental Model of Metastasis:

The model is as described in our recent publications (Mousa, 2002; Amirkhosravi et al., 2003a and 2003b, each of which is incorporated by reference herein in its entirety). Briefly, B16 murine malignant melanoma cells (ATCC, Rockville, Md.) and other cancer lines will be cultured in RPMI 1640 (Invitrogen, Carlsbad, Calif.), supplemented with 10% fetal bovine serum, penicillin and streptomycin (Sigma, St. Louis, Mo.). Cells will be cultured to 70% confluency and harvested with trypsin-EDTA (Sigma) and washed twice with phosphate buffered saline (PBS). Cells were re-suspended in PBS at a concentration of either $2.0\times10^5$ cells/ml for experimental metastasis. Animals: C57/BL6 mice (Harlan, Indianapolis, Ind.) weighing 18-21 grams were used for this study. All procedures are in accordance with IACUC and institutional guidelines. The anti-cancer efficacy for tetrac, triac, and other thyroid hormone antagonists at different doses and against different tumor types can be determined and compared.

Effect of Thyroid Hormone Analogues on Angiogenesis.

T4 induced significant increase in angiogenesis index (fold increase above basal) in the CAM model. T3 at 0.001-1.0 µM or T4 at 0.1-1.0 µM achieved maximal effect in producing 2-2.5 fold increase in angiogenesis index as compared to 2-3 fold increase in angiogenesis index by 1 µg of FGF2 (Table 1 and FIGS. 1a and 1b). The effect of T4 in promoting angiogenesis (2-2.5 fold increase in angiogenesis index) was achieved in the presence or absence of PTU, which inhibit T4 to T3 conversion. T3 itself at 91-100 nM-induced potent pro-angiogenic effect in the CAM model. T4-agarose produced similar pro-angiogenesis effect to that achieved by T4. The pro-angiogenic effect of either T4 or T4-agarose was 100% blocked by tetrac or triac.

Enhancement of Pro-Angiogenic Activity of FGF2 by Sub-Maximal Concentrations of T4.

The combination of T4 and FGF2 at sub-maximal concentrations resulted in an additive increase in the angiogenesis index up to the same level like the maximal pro-angiogenesis effect of either FGF2 or T4 (FIG. 2).

Effects of MAPK Cascade Inhibitors on the Pro-Angiogenic Actions of T4 and FGF2 in the CAM model.

Figures 3A, 3B:
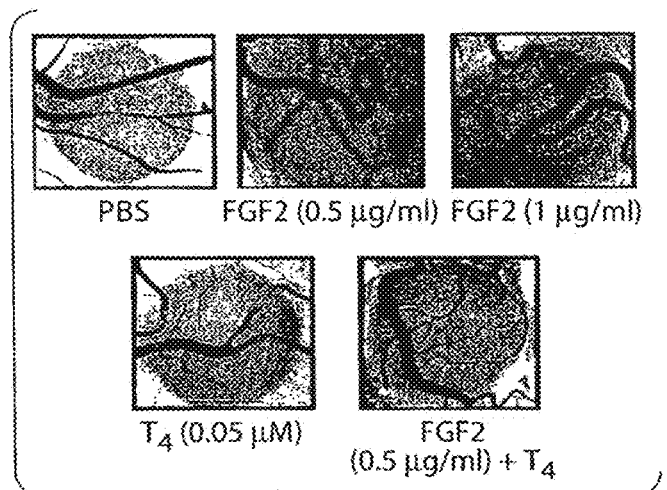
FIG. 3A: depicts that the tandem effects of T4 (0.05 µM) and FGF2 (0.5 µg/mL) in submaximal concentrations are additive in the CAM assay and equal the level of angiogenesis seen with FGF2 (1 µg/mL in the absence of T4).
FIG. 3B: depicts a summary of results from 3 experiments that examined actions of FGF2 and T4 in the CAM assay (means±SEM) as in A. *P<0.05; **P<0.001, comparing results of treated samples with those of PBS-treated control samples in 3 experiments.

The pro-angiogenesis effect of either T4 or FGF2 was totally blocked by PD 98059 at 0.8 (angiogenesis inhibitor)—8 μg (FIG. 3).

Effects of Specific Integrin αvβ3 Antagonists on the Pro-Angiogenic Actions of T4 and FGF2 in the CAM Model.

Figures 4A, 4B:
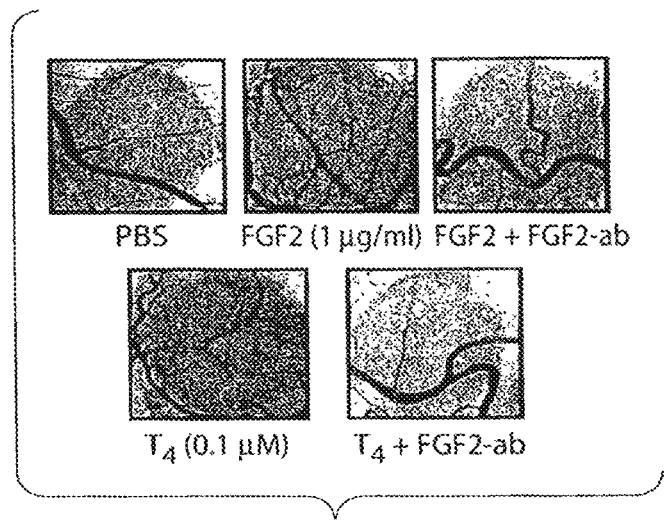
FIG. 4A: depicts the effects of anti-FGF2 on angiogenesis caused by T4 or exogenous FGF2, wherein FGF2 caused a 2-fold increase in angiogenesis in the CAM model in 3 experiments, an effect inhibited by antibody (ab) to FGF2 (8 µg). T4 also stimulated angiogenesis 1.5-fold, and this effect was also blocked by FGF2 antibody, indicating that the action of thyroid hormone in the CAM model is mediated by an autocrine/paracrine effect of FGF2 because T4 and T3 cause FGF2 release from cells in the CAM model (Table 1). We have shown previously that a nonspecific IgG antibody has no effect on angiogenesis in the CAM assay.
FIG. 4B: depicts the summary of results from 3 CAM experiments that studied the action of FGF2-ab in the presence of FGF2 or T4. *P<0.01; **P<0.001, indicating significant effects in 3 experiments studying the effects of thyroid hormone and FGF2 on angiogenesis and loss of these effects in the presence of antibody to FGF2.

The pro-angiogenesis effect of either T4 or FGF2 was totally blocked by the specific monoclonal antibody LM609 at 10 μg (FIGS. 4a and 4b).

The CAM assay has been used to validate angiogenic activity of a variety of growth factors and other promoters or inhibitors of angiogenesis. In the present studies, T4 in physiological concentrations was shown to be pro-angiogenic, with comparable activity to that of FGF2. The presence of PTU did not reduce the effect of T4, indicating that de-iodination of T4 to generate T3 was not a prerequisite in this model. Because the appearance of new blood vessel growth in this model requires several days, we assumed that the effect of thyroid hormone was totally dependent upon the interaction of the nuclear receptor for thyroid hormone (TR). Actions of iodothyronines that require intranuclear complexing of TR with its natural ligand, T3, are by definition, genomic, and culminate in gene expression. On the other hand, the preferential response of this model system to T4—rather than T3, the natural ligand of TR, raised the possibility that angiogenesis might be initiated non-genomically at the plasma membrane by T4 and culminate in effects that require gene transcription. Non-genomic actions of T4 have been widely described, are usually initiated at the plasma membrane and may be mediated by signal transduction pathways. They do not require intranuclear ligand binding of iodothyronine and TR, but may interface with or modulate gene transcription. Non-genomic actions of steroids have also been well-described and are known to interface with genomic actions of steroids or of other compounds. Experiments carried out with T4 and tetrac or with agarose-T4 indicated that the pro-angiogenic effect of T4 indeed very likely was initiated at the plasma membrane. We have shown elsewhere that tetrac blocks membrane-initiated effects of T4, but does not, itself, activate signal transduction. Thus, it is a probe for non-genomic actions of thyroid hormone. Agarose-T4 is thought not to gain entry to the cell interior and has been used by us and others to examine models for possible cell surface-initiated actions of the hormone.

These results suggest that another consequence of activation of MAPK by thyroid hormone is new blood vessel growth. The latter is initiated non-genomically, but of course requires a consequent complex gene transcription program.

The ambient concentrations of thyroid hormone are relatively stable. The CAM model, at the time we tested it, was thyroprival and thus may be regarded as a system, which does not reproduce the intact organism. We propose that circulating levels of T4 serve, with a variety of other regulators, to modulate the sensitivity of vessels to endogenous angiogenic factors, such as VEGF and FGF2.

The invention will be further illustrated in the following non-limiting examples.

EXAMPLES

Example 1

Effect of Thyroid Hormone on Angiogenesis

Figures 1A, 1B:
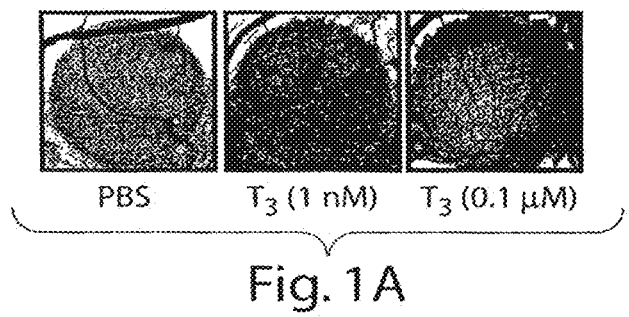
FIG. 1A: depicts the effects of T4 and T3 on angiogenesis quantitated in the chick Chorioallantoic Membrane (CAM) assay. Control samples were exposed to PBS and additional samples to 1 nM T3 or 0.1 µM T4 for 3 days. Both hormones caused increased blood vessel branching in these representative images from 3 experiments.
FIG. 1B: depicts the tabulation of mean±SEM of new branches formed from existing blood vessels during the experimental period drawn from 3 experiments, each of which included 9 CAM assays. At the concentrations shown, T3 and T4 caused similar effects (1.9-fold and 2.5-fold increases, respectively, in branch formation). **P<0.001 by 1-way ANOVA, comparing hormone-treated with PBS-treated CAM samples.

As seen in FIG. 1A and summarized in FIG. 1B, both L-T4 and L-T3 enhanced angiogenesis in the CAM assay. T4, at a physiologic total concentration in the medium of 0.1 μM, increased blood vessel branch formation by 2.5-fold ($P<0.001$). T3 (1 nM) also stimulated angiogenesis 2-fold. The possibility that T4 was only effective because of conversion of T4 to T3 by cellular 5'-monodeiodinase was ruled out by the finding that the deiodinase inhibitor PTU had no inhibitory effect on angiogenesis produced by T4. PTU was applied to all filter disks used in the CAM model. Thus, T4 and T3 promote new blood vessel branch formation in a CAM model that has been standardized previously for the assay of growth factors.

Example 2

Effects of T4—Agarose and Tetrac

We have shown previously that T4-agarose stimulates cellular signal transduction pathways initiated at the plasma membrane in the same manner as T4 and that the actions of T4 and T4-agarose are blocked by a deaminated iodothyronine analogue, tetrac, which is known to inhibit binding of T4 to plasma membranes. In the CAM model, the addition of tetrac (0.1 μM) inhibited the action of T4 (FIG. 2A), but tetrac alone had no effect on angiogenesis (FIG. 2C). The action of T4-agarose, added at a hormone concentration of 0.1 μM, was comparable to that of T4 in the CAM model (FIG. 2B), and the effect of T4-agarose was also inhibited by the action of tetrac (FIG. 2B; summarized in 2C).

Example 3

Enhancement of Proangiogenic Activity of FGF2 by a Submaximal Concentration of T4

Angiogenesis is a complex process that usually requires the participation of polypeptide growth factors. The CAM assay requires at least 48 hours for vessel growth to be manifest; thus, the apparent plasma membrane effects of thyroid hormone in this model are likely to result in a complex transcriptional response to the hormone. Therefore, we determined whether FGF2 was involved in the hormone response and whether the hormone might potentiate the effect of subphysiologic levels of this growth factor. T4 (0.05 μM) and FGF2 (0.5 μg/mL) individually stimulated angiogenesis to a modest degree (FIG. 3). The angiogenic effect of this submaximal concentration of FGF2 was enhanced by a subphysiologic concentration of T4 to the level caused by 1.0 μg FGF2 alone. Thus, the effects of submaximal hormone and growth factor concentrations appear to be additive. To define more precisely the role of FGF2 in thyroid hormone stimulation of angiogenesis, a polyclonal antibody to FGF2 was added to the filters treated with either FGF2 or T4, and angiogenesis was measured after 72 hours. FIG. 4 demonstrates that the FGF2 antibody inhibited angiogenesis stimulated either by FGF2 or by T4 in the absence of exogenous FGF2, suggesting that the T4 effect in the CAM assay was mediated by increased FGF2 expression. Control IgG antibody has no stimulatory or inhibitory effect in the CAM assay.

Example 4

Stimulation of FGF2 Release from Endothelial Cells by Thyroid Hormone

Levels of FGF2 were measured in the media of ECV304 endothelial cells treated with either T4 (0.1 μM) or T3 (0.01 μM) for 3 days. As seen in the Table 2, T3 stimulated FGF2 concentration in the medium 3.6-fold, whereas T4 caused a 1.4-fold increase. This finding indicates that thyroid hormone may enhance the angiogenic effect of FGF2, at least in part, by increasing the concentration of growth factor available to endothelial cells.

TABLE 2

Effect of T4 and T3 on Release of
FGF2 From ECV304 Endothelial Cells

| Cell Treatment | FGF2 (pg/mL/$10^6$ cells) |
|---|---|
| Control | 27.7 ± 3.1 |
| T3 (0.01 µM) | 98.8 ± 0.5* |
| T3 + PD 98059 (2 µM) | 28.4 ± 3.2 |
| T3 + PD 98059 (20 µM) | 21.7 ± 3.5 |
| T4 (0.1 µM) | 39.2 ± 2.8† |
| T4 + PD 98059 (2 µM) | 26.5 ± 4.5 |
| T4 + PD 98059 (20 µM) | 23.2 ± 4.8 |

*$P < 0.001$, comparing T3-treated samples with control samples by ANOVA;
†$P < 0.05$, comparing T4-treated samples with control samples by ANOVA.

Example 5

Role of the ERK1/2 Signal Transduction Pathway in Stimulation of Angiogenesis by Thyroid Hormone and FGF2

A pathway by which T4 exerts a non-genomic effect on cells is the MAPK signal transduction cascade, specifically that of ERK1/2 activation. We know that T4 enhances ERK1/2 activation by epidermal growth factor. The role of the MAPK pathway in stimulation by thyroid hormone of FGF2 expression was examined by the use of PD 98059 (2 to 20 µM), an inhibitor of ERK1/2 activation by the tyrosine-threonine kinases MAPK kinase-1 (MEK1) and MEK2. The data in the Table demonstrate that PD 98059 effectively blocked the increase in FGF2 release from ECV304 endothelial cells treated with either T4 or T3. Parallel studies of ERK1/2 inhibition were performed in CAM assays, and representative results are shown in FIG. 5. A combination of T3 and T4, each in physiologic concentrations, caused a 2.4-fold increase in blood vessel branching, an effect that was completely blocked by 3 µM PD 98059 (FIG. 5A). FGF2 stimulation of branch formation (2.2-fold) was also effectively blocked by this inhibitor of ERK1/2 activation (FIG. 5B). Thus, the proangiogenic effect of thyroid hormone begins at the plasma membrane and involves activation of the ERK1/2 pathway to promote FGF2 release from endothelial cells. ERK1/2 activation is again required to transduce the FGF2 signal and cause new blood vessel formation.

Example 6

Action of Thyroid Hormone and FGF2 on MAPK Activation

Stimulation of phosphorylation and nuclear translocation of ERK1/2 MAPKs was studied in ECV304 cells treated with T4 ($10^{-7}$ mol/L) for 15 minutes to 6 hours. The appearance of phosphorylated ERK1/2 in cell nuclei occurred within 15 minutes of T4 treatment, reached a maximal level at 30 minutes, and was still apparent at 6 hours (FIG. 6A). This effect of the hormone was inhibited by PD 98059 (FIG. 6B), a result to be expected because this compound blocks the phosphorylation of ERK1/2 by MAPK kinase. The traditional protein kinase C (PKC)-α, PKC-β, and PKC-γ inhibitor CGP41251 also blocked the effect of the hormone on MAPK activation in these cells, as we have seen with T4 in other cell lines. Thyroid hormone enhances the action of several cytokines and growth factors, such as interferon-γ13 and epidermal growth factor. In ECV304 cells, T4 enhanced the MAPK activation caused by FGF2 in a 15-minute co incubation (FIG. 6C). Applying observations made in ECV304 cells to the CAM model, we propose that the complex mechanism by which the hormone induces angiogenesis includes endothelial cell release of FGF2 and enhancement of the autocrine effect of released FGF2 on angiogenesis.

Example 7

RT-PCR in ECV304 Cells Treated with Thyroid Hormone

The final question addressed in studies of the mechanism of the proangiogenic action of T4 was whether the hormone may induce FGF2 gene expression. Endothelial cells were treated with T4 ($10^{-7}$ mol/L) for 6 to 48 hours, and RT-PCR-based estimates of FGF2 and GAPDH RNA (inferred from cDNA measurements; FIG. 7) were performed. Increase in abundance of FGF2 cDNA, corrected for GAPDH content, was apparent by 6 hours of hormone treatment and was further enhanced by 48 hours.

Example 8A

Retinal Neovascularization Model in Mice (Diabetic and Non-Diabetic)

To assess the pharmacologic activity of a test article on retinal neovascularization, infant mice are exposed to a high oxygen environment for 7 days and allowed to recover, thereby stimulating the formation of new vessels on the retina. Test articles are evaluated to determine if retinal neovascularization is suppressed. The retinas are examined with hematoxylin-eosin staining and with at least one stain, which demonstrates neovascularization (usually a Selectin stain). Other stains (such as PCNA, PAS, GFAP, markers of angiogenesis, etc.) can be used. A summary of the model is below:

Animal Model

Infant mice (P7) and their dams are placed in a hyper-oxygenated environment (70-80%) for 7 days.
On P12, the mice are removed from the oxygenated environment and placed into a normal environment
Mice are allowed to recover for 5-7 days.
Mice are then sacrificed and the eyes collected.
Eyes are either frozen or fixed as appropriate
The eyes are stained with appropriate histochemical stains
The eyes are stained with appropriate immunohistochemical stains
Blood, serum, or other tissues can be collected
Eyes, with special reference to microvascular alterations, are examined for any and all findings. Neovascular growth will be semi quantitatively scored. Image analysis is also available.

Example 8B

Thyroid Hormone and Diabetic Retinopathy

A protocol disclosed in J de la Cruz et al., J Pharmacol Exp Ther 280:454-459, 1997, is used for the administration of tetrac, tetrac nanoparticles and polymers conjugated via a covalent bond using an ester linkage to rats that have streptozotocin (STZ)-induced experimental diabetes and diabetic retinopathy. The results of this experiment demonstrated the inhibition by tetrac of the appearance of proliferative retinopathy (angiogenesis) and reduction in neovascularization, producing similar results similar to example 13 described below including 50% inhibition of neovascularization. Tetrac inhibition of retinal neovascularization in the oxygen-induced retinopathy model, makes tetrac a viable therapeutic strategy for proliferative diabetic retinopathy.

Example 9

In Vitro Human Epithelial and Fibroblast Wound Healing

The in vitro 2-dimensional wound healing method is as described in Mohamed S, Nadijcka D, Hanson, V. Wound healing properties of cimetidine in vitro. Drug Intell Clin Pharm 20: 973-975; 1986, incorporated herein by reference in its entirety. Additionally, a 3-dimensional wound healing method already established in our Laboratory will be utilized in this study (see below). Data show potent stimulation of wound healing by thyroid hormone.

In Vitro 3D Wound Healing Assay of Human Dermal Fibroblast Cells:
Step 1: Prepare Contracted Collagen Gels:
  1) Coat 24-well plate with 350 ul 2% BSA at RT for 2 hr,
  2) 80% confluent NHDF (normal human dermal fibroblast cells, Passage 5-9) are trypsinized and neutralized with growth medium, centrifuge and wash once with PBS
  3) Prepare collagen-cell mixture, mix gently and always on ice:

| Stock solution | Final Concentration |
| --- | --- |
| 5xDMEC | 1xDMEM |
| 3 mg/ml vitrogen | 2 mg/ml |
| ddH2O | optimal |
| NHDF | 2 x 10~5 cells/ml |
| FBS | 1% |

4) Aspire 2% BSA from 24 well plate, add collagen-cell mixture 350 µl/well, and incubate the plate in 37° C. CO2 incubator.
  5) After 1 hr, add DMEM+5% FBS medium 0.5 ml/well, use a 10 ul tip Detach the collagen gel from the edge of each well, then incubate for 2 days. The fibroblast cells will contract the collagen gel Step 2: Prepare 3D Fibrin Wound Clot and Embed Wounded Collagen Culture
  1) Prepare fibrinogen solution (1 mg/ml) with or without testing regents. 350 ul fibrinogen solution for each well in eppendorf tube.

| Stock solution | Final Concentration |
| --- | --- |
| 5xDMEC | 1xDMEM |
| Fibrinogen | 1 mg/ml |
| ddH2O | optimal |
| testing regents | optimal concentration |
| FBS | 1% or 5% |

2) Cut each contracted collagen gel from middle with scissors. Wash the gel with PBS and transfer the gel to the center of each well of 24 well plate
  3) Add 1.5 µl of human thrombin (0.25 U/µl) to each tube, mix well and then add the solution around the collagen gel, the solution will polymerize in 10 mins.

After 20 mins, add DMEM+1% (or 5%) FBS with or without testing agent, 450 µl/well and incubate the plate in 37° C. CO2 incubator for up to 5 days. Take pictures on each day.

In Vivo Wound Healing in Diabetic Rats:
Using an acute incision wound model in diabetic rats, the effects of thyroid hormone analogs and its conjugated forms are tested. The rate of wound closure, breaking strength analyses and histology are performed periodically on days 3-21.

Example 10

Rodent Model of Myocardial Infarction

The coronary artery ligation model of myocardial infarction is used to investigate cardiac function in rats. The rat is initially anesthetized with xylazine and ketamine, and after appropriate anesthesia is obtained, the trachea is intubated and positive pressure ventilation is initiated. The animal is placed supine with its extremities loosely taped and a median sternotomy is performed. The heart is gently exteriorized and a 6-O suture is firmly tied around the left anterior descending coronary artery. The heart is rapidly replaced in the chest and the thoracotomy incision is closed with a 3-O purse string suture followed by skin closure with interrupted sutures or surgical clips. Animals are placed on a temperature regulated heating pad and closely observed during recovery. Supplemental oxygen and cardiopulmonary resuscitation are administered if necessary. After recovery, the rat is returned to the animal care facility. Such coronary artery ligation in the rat produces large anterior wall myocardial infarctions. The 48 hr. mortality for this procedure can be as high as 50%, and there is variability in the size of the infarct produced by this procedure. Based on these considerations, and prior experience, to obtain 16-20 rats with large infarcts so that the two models of thyroid hormone delivery discussed below can be compared, approximately 400 rats are required.

These experiments are designed to show that systemic administration of thyroid hormone either before or after coronary artery ligation leads to beneficial effects in intact animals, including the extent of hemodynamic abnormalities assessed by echocardiography and hemodynamic measurements, and reduction of infarct size. Outcome measurements are proposed at three weeks post-infarction. Although some rats may have no infarction, or only a small infarction is produced, these rats can be identified by normal echocardiograms and normal hemodynamics (LV end-diastolic pressure <8 mm Hg).

Thyroid Hormone Delivery
There are two delivery approaches. In the first, the thyroid hormone conjugated to a nanoparticle may be directly injected into the peri-infarct myocardium. As the demarcation between normal and ischemic myocardium is easily identified during the acute open chest occlusion, this approach provides sufficient delivery of hormone to detect angiogenic effects.

Although the first model is useful in patients undergoing coronary artery bypass surgery, and constitutes proof of principle that one local injection induces angiogenesis, a broader approach using a second model can also be used. In the second model, a catheter retrograde is placed into the left ventricle via a carotid artery in the anesthetized rat prior to inducing myocardial infarction. Alternatively, a direct needle puncture of the aorta, just above the aortic valve, is performed. The intracoronary injection of the thyroid hormone conjugated to a polymer is then simulated by abruptly occluding the aorta above the origin of the coronary vessels for several seconds, thereby producing isovolumic contractions. The conjugated thyroid hormone is then injected into the left ventricle or aorta immediately after aortic constriction. The resulting isovolumic contractions propel blood down the coronary vessels perfusing the entire myocardium with thyroid hormone. This procedure can be done as many times as necessary to achieve effectiveness. The number of injections depends on the doses used and the formation of new blood vessels.

Echocardiography:

A method for obtaining 2-D and M-mode echocardiograms in unanesthetized rats has been developed. Left ventricular dimensions, function, wall thickness and wall motion can be reproducibly and reliably measured. The measurements are carried out in a blinded fashion to eliminate bias with respect to thyroid hormone administration.

Hemodynamics:

Hemodynamic measurements are used to determine the degree of left ventricular impairment. Rats are anesthetized with isoflurane. Through an incision along the right anterior neck, the right carotid artery and the right jugular vein are isolated and cannulated with a pressure transducing catheter (Millar, SPR-612, 1.2 Fr). The following measurements are then made: heart rate, systolic and diastolic BP, mean arterial pressure, left ventricular systolic and end-diastolic pressure, and + and −dP/dt. Of particular utility are measurements of left ventricular end-diastolic pressure, progressive elevation of which correlates with the degree of myocardial damage.

Infarct Size:

Rats are sacrificed for measurement of infarct size using TTC methodology.

Morphometry

Microvessel density [microvessels/mm$^2$] will be measured in the infarct area, peri-infarct area, and in the spared myocardium opposing the infarction, usually the posterior wall. From each rat, 7-10 microscopic high power fields [×400] with transversely sectioned myocytes will be digitally recorded using Image Analysis software. Microvessels will be counted by a blinded investigator. The microcirculation will be defined as vessels beyond third order arterioles with a diameter of 150 micrometers or less, supplying tissue between arterioles and venules. To correct for differences in left ventricular hypertrophy, microvessel density will be divided by LV weight corrected for body weight. Myocardium from sham operated rats will serves as controls.

Example 11

Effects of the αvβ3 Antagonists on the Pro-Angiogenesis Effect of T4 or FGF2

The αvβ3 inhibitor LM609 totally inhibited both FGF2 and T4-induced pro-angiogenic effects in the CAM model at 10 micrograms (FIG. 16).

Example 12

Inhibition of Cancer-Related New Blood Vessel Growth

A protocol disclosed in J. Bennett, Proc Natl Acad Sci USA 99:2211-2215, 2002, is used for the administration of tetraiodothyroacetic (tetrac) to SCID mice that have received implants of human breast cancer cells (MCF-7). Tetrac is provided in drinking water to raise the circulating level of the hormone analog in the mouse model to 10-6 M. The endpoint was the inhibitory action of tetrac on angiogenesis of the implanted primary and metastatic tumors.

Example 13

Efficacy of Tetrac in Retinal Neovascularization in Mice with Retinopathy of Prematurity Retinal angiogenesis is a major cause of blindness in ischemic retinopathies including diabetic retinopathy and retinopathy of prematurity. The mice model used was the Oxygen-induced retinopathy mouse model as described by Smith et al. (Smith L E 1994). As depicted in FIG. 21, the neonatal mice were exposed to hyperoxic conditions for 5 days, beginning at age p7 for the pups and continuing through p12 when they are returned to normal oxygen atmosphere (8-10 animals/group). Three groups were used, the control consisting of treatment with PBS, treatment group consisting of tetrac and a treatment group consisting of tetrac nanoparticles (TNP). Tetrac and TNP (consisting of tetrac PLGA conjugated Nanoparticles via an ester linkage) dosed at 1 mg/kg in PBS at pH 7-7.5, and the Control (PBS) were administered on postnatal day 12 and 15. While PLGA was used, similar results are expected if other polymers were substituted such as polyglycolide, or polylactic acid. The administration was conducted intraperitoneally (IP). The nanoformulation enables for longer residence time on the cornea allowing for greater permeation of tetrac or its tetrac PLGA conjugated Nanoparticles.

On day 17 the animals were scarified and eyes were removed for retinal neovascularization evaluation as summarized in FIG. 21. The eyes were removed fixed in formalin and were stained with H&E stain. As evidenced by the immunohistochemical staining of ROP mice in FIG. 21, normal vessels were present in the eye at room temperature, while capillary drop out occurred between p7 and p12 due to a decrease in VEGF and other angiogenic factors when the $O_2$ were at 75±2%. When the mice were placed back in normal room air, neovascularization is observed due to an increase in VEGF and other angiogenic factors. FIG. 23a depicts the comparison between the effects of exposure to room air versus 75% $O_2$ on the vascularization area of murine retinas. This may be compared with FIG. 23b which depicts the effects of tetrac and tetrac nanoparticles on the vascularization of murine retinas.

FIG. 22 depicts data representing and comparing the mean total area of neovascularization after administration of tetrac at 10 mg/kg, tetrac nanoparticles at 1 mg/kg and the control on day 12 and 15. As seen from the depicted data, the administration of either tetrac or nanoparticulate tetrac resulted in 50% inhibition of neovascularization. The resulting effects are comparable with potent αVβ3 antagonist, XT199. Tetrac and nano-tetrac inhibition of retinal neovascularization in the oxygen-induced retinopathy model makes tetrac a viable therapeutic strategy for proliferative diabetic retinopathy.

Example 14

Nano-Tetrac Exhibiting Both Thyroid Hormone Dependent and Independent Anti-Angiogenic Effects Nanoparticulate tetrac is capable of binding to the αVβ3 receptor on actively dividing endothelial cells. We tested its effects on neovascularization using the chicken chorioallantoic membrane (CAM) model to determine the effectiveness of tetrac and nanoparticulate tetrac conjugated to polymers as described above, in treating neovascularization that occurs from diabetic retinopathy. 10-day-old chick embryos were purchased and incubated at 37° C. with 55% relative humidity. A hypodermic needle was used to make a small hole in the eggshell at the air sac, and a second hole was made on the long side of the egg, directly over an avascular portion of the embryonic membrane identified by candling. A false air sac was created beneath the second hole by distal application of negative pressure to separate the CAM from the shell. A ~1.0 cm$^2$ window was cut in the shell over the dropped CAM, allowing direct access to the underlying membrane. Filter disks that were pre-incubated with FGF2 (1 µg/ml in PBS) were placed on CAMs on day 1. Thirty minutes after filter placement, 2 µg of either tetrac or NT were added to the filter and the eggs were incubated at 37° C. After 3 days, the CAM tissue directly beneath each filter disk was resected, washed three times with PBS, placed in 35 mm petri dishes, and examined under SV6 stereo-microscope (Carl Zeiss, NY) at 50×. Digital images of CAM sections beneath the filters were collected using a 3-charge-coupled device color video camera system (Toshiba America, NY), and the number of branch points in the blood vessels were analyzed with Image-Pro software (Media Cybernetics, MD). The number of branch points in a circular region equal to the area of filter disk were counted. The photomicrographs comparing the CAMS as well as the results are depicted in FIGS. 24a and 24b. Eight CAM preparations were analyzed for each treatment. Each experiment was performed three times, and this procedure was repeated with other related factors and compounds known to promote angiogenesis.

The results show that angiogenesis promoted by T3 and T4 is blocked by nanoparticulate tetrac, which directly blocks T3 and T4 binding to the αVβ3 receptor decreased neovascularization. In addition, independent of thyroid hormone, nanoparticulate tetrac and tetrac, conjugated to polymers also effectively blocks angiogenesis promoted by TNF-α and bFGF via the αVβ3 receptor. Angiogenesis mediated via VEGF is also inhibited by nanoparticulate tetrac, suggesting that nanoparticulate tetrac blocks angiogenesis promoted synergistically by VEGF and the $\alpha_v\beta3$ receptor. Nanoparticulate tetrac also effectively inhibits angiogenesis promoted by bradykinin and angiotensin via FGF2 and VEGFR2, respectively. Additionally, nanoparticulate tetrac inhibits LPS, which promotes angiogenesis via TNF receptor-associated factor 6 (TRAF6)-mediated activation of NFκB and c-Jun N-terminal kinase. Nanoparticulate tetrac thus effectively blocks angiogenesis triggered via multifactorial pathways, a vital quality for a tumor angiogenesis inhibitor, as primary and metastatic tumors utilize multiple angiogenesis promoting factors for their growth.

Example 15

CAM Tumor Growth Studies

For the tumor angiogenesis and tumor growth studies of primary and metastatic tumors, LNCaP or PC3 cells were introduced topically into the CAM. Test compounds were added to the cancer cells in matrigel to assess their ability to target the tumor or tumor vasculature. Tumors were excised, and examined under a stereomicroscope at 50-× magnification. Digital images of the tumor were collected using a 3-CCD color video camera system and analyzed with Image-Pro Plus software as depicted in FIG. 25. The numbers of vessel branch points were counted for each section. Portions of the tumor were extracted for hemoglobin determinations. Studies were performed to evaluate the efficiency and timing of targeted nanoparticles localization into the tumor vasculature using green or red fluorescence-labeled nanoparticles. For example, Alexa-488 labeled nanoparticles were used along with Alexa-543/594-labeled tetrac. Individual CAMs were harvested at various time points after administration of the nanoparticles and the number of fluorescent particles quantified in either tumor vasculature or tumor tissue.

Shown here is an example of LNCaP tumor grown in the CAM. As depicted in FIG. 25, the tumor's 2501 extensive angiogenesis apparent. In the results shown below in Table 3, LNCaP tumors were grown in the tumor implant model. CAMs were treated with PBS (control), tetrac or nanoparticulate tetrac conjugated to polymers via a covalent bond. At the end of the experiment, tumors were removed and weighed, then extracted for measurement of hemoglobin to evaluate the amount of angiogenesis.

Tumor tissue derived from the experiments shown in Table 3 was processed to evaluate angiogenesis by extraction of the tissue and measuring hemoglobin content using Drabkin's reagent. This method correlates well with branch point analysis data (Table 3), showing a similar extent of inhibition of tumor-induced angiogenesis. Data demonstrates that both tetrac and Nanoparticulate tetrac effectively inhibit the growth of these primary and metastatic tumors in the CAM Tumor Implant model. Further, both agents significantly inhibited tumor-induced angiogenesis (FIG. 26), a key factor in metastasis and tumor growth.

TABLE 3

Tetrac and Tetrac-nano inhibit LNCaP Tumor growth and Tumor-induced Angiogenesis in the CAM Tumor Implant Model

| CAM Conditions | Tumor weight ± SEM (mg) | Branch Points ± SEM |
|---|---|---|
| LNCaP (0.5 × 10$^9$ cells/CAM) | 35.3 ± 8.1 | 93.3 ± 8 |
| LNCaP + Tetrac (10 ug/CAM) | 13 ± 3.1* | 59 ± 5.2* |
| LNCaP + Tetrac - nano (1 ug/CAM) | 21 ± 4.4* | 55 ± 3.6* |

Data represent mean ± SEM, n = 8 per group. Either tetrac or Nanoparticulate tetrac resulted in significant suppression of tumor growth or tumor-mediated angiogenesis as compared to untreated LNCaP cancer cells, *P < 0.01. There were no statistically significant differences between tetrac and Nanoparticulate tetrac.

Example 16

Effect of Tetrac on the Proliferation of Drug Resistant Tumors In Vivo

Our in vitro studies demonstrated that tetrac reversed drug resistance in several tumor cell lines. To investigate the in vivo relevance of tetrac in suppressing drug resistance, we tested its effect, either alone or in combination with doxorubicin, in nude mice bearing xenograft of drug resistant cancer cells. While doxorubicin was used in this example, doxorubicin could have been substituted for any of the chemotherapeutic agents described above including etoposide, cyclophosphamide, 5-fluorouracil, cisplatin, trichostatin A, paclitaxel, gemcitabine, taxotere or cisplatinum.

Mice were injected with the doxorubicin-resistant breast cancer cell line MCF7/R and when the tumors became palpable, they received three drug injections of doxorubicin alone, tetrac alone, or the combination of both. The maximal tolerated dose (MTD) for doxorubicin was 2.5 mg/Kg, however, in the case of tetrac; no toxicity was detected for up to 60 mg/ml. The data, which is depicted in FIG. 27, indicates that doxorubicin alone (2 mg/Kg) had no noticeable effect on tumor growth. In contrast, tetrac at 30 mg/ml alone reduced tumor growth by about 70%. This effect was not further improved by the combination of both drugs suggesting a lack of synergistic effect at the concentrations used. Interestingly, the drug concentration of tetrac was well tolerated and no significant weight loss was noticed in the treated animals during the experiments. These findings suggest that tetrac is able to suppress the proliferation of drug resistant tumors in vivo and thus may be capable of treating drug resistant tumors.

Example 17

Anti-Tumor Activity of Tetrac and Tetrac-PLGA Nanoparticles in LNCaP Mice Xenograft Mice were xenografted with 10 million LNCaP cells implanted in matrigel. The mice were treated daily with either tetrac or tetrac-PLGA conjugated polymer nanoparticles. The mice were administered via intraperitoneal injection. The results, as depicted in FIGS. 28a and 28b demonstrate the effectiveness of tetrac and tetrac-PLGA nanoparticles in reducing tumor growth of primary and metastatic tumors in the mice xenografts and the effects on tumor angiogenesis respectively.

Example 18

Suppression of Prostate Tumor Growth Compared with Paclitaxel

Tumor fragments (1 mm$^3$) were prepared from prostate tumors growing subcutaneously in nude mice. Either Lucefrin transfected prostate cancer cell lines (1 million cells) or tumor fragments were implanted by surgical orthotopic implantation in the lateral lobe of the prostate, which was exposed after a lower midline abdominal incision. After proper exposure of the bladder and prostate, the capsule of the prostate was opened and the two tumor fragments (1 mm$^3$) were inserted into the capsule. The capsule was then closed with an 8-0 surgical suture. The incision in the abdominal wall was closed with a 6-0 surgical suture in one layer. The animals were kept under isoflurane anesthesia during surgery. All procedures of the operation described above were performed using a surgical microscope.

Male nude mice were implanted orthotopically with prostate cancer cell transfected with lucefrin and animals were randomized into 3 different arms as shown below:
1. PBS 1 ml/kg, IP daily (n=4)
2. Paclitaxel 0.3 mg/kg, IP daily (n=5)
3. Tetrac 1 mg/kg, IP daily (n=5)

As depicted in FIG. 29, the tetrac administered intraperitoneally at 1 mg/kg daily for 17 days resulted in distinct suppression of prostate tumor growth comparable to the reduction obtained by the cytotoxic, chemotherapeutic agent, paclitaxel.

Example 19

Nanoparticulate Tetrac Exerts Anti-Proliferative Effects on Pancreatic Adenocarcinoma Cells In this study, we used any two of the following: Panc-1, MiaPaCa-2 and AsPc-1 PDAC cell lines, as they all express significant levels of αVβ3. Cells were counted and plated in media with either tetrac or nanoparticulate tetrac (10 μM). Media were replenished daily with fresh tetrac and nanoparticulate tetrac (NT-1 or NT-2 batches). Viable cells were counted by trypan blue exclusion assays. Cells were cultured for 8 days in the presence of the vehicle (control), tetrac and nanoparticulate tetrac. As depicted in FIG. 30, cells were counted on days 3, 6 and 8. By day 8, the Panc-1 cell counts (data not shown for AsPc-1 cells) were reduced by approximately 20% with tetrac treatment (*P<0.04) and by 35-40% with nanoparticulate tetrac treatment (**P≤0.01), compared to untreated cells. Both unmodified tetrac and nanoparticulate tetrac effectively reduced proliferation in Panc-1 cells. Nanoparticulate tetrac was show to be more effective than tetrac.

Example 20

Nanoparticulate Tetrac Regulates Gene Expression to Inhibit Cell Survival, Cell Proliferation and Angiogenesis Using microarray analysis, we found that both tetrac and nanoparticulate tetrac alter the expression of genes relevant to cell division and angiogenesis in human breast cancer cells and in medullary thyroid carcinoma cells. We used western analysis to test the expression of the pro-apoptotic protein, bcl-Xs, and the anti-angiogenic protein thrombospondin (THBS1), in AsPc-1 and Panc-1. We also used RT-PCR to analyze expression of the mRNAs for the cell cycle regulatory genes p21 and p53. To do this, cells were plated, treated with either tetrac or nanoparticulate tetrac. Total cell extracts were probed with anti-bcl-Xs, anti-THBS1, and anti-β-actin (loading control) antibodies. Tetrac and nanoparticulate tetrac both increased bcl-Xs and THBS1 protein expression by 2-fold and 4-fold, respectively, compared to the untreated controls as depicted in FIG. 31a. These results suggest that the anti-angiogenic and anti-survival effects of nanoparticulate tetrac and tetrac occur via modulation of gene expression. Data with AsPc-1, p21 and p53 (GAPDH, internal controls) mRNA levels were significantly decreased by both tetrac and nanoparticulate tetrac, while nanoparticulate tetrac alone significantly reduced EGFR expression levels (as depicted in FIG. 31b and FIG. 31c), which collectively could slow cell cycle progression. Thus, nanotetrac affects cell proliferation, cell survival, and angiogenesis by modulating gene expression.

Example 21

Tetrac Exerts Anti-Tumorigenic and Anti-Angiogenic Effects on Pancreatic Xenograft To complement our in vitro observations, we tested the effects of tetrac and nanoparticulate tetrac conjugated to polymers via a covalent bond on primary and metastatic tumor growth, and tumor angiogenesis in vivo. Female nude mice were purchased at age 5-6 weeks (20 g body weight) and housed in the animal facility. The animal protocol was approved by the Institutional Animal Care and Use Committee (IACUC). Approximately 2×10$^6$ AsPc-1 cells in 100 μl of growth medium were mixed with 100 μl of Matrigel® and injected subcutaneously into the left and right flanks (2 per side) of 18 animals. Tumors (4 per animal) were measured daily with calipers, and tumor volumes were calculated using the formula, W×L$^2$/2, where W is width and L is length. When the tumor volumes reached ~250 mm$^3$, the animals were randomized into 3 groups (n=6/group) and subcutaneously injected with solvent (control), tetrac (10 mg/kg body weight), or nanoparticulate tetrac (1 mg/kg body weight). Tumor volumes were measured daily for the next 15 days. As shown in FIG. 32a-c, untreated animal tumor volumes continued to increase until the 15th day of treatment. Treatment with either tetrac or nanoparticulate tetrac resulted in progressive reductions of the tumor volumes of AsPc-1 xenograft, which reached statistical significance by treatment days 5-6 ($P<0.05$). By the end of day 15 of treatment, both agents decreased the tumor volume to that of the original implant. On the last day of tumor measurement, the animals were observed by IVIS imaging as depicted in FIG. 32b, which revealed that the reductions in tumor mass correlated with reductions in the number of viable cells, indicated by reduced luciferase signal intensities. The animals were humanely sacrificed and their tumors were harvested.

The hemoglobin contents of the tumor masses were measured to obtain an indirect estimate of vascularity. For this purpose, each tumor was homogenized in double-distilled water, centrifuged (4,000×g for 10 min), and the supernatants were collected. 50 µl of each supernatant was mixed with 50 µl of Drabkin's reagent, incubated at room temperature for 30 min, transferred to 96-well plates, and absorbances were measured at 540 nm using a micro-plate reader. The hemoglobin concentration (mg/mL) was estimated from a standard curve. To establish the use of tumor hemoglobin content as a measure for tumor neovascularization, we validated a linear correlation between tumor hemoglobin content with the degree of tumor neovascularization using anti-CD31 staining. As shown in FIG. 32c, the hemoglobin contents of the xenograft (an index of tumor angiogenesis) collectively decreased by 60% in animals treated for 15 days with tetrac or tetrac nanoparticles (*$P<0.05$), compared with tumors in untreated control animals. Thus, both tetrac and NT at tenfold lower doses significantly decreased tumor growth and tumor angiogenesis in an in vivo xenograft pancreatic tumor model.

Example 22

Nanoparticulate Tetrac Sensitizes Drug-Resistant Pancreatic Cells to Gemcitabine Pancreatic ductal adenocarcinoma (PDAC) patients have poor survival rates, in part due to increased resistance to chemotherapy. Previous studies suggest that the αVβ3 receptor promotes drug resistance in cancer cells and that non-genomic actions of thyroid hormone (TH) regulate the expression of genes that are relevant to drug resistance via αVβ3 receptor. This led us to hypothesize that nanoparticulate tetrac reverses drug resistance in pancreatic cells expressing the αVβ3 receptor by binding to the receptor and blocking both TH-dependent and TH-independent downstream pathways. We used MiaPaCa-2 cells that express αVβ3 receptor and are resistant to gemcitabine. Equal numbers of cells were plated and treated with nanoparticulate tetrac alone (5 µg/ml), gemcitabine alone (1 µM) or nanoparticulate tetrac with gemcitabine. After 36 hours, cell survival was measured using an Apo-direct kit, which labels DNA breaks so that apoptotic cells can be detected by flow cytometry. As depicted in FIG. 33, we found that gemcitabine treatment alone resulted in death of 5% of the cells, while nanoparticulate tetrac treatment alone resulted in 10% cell death. However, nanoparticulate tetrac in combination with gemcitabine increased the cell death to 15%. This result suggests that nanoparticulate tetrac treatment caused gemcitabine-resistant cells to become susceptible to gemcitabine treatment. Thus, nanoparticulate tetrac treatment of chemo-resistant PDAC cells expressing the αVβ3 receptor resulted in the cells becoming chemo-sensitive.

Example 23

Nanoparticulate Tetrac Regulates the Expression of miRNA-15a

Nanoparticulate tetrac may mediate a wide array of anti-cancer activities via αVβ3 receptor that are both TH-dependent and TH-independent. MiRNAs play key roles in controlling the expression of many cellular proteins, enabling them to regulate many cellular pathways and thus any deregulation in their physiological levels may largely contribute to diseases. Recent evidence showed that T3 hormone increased miR-350 expression in cardiomyocytes, which in turn stabilized the transcripts of angiotensin II type 1 receptor (AT1R) gene to increase its translational efficiency. This suggests that TH can mediate gene expression by regulating miRNA levels. We hypothesized that nanoparticulate tetrac, which blocks the effects of T3 and T4 at αVβ3 receptor may also be able to regulate miRNAs. Emerging evidence shows that alterations of miRNA expression, such as miR-21, miR-10b and miR-15a play a significant role in tumorigenesis. We therefore investigated if nanoparticulate tetrac treatment regulated the expression of miR-15a, which is also shown to regulate cell proliferation, angiogenesis and chemoresistance in various cancer types.

In PDAC, the levels of miR-15a are down regulated and overexpression of exogenous miR-15a inhibited the viability of pancreatic cancer cells. We therefore determined whether nanoparticulate tetrac up-regulates miR-15a expression in PDAC cells. Equal numbers of AsPc-1 cells were seeded and treated with nanoparticulate tetrac, for 16 hours. Enriched miRNAs were isolated from the cells, using miRNeasy kit, reverse transcribed and qPCR was performed to amplify miR-15a and RNU6 miRNA, an internal control, in triplicate. The expression of miR-15a in nanoparticulate tetrac treated sample relative to that in untreated was determined to be 1.4 fold by calculating relative quantification (RQ), which is the fold change compared to the calibrator (RNU6), as shown in Table 4 below. Thus, nanoparticulate tetrac treatment increases the miR-15a levels by 1.4 fold compared to untreated sample with 95% confidence interval. We expect the fold-difference to increase, with longer treatment time.

TABLE 4

| Relative Quantification (RQ) of miR-15a in AsPc-1 cells. | | |
| --- | --- | --- |
| Sample | RQ | 95% Conf. Int. |
| Untreated | 1 | 0.918-1.089 |
| NT | 1.379 | 1.353-1.406 |

Example 24

Effects of Tetrac and Nanotetrac on Non-Small Cell Lung Cancer

Cells and cell culture: Human non-small cell lung cancer (NSCLC) NCI-H1299 cells were purchased from American Type Culture Collection (Manassas, Va.) and cultured as instructed by the supplier, using complete growth RPMI medium supplemented with 10% FBS. Cells were cultured in a 5% CO2/air atmosphere at 37° C. to sub-confluence and then treated with 0.25% (w/v) trypsin/EDTA to affect cell release from the culture vessel. After cells were washed with culture medium, they were suspended in DMEM that was free of phenol red and FBS and counted.

We studied the inhibitory effect of tetrac and tetrac NP xenograft growth in nude mice. Xenografts of 4×106 H1299 cells were implanted and animals were treated IP with unmodified tetrac (1 mg/kg body weight) or tetrac-NP (1 mg tetrac as the nanoparticle/kg) every 2 d, beginning on day 10, when tumor volume was 200-300 mm³. A factor contributing to increase in tumor volume is assumed to be endogenous thyroid hormone. Treatment with either tetrac or tetrac-NP resulted within 2-3 d in reduction of tumor volume (FIG. 34) and for the 20-d duration of treatment the volume rose negligibly above that at day zero (FIG. 34). At the end of the study, tumor mass was directly measured and, compared to controls, both agents resulted in significant ($p<0.01$) reduction of mass (FIG. 35A). In FIG. 35B, tumor hemoglobin (Hgb) content, an index of vascularity/angiogenesis, is shown to be reduced by both tetrac formulations. Animal body weight was unaffected by tetrac and tetrac NP.

Additional studies were conducted of the effectiveness of tetrac and tetrac-NP against larger tumor implants. Implants of 107 NCI-H1299 cells (10-fold the implant size shown in FIGS. 35-36) resulted in greater xenograft growth in control animals. Daily treatment of animals with tetrac (2.0 mg/kg, IP) or tetrac-NP (1.86 mg tetrac as the nanoparticle/kg, IP) resulted in suppression in tumor growth within 2-3 d (FIG. 36A). This difference in growth rate persisted throughout the 20-d duration of the study. Both agents resulted in significant ($p<0.01$) inhibition of tumor mass, compared to control (FIG. 36B).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for treating a condition amenable to the inhibition of angiogenesis comprising the steps of:
   administering to a subject in need thereof an effective amount of a compound selected from the group consisting of tetraiodothyroacetic acid (tetrac), triiodothyroacetic acid (triac) and a combination thereof conjugated via a covalent bond to a polymer, wherein said polymer is polyglycolide, polylactic acid, or co-polymers thereof, wherein said polymer is formulated into a nanoparticle, wherein said nanoparticle is less than 200 nanometers, and wherein the administered compound acts at the cell membrane level to inhibit pro-angiogenesis agents.

2. The method of claim 1, wherein the condition amenable to treatment by anti-angiogenesis is selected from the group consisting of a primary tumor, metastatic tumor and diabetic retinopathy.

3. The method of claim 1, wherein the covalent bond is selected from a group consisting of an ester linkage, ether linkage, sulfhydryl linkage, and an anhydride linkage.

4. The method of claim 1, wherein the step of administering includes a route of administration selected from the group consisting of parenteral, oral, rectal, topical, intratumoral, intraocular, and combinations thereof.

5. The method according to claim 1, wherein the compound is co-administered with at least one chemotherapeutic agent.

6. The method according to claim 5, wherein the at least one chemotherapeutic agent is selected from a group consisting of doxorubicin, etoposide, cyclophophamide, 5-fluoracil, cisplatin, trichostatin A, paclitaxel, gemcitabine, taxotere, cisplatinum, carboplatinum, irinotecan, topotecan, adrimycin, bortezomib, combinations thereof and derivatives thereof.

* * * * *